US010463671B2

(12) United States Patent
Keilhack et al.

(10) Patent No.: US 10,463,671 B2
(45) Date of Patent: Nov. 5, 2019

(54) COMBINATION THERAPY FOR TREATING CANCER

(71) Applicant: Epizyme, Inc., Cambridge, MA (US)

(72) Inventors: Heike Keilhack, Belmont, MA (US); Sarah K. Knutson, Lincoln, MA (US); Kevin W. Kuntz, Woburn, MA (US)

(73) Assignee: Epizyme, Inc., Cambridge, MA (US)

( * ) Notice: Subject to any disclaimer, the term of this patent is extended or adjusted under 35 U.S.C. 154(b) by 0 days.

(21) Appl. No.: 15/809,445

(22) Filed: Nov. 10, 2017

(65) Prior Publication Data

US 2018/0280402 A1 Oct. 4, 2018

Related U.S. Application Data

(63) Continuation of application No. 15/101,577, filed as application No. PCT/US2014/069167 on Dec. 8, 2014, now abandoned.

(60) Provisional application No. 61/992,881, filed on May 13, 2014, provisional application No. 61/934,388, filed on Jan. 31, 2014, provisional application No. 61/913,063, filed on Dec. 6, 2013.

(51) Int. Cl.

| | |
|---|---|
| *A61K 31/5377* | (2006.01) |
| *C07K 16/28* | (2006.01) |
| *A61K 31/573* | (2006.01) |
| *A61K 45/06* | (2006.01) |
| *A61K 39/395* | (2006.01) |
| *A61K 31/69* | (2006.01) |
| *A61K 31/675* | (2006.01) |
| *A61K 31/635* | (2006.01) |
| *A61K 31/404* | (2006.01) |
| *A61K 31/52* | (2006.01) |
| *A61K 31/519* | (2006.01) |
| *A61K 31/4965* | (2006.01) |
| *A61K 31/496* | (2006.01) |
| *A61K 31/4375* | (2006.01) |
| *A61K 31/436* | (2006.01) |
| *A61K 39/00* | (2006.01) |

(52) U.S. Cl.
CPC ........ *A61K 31/5377* (2013.01); *A61K 31/404* (2013.01); *A61K 31/436* (2013.01); *A61K 31/4375* (2013.01); *A61K 31/496* (2013.01); *A61K 31/4965* (2013.01); *A61K 31/519* (2013.01); *A61K 31/52* (2013.01); *A61K 31/573* (2013.01); *A61K 31/635* (2013.01); *A61K 31/675* (2013.01); *A61K 31/69* (2013.01); *A61K 39/3955* (2013.01); *A61K 45/06* (2013.01); *C07K 16/2887* (2013.01); *A61K 2039/505* (2013.01)

(58) Field of Classification Search
CPC .................................................. A61K 31/5377
USPC ..................................................... 514/228.8
See application file for complete search history.

(56) References Cited

U.S. PATENT DOCUMENTS

| | | | |
|---|---|---|---|
| 8,410,088 B2 | 4/2013 | Kuntz et al. | |
| 8,691,507 B2 | 4/2014 | Copeland et al. | |
| 8,765,732 B2 | 7/2014 | Kuntz et al. | |
| 8,895,245 B2 | 11/2014 | Copeland et al. | |
| 9,090,562 B2 | 7/2015 | Kuntz et al. | |
| 9,175,331 B2 | 11/2015 | Kuntz et al. | |
| 9,333,217 B2 | 5/2016 | Copeland et al. | |
| 9,334,527 B2 | 5/2016 | Kuntz et al. | |
| 9,522,152 B2 | 12/2016 | Kuntz et al. | |
| 9,549,931 B2 | 1/2017 | Kuntz et al. | |
| 10,166,238 B2 | 1/2019 | Keilhack et al. | |
| 2012/0264734 A1* | 10/2012 | Kuntz ........... | C07D 213/64 514/210.18 |
| 2013/0040906 A1 | 2/2013 | Kuntz et al. | |
| 2014/0120083 A1* | 5/2014 | Stern ............ | A61K 31/00 424/133.1 |
| 2014/0128393 A1 | 5/2014 | Knutson et al. | |
| 2015/0051163 A1 | 2/2015 | Keilhack et al. | |
| 2017/0065600 A1 | 3/2017 | Kuntz et al. | |
| 2017/0065628 A1 | 3/2017 | Copeland et al. | |

FOREIGN PATENT DOCUMENTS

| | | |
|---|---|---|
| WO | WO 2012/034132 | 3/2012 |
| WO | WO 2012/118812 A2 | 9/2012 |
| WO | WO 2012/142504 A1 | 10/2012 |
| WO | WO 2012/142513 A1 | 10/2012 |
| WO | WO 2013/049770 A2 | 4/2013 |
| WO | WO 2013/138361 A1 | 9/2013 |
| WO | WO 2013/155317 A1 | 10/2013 |
| WO | WO 2013/155464 | 10/2013 |
| WO | WO 2013/173441 | 11/2013 |
| WO | WO 2014/062720 A2 | 4/2014 |
| WO | WO 2014/062732 A1 | 4/2014 |
| WO | WO 2014/062733 A2 | 4/2014 |
| WO | WO 2014/071109 A1 | 5/2014 |
| WO | WO 2014/100646 A1 | 6/2014 |
| WO | WO 2014/100665 A1 | 6/2014 |
| WO | WO 2014/144747 A1 | 9/2014 |
| WO | WO 2014/172044 A1 | 10/2014 |
| WO | WO 2014/194254 A1 | 12/2014 |
| WO | WO 2015/010049 A1 | 1/2015 |
| WO | WO 2015/010078 A2 | 1/2015 |
| WO | WO 2015/057859 A1 | 4/2015 |
| WO | WO 2015/058125 A1 | 4/2015 |
| WO | WO 2015/195848 A1 | 12/2015 |
| WO | WO 2016/081523 A1 | 5/2016 |
| WO | WO 2016/172199 | 10/2016 |
| WO | WO 2016/201328 | 12/2016 |

OTHER PUBLICATIONS

Lannutti et al., Blood, (2011), 117(2), p. 591-594. (Year: 2011).*

(Continued)

*Primary Examiner* — Yong L Chu
(74) *Attorney, Agent, or Firm* — Cooley LLP; Heidi A. Erlacher; Christine C. Pemberton

(57) ABSTRACT

The present invention relates to compositions comprising inhibitors of human histone methyltransferase EZH2 and one or more other therapeutic agents, particularly anticancer agents such as prednisone, and methods of combination therapy for administering to subjects in need thereof for the treatment of cancer.

25 Claims, 28 Drawing Sheets

(56) References Cited

OTHER PUBLICATIONS

Brunton, L. et al. (Eds.) "Antineoplastic Agents" Chapter 51 in *Goodman & Gilman's Manual of Pharmacology and Therapeutics*. McGraw-Hill Medical, 2008; pp. 853-861 (eBook). EBSCO Publishing: eBook Collection (EBSCOhost), retrieved on Dec. 21, 2015.
ClinicalTrials.gov *archive*, (Aug. 21, 2014) "View of NCT01897571 on Aug. 21, 2014. An Open-Label, Multicenter, Phase ½ Study of E7438 (EZH2 Histone Methyl Transferase [HMT] Inhibitor) as a Single Agent in Subjects With Advanced Solid Tumors or With B Cell Lymphomas" Clinical Trials Identifier: NCT01897571 [online]. Retrieved from: https://clinicaltrials.gov/archive/NCT01897571/2014_08_21; 7 pages.
ClinicalTrials.gov *archive*, (Mar. 27, 2014) "View of NCT01897571 on Mar. 27, 2014. An Open-Label, Multicenter, Phase ½ Study of E7438 (EZH2 Histone Methyl Transferase [HMT] Inhibitor) as a Single Agent in Subjects With Advanced Solid Tumors or With B Cell Lymphomas" Clinical Trials Identifier: NCT01897571 [online]. Retrieved from: https://clinicaltrials.gov/archive/NCT01897571/2014_03_27; 7 pages.
ClinicalTrials.gov(Mar. 28, 2017) "Open-Label, Multicenter, Phase ½ Study of Tazemetostat (EZH2 Histone Methyl Transferase [HMT] Inhibitor) as a Single Agent in Subjects With Advanced Solid Tumors or With B-cell Lymphomas and Tazemetostat in Combination With Prednisolone in Subjects With DLBCL" Clinical Trials Identifier: NCT01897571 [online]. Retrieved from: https://clinicaltrials.gov/ct2/show/NCT01897571; retrieved on Apr. 20, 2017; 5 pages.
Dyer, M. et al. (1990) "A New Human B-Cell Non-Hodgkin's Lymphoma Cell Line (Karpas 422) Exhibiting Both t(14;18) and t(4;11) Chromosomal Transolcations" *Blood*, vol. 75, No. 3, p. 709-714.
Epizyme, Inc. (Nov. 19, 2014) "Phase 1 Dose Escalation Data for Epizyme EZH2 Inhibitor EPZ-6438 (E7438) Shows Single Agent Activity in B-Cell Non-Hodgkin Lymphomas and Malignant Rhabdoid Tumor" [online]. *Business Wire*[online]. Retrieved from: http://www.businesswire.com/news/home/20141119006836/en/Phase-1-Dose-Escalation-Data-Epizyme-EZH2; 4 pages.
Garapaty-Rao, S. et al. (Nov. 21, 2013) "Identification of EZH2 and EZH1 Small Molecule Inhibitors with Selective Impact on Diffuse Large B Cell Lymphoma Cell Growth" *Chem Biol*, 20:1329-1339.
Hassan, U. et al. (2012) "Prognostic Sub-Grouping of Diffuse Large B-Cell Lymphomas into Germinal Centre and Post Germinal Centre Groups by Immunohistochemistry after 6 Cycles of Chemotherapy" *Asian Pacific Journal of Cancer Prevention*, vol. 13, p. 1341-1347.

Knutson, S.K. et at (2014) "Selective Inhibition of EZH2 by EPZ-6438 Leads to Potent Antitumor Activity in EZH2-Mutant Non-Hodgkin Lymphoma" *Molecular Cancer Therapeutics*, vol. 13, No. 4, pp. 842-854.
Knutson, S.K. et at (Dec. 10, 2014) "Synergistic Anti-Tumor Activity of EZH2 Inhibitors and Glucocorticoid Receptor Agonists in Models of Germinal Center Non-Hodgkin Lymphomas" *PLOS ONE*, 9(12):e111840; DOI: 10.1371/journal.pone.0111840; 22 pages.
Qi, W. et al. (2012) "Selective inhibition of Ezh2 by a small molecule inhibitor blocks tumor cells proliferation" *Proc Natl Acad Sci USA*, vol. 109, No. 52, pp. 21360-21365.
Varambally, S. et al. (Oct. 10, 2002) "The Polycomb Group Protein EZH2 Is Involved in Progression of Prostate Cancer" *Nature*, 419:624-629.
Advani, R.H. et al. (Jan. 2013) "Bruton tyrosine kinase inhibitor ibrutinib (PCI-32765) has significant activity in patients with relapsed/refractory B-cell malignancies" *J Clin Oncol*, 31(1):88-94.
Petrich, A. et al. (2012) "Akt Inhibitors MK-2206 and Nelfinavir overcome mTOR inhibitor resistance in DLBCL" Author Manuscript [online]. Retrieved from the Internet: www.clincancerres.aacrjournals.org; retrieved on Nov. 28, 2018, 3 pages. Final publication in: *Clin Cancer Res*, 18(9):2534-2544.
Xian G, C-Y. et al. (Mar. 2012) "Recent advance in the role of TNF-α in cancer" *Chinese Bulletin of Life Sciences*, 24(3):250-254 (Chinese with English abstract).
Definition of "R-CHOP", National Cancer Institute Web Site; https://www.cancer.gov/about-cancer/treatment/drugs/R-CHOP, posted Sep. 18, 2009; updated May 29, 2012, 2 pages.
Knutson, S. K. et al., "Durable tumor regression in genetically altered malignant rhabdoid tumors by inhibition of methyltransferase EZH2," PNAS, 2013, pp. 7922-7927, vol. 110, No. 19.
Knutson, S. K. et al., "A selective inhibitor of EZH2 blocks H3K27 methylation and kills its mutant lymphoma cells," Nature Chemical Biology, 2012, pp. 890-896, vol. 8, No. 1.
McCabe, M. T. et al., "EZH2 inhibition as a therapeutic strategy for lymphoma with EZH2-activating mutations," Nature, 2012, pp. 108-112, vol. 492.
clinicaltrials.gov(Dec. 14, 2018) "Open-Label, Multicenter, Phase ½ Study of Tazemetostat (EZH2 Histone Methyl Transferase [HMT] Inhibitor) as a Single Agent in Subjects With Advanced Solid Tumors or With B-cell Lymphomas and Tazemetostat in Combination With Prednisolone in Subjects With DLBCL" Bethesda (MD): National Library of Medicine (US). Identifier: NCT01897571 [online]. Retrieved from: https://clinicaltrials.gov/ct2/show/NCT01897571; retrieved on Jan. 1, 2019, 6 pages.

* cited by examiner

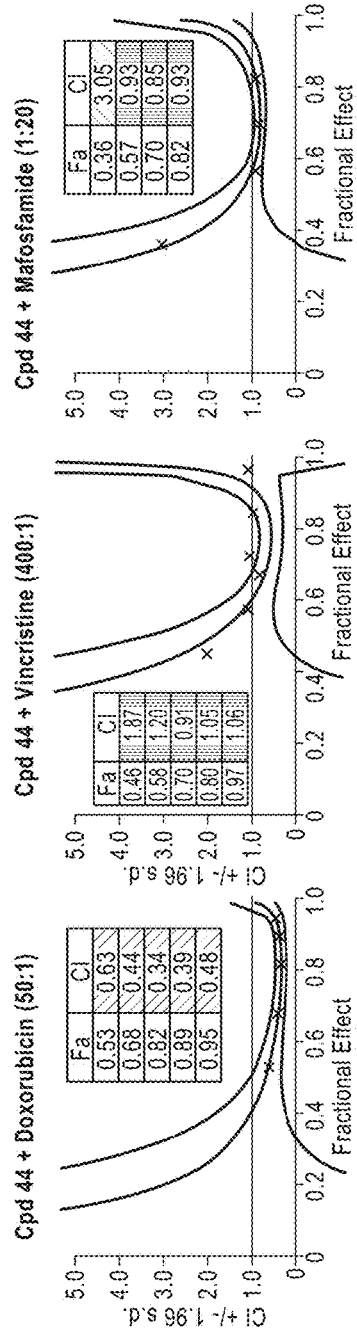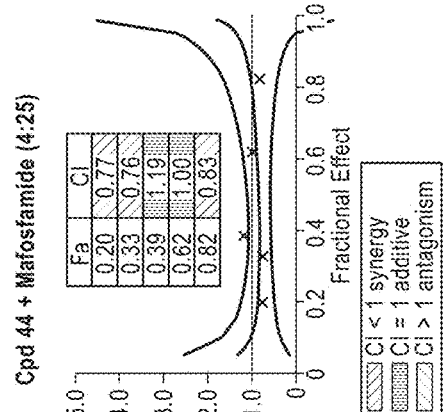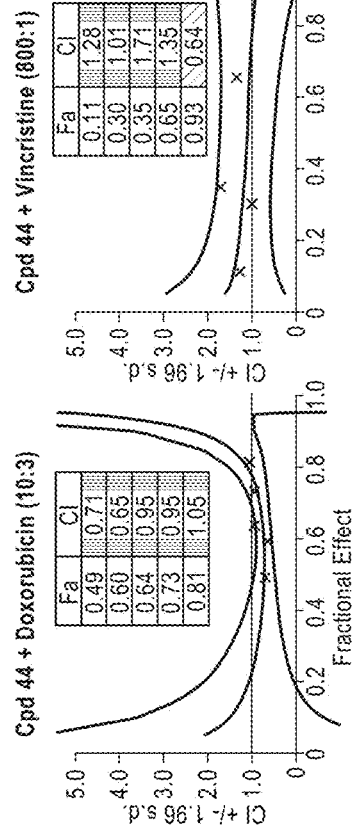

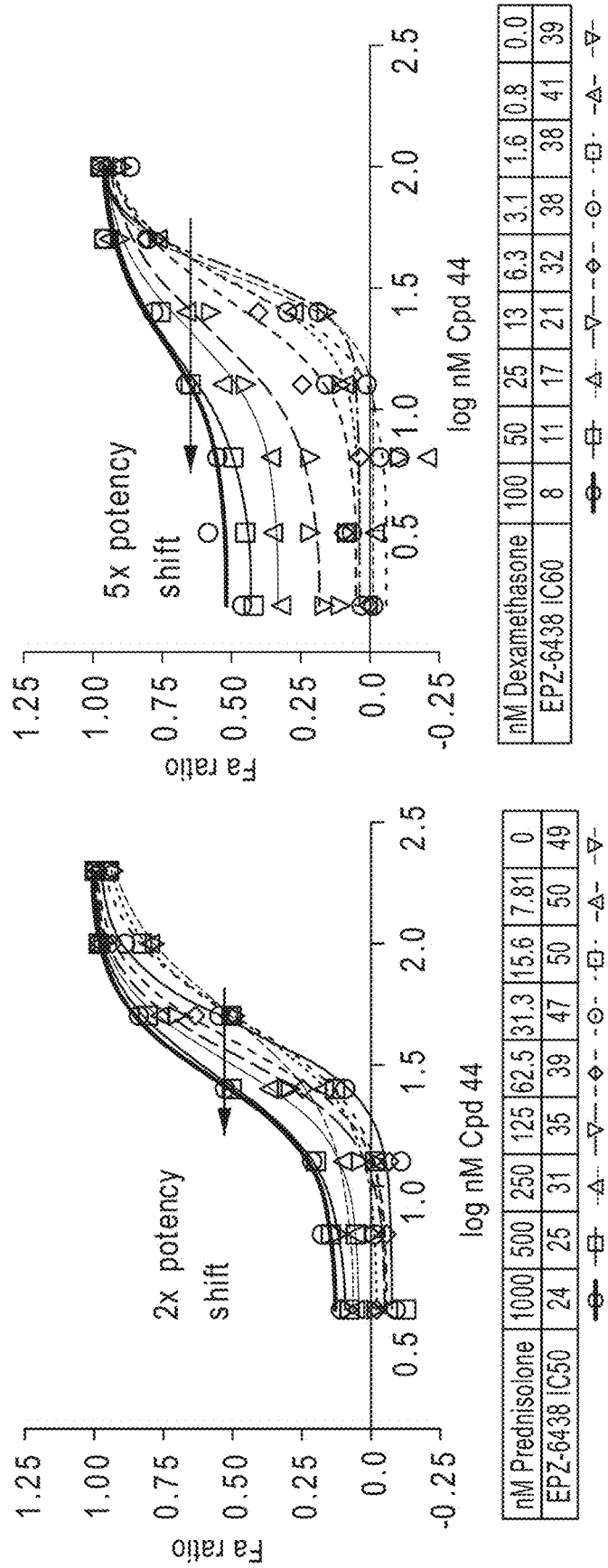

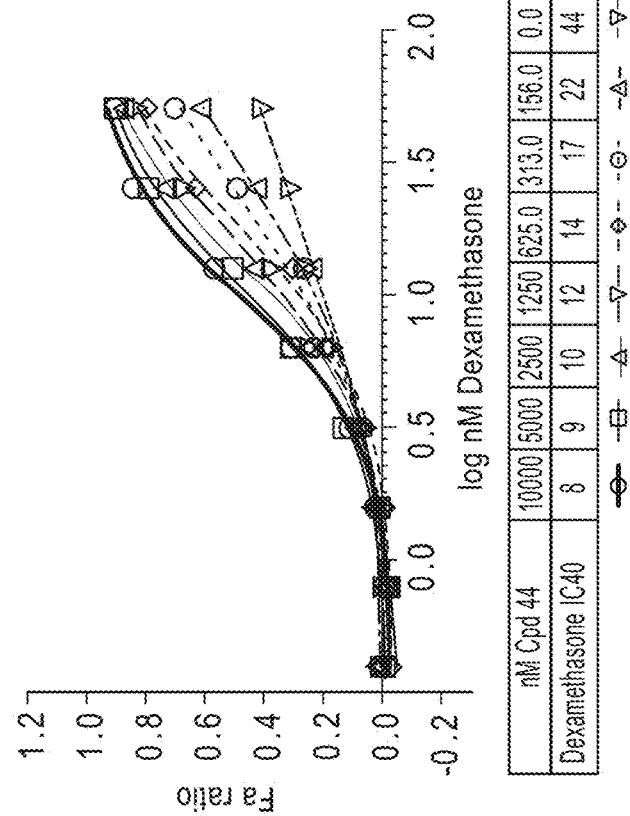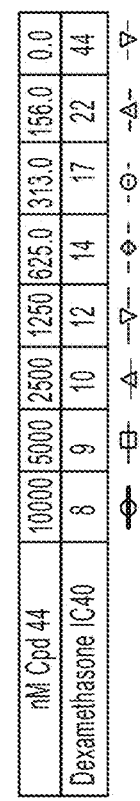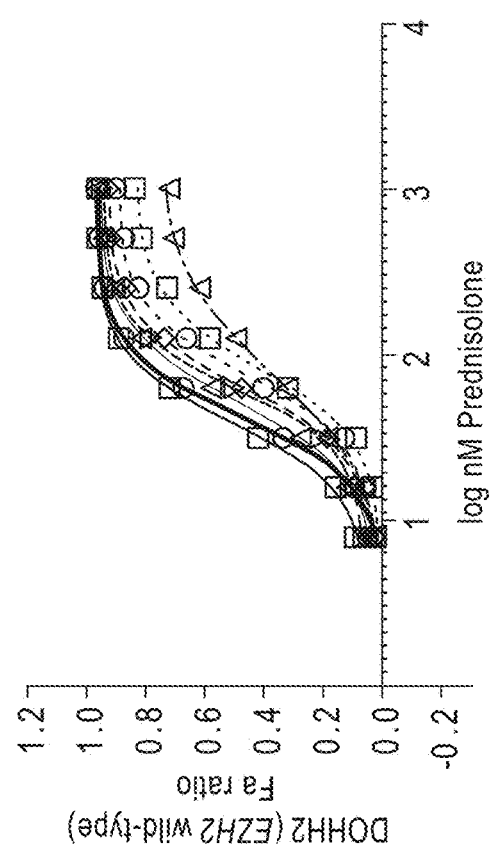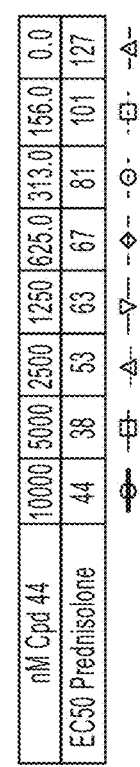
FIG. 3C  FIG. 3D

| Cell Line | 4 Day Cpd44 IC₅₀ (uM) | | | 7 Day Cpd44 IC₅₀ (uM) | | |
| --- | --- | --- | --- | --- | --- | --- |
| | Cpd44 Alone | Cpd44 Co-treatment | | 4d Cpd44 Pre/ 3d Co-treat | 4d Pred Pre/ 3d Co-treat | 7d Co-treatment |
| WSU (Y646-Sens) | 0.53 +/- 0.014 | 0.020 +/- 0.021 | | 0.011 +/- 0.0062 | >1 | 0.014 +/- 0.0049 |
| SU-DHL10 (Y646-Sens) | 0.64 +/- 0.26 | 0.0092 +/- 0.0044 | | 0.0027 +/- 0.0013 | 0.52, >1 | 0.020 +/- 0.0057 |
| RL (Y646-Res) | >1 | 0.0096 +/- 0.0066 | | <<0.004 | 0.38 | <0.004 |
| SU-DHL4 (Y646-Res) | >1 | >1, 0.2, >1 | | 0.035 +/- 0.043 | >1 | 0.51 +/- 0.35 |
| DOHH2 (WT) | >1 | 0.20 +/- 0.25 | | >1, 0.03, >1 | >1 | 0.34 +/- 0.078 |
| OCI-Ly19 (WT) | >1 | 0.19 +/- 0.11 | | 0.0055 +/- 0.0047 | >1 | 0.026, <0.004 |

FIG. 4

| | | WSU-DLCL2 (EZH2 mutant GCB) | SU-DHL-10 (EZH2 mutant GCB) | Toledo (WT EZH2 GCB) | DOHH2 (WT EZH2 GCB) |
|---|---|---|---|---|---|
| Standard of Care DLBCL | Prednisolone | 7x potency enhancement | 2x potency enhancement | no effect | 2x potency enhancement |
| | Doxorubicin | synergy | additive | no effect | no effect |
| | Mafosfamide | additive | additive | no effect | no effect |
| | Vincristine | additive | additive | no effect | no effect |
| | Cisplatin | synergy | additive | no effect | no effect |
| | AraC | synergy | additive | no effect | no effect |
| Epigenetic Drugs | Vorinostat | additive | additive | no effect | no effect |
| | Panobinostat* | additive | Not tested | Not tested | Not tested |
| | Azacytadine* | additive | Not tested | Not tested | Not tested |
| Other Therapies | Everolimus | very strong synergy | strong synergy | no effect | no effect |
| | Dexamethasone | 15x potency enhancement | 5x potency enhancement | no effect | 4x potency enhancement |
| | Navitoclax | very strong synergy | 2x potency enhancement | Not tested | No effect |
| | Obatoclax | additive | additive | Not effect | No effect |

No effect = No change in drug IC$_{50}$ upon addition of Cpd 44
* Experiments were performed with EZH2i tool compound instead of Cpd 44.

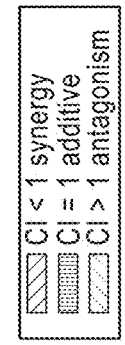

CI < 1 synergy
CI = 1 additive
CI > 1 antagonism

FIG. 6

FIG. 7A
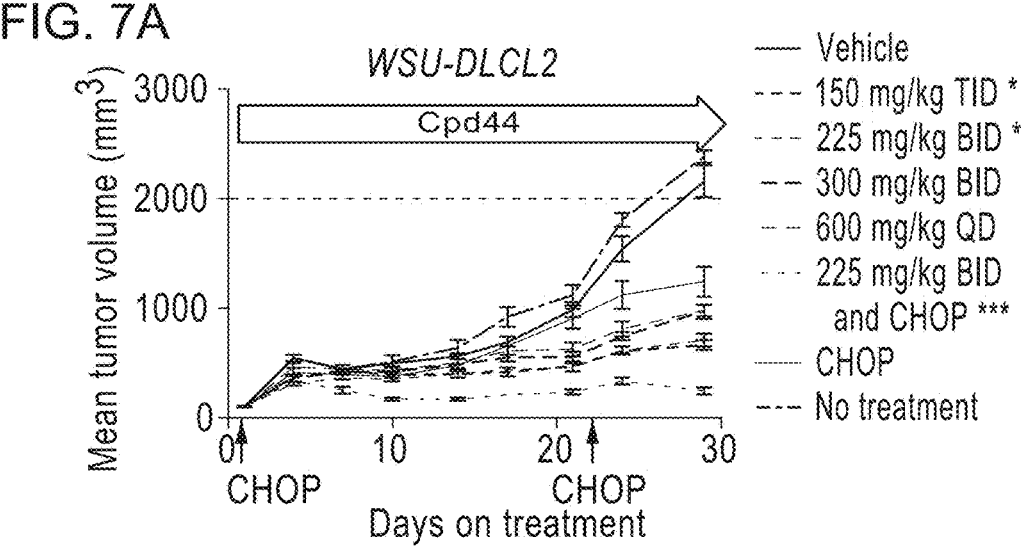
FIG. 7B
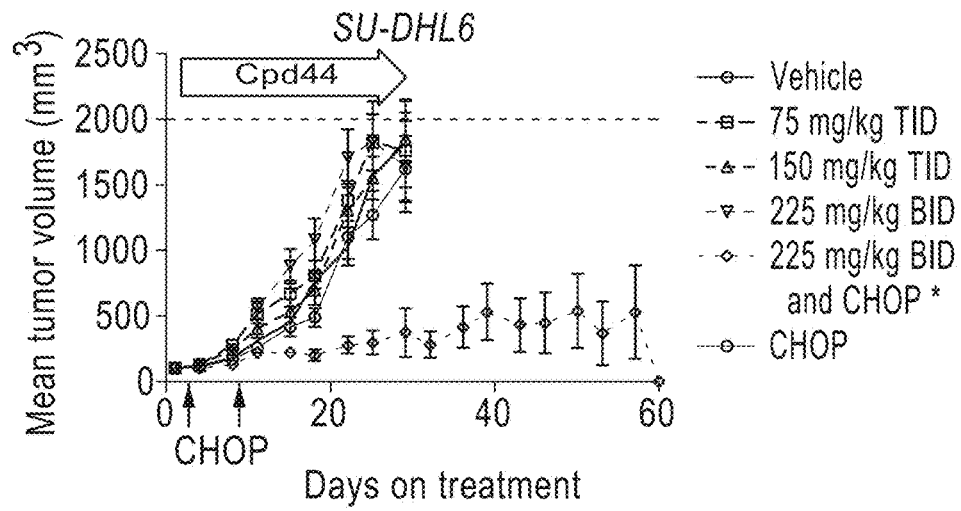
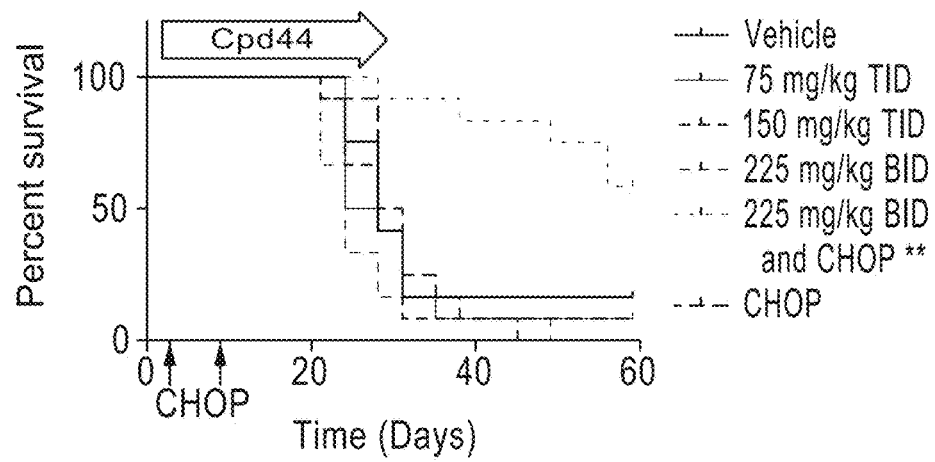

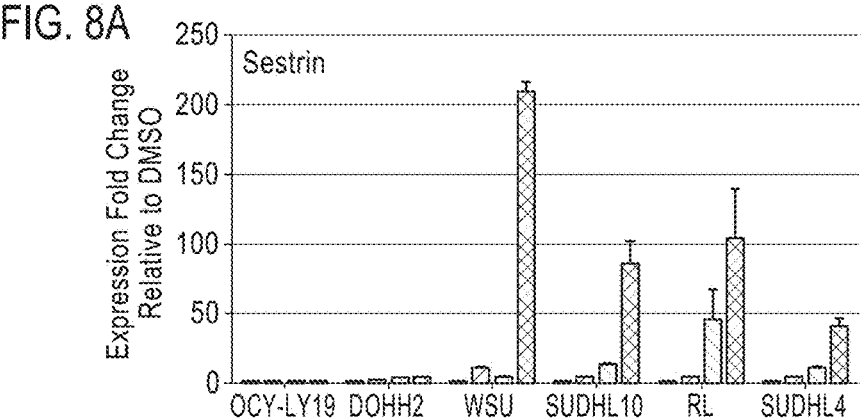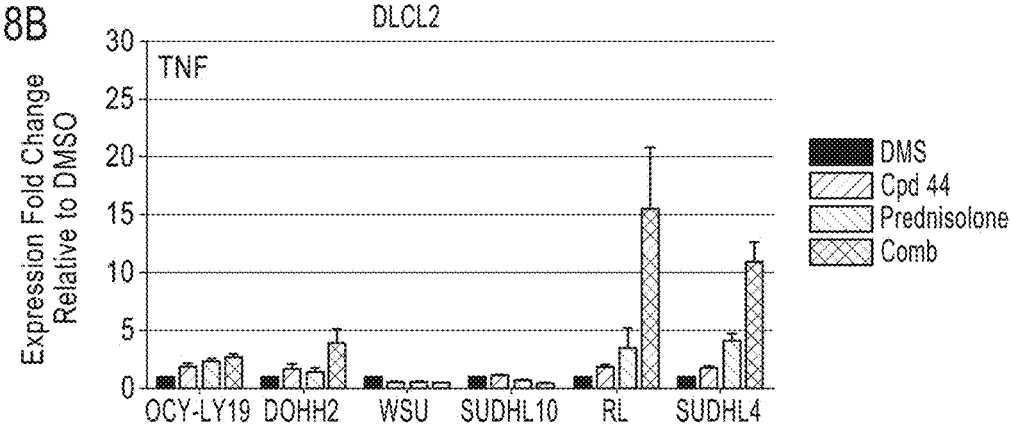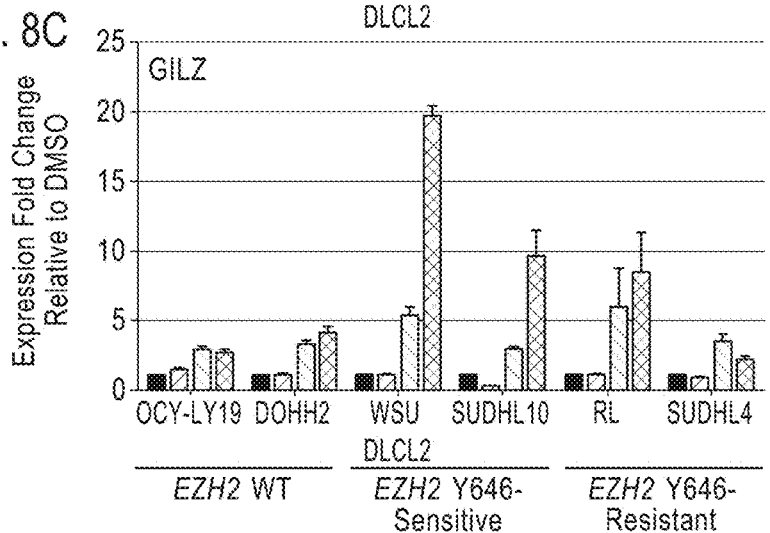

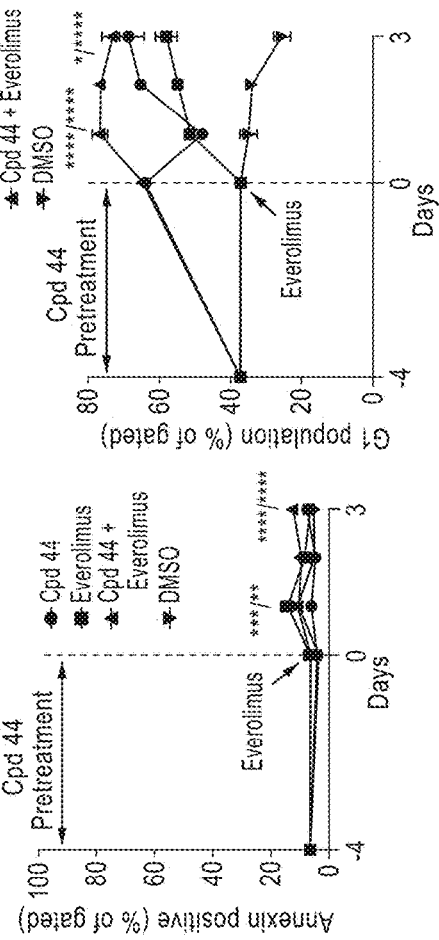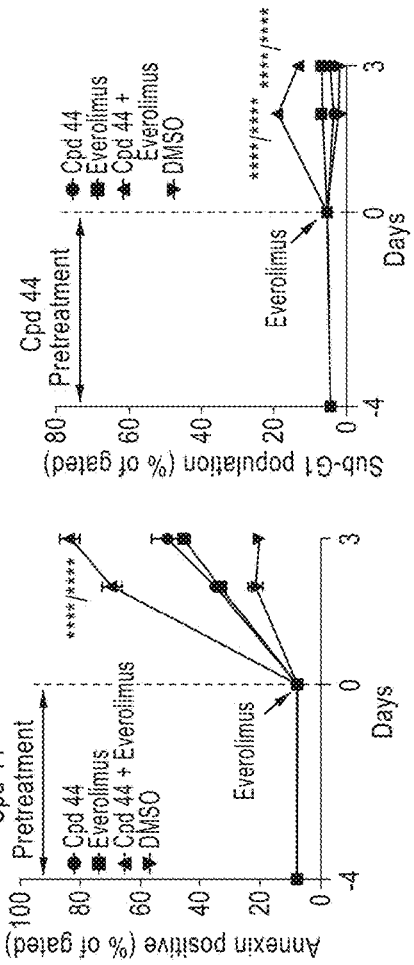
FIG. 11A, FIG. 11B, FIG. 11C, FIG. 11D, FIG. 11E, FIG. 11F

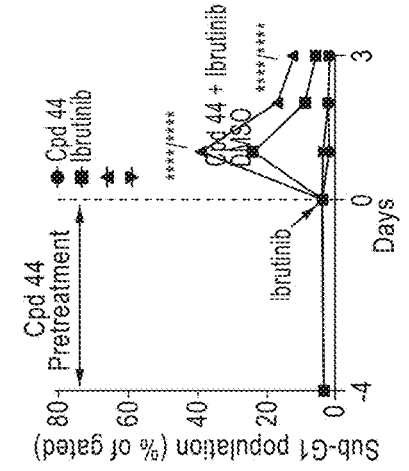
FIG. 12A   FIG. 12B   FIG. 12C
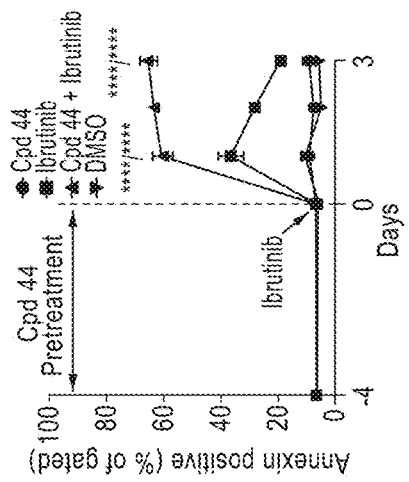
FIG. 12D   FIG. 12E   FIG. 12F
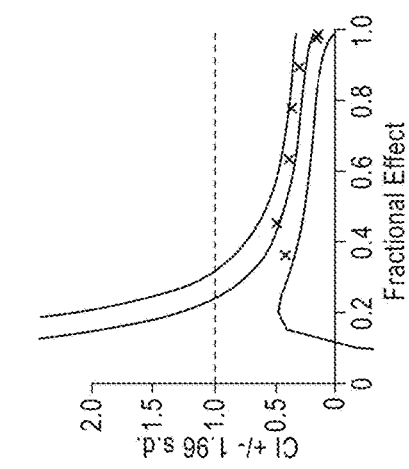

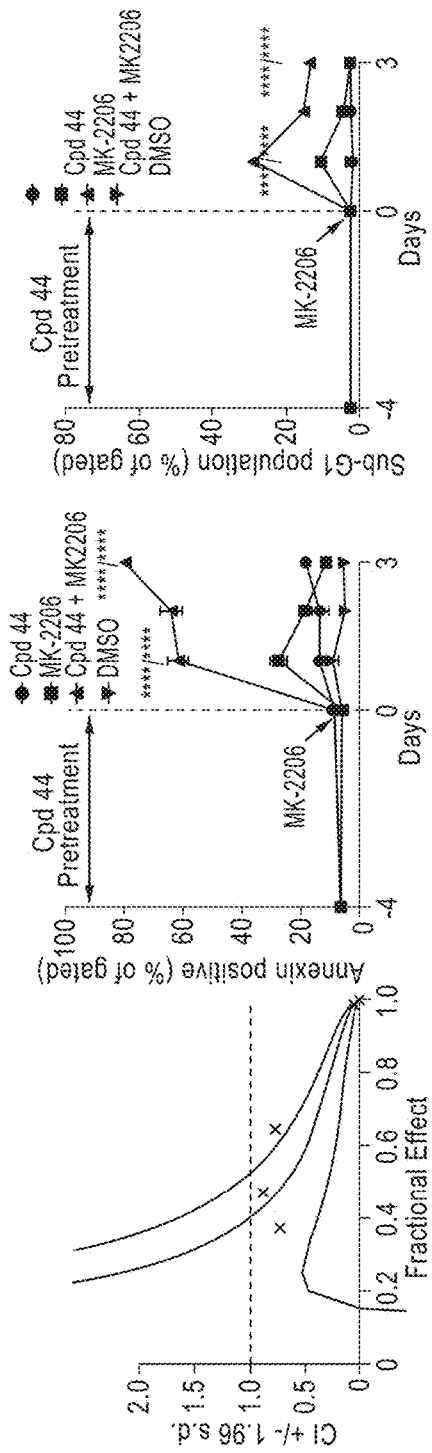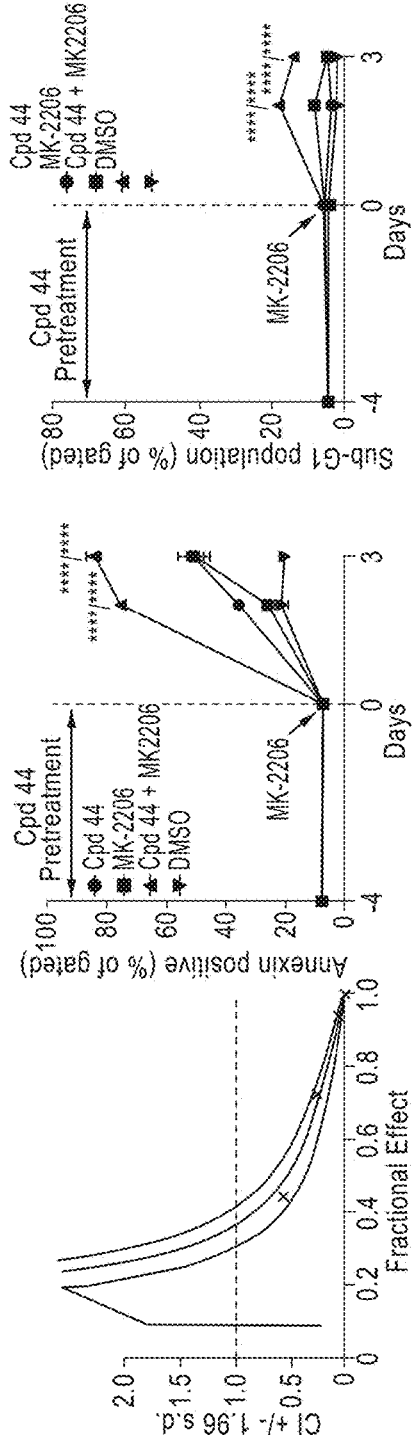
FIG. 13A  FIG. 13B  FIG. 13C
FIG. 13D  FIG. 13E  FIG. 13F

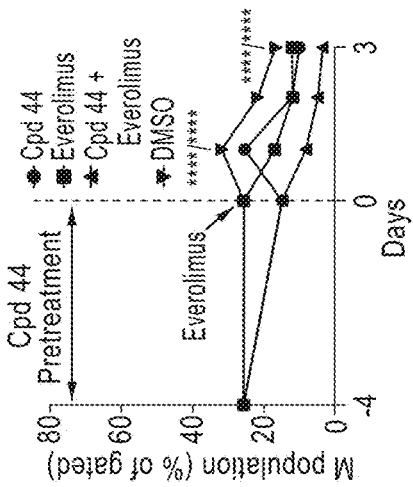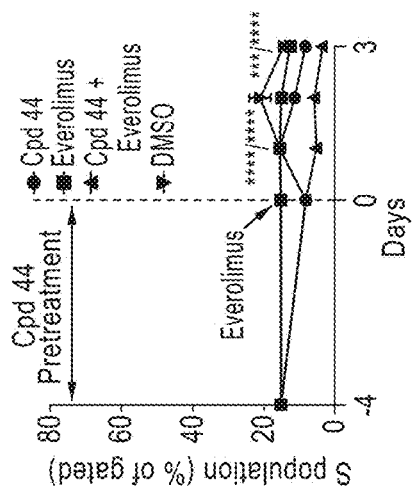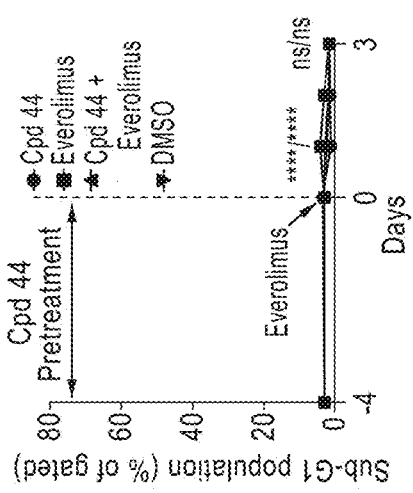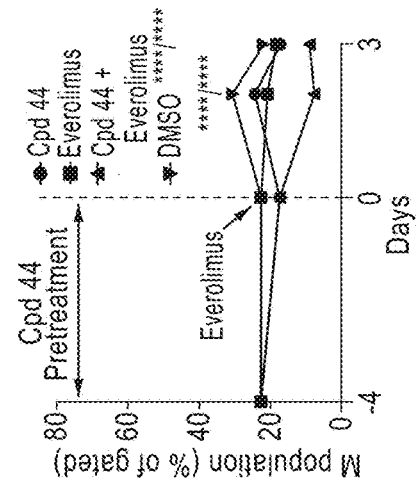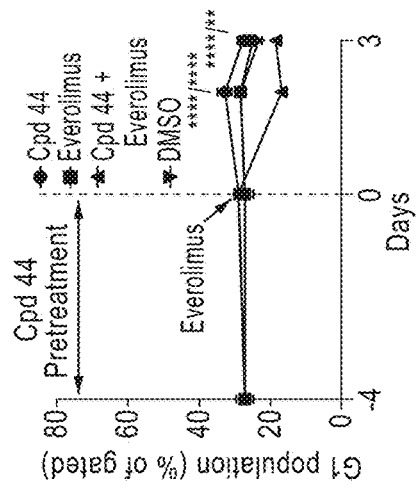
FIG. 16A  FIG. 16B  FIG. 16C  FIG. 16D  FIG. 16E  FIG. 16F

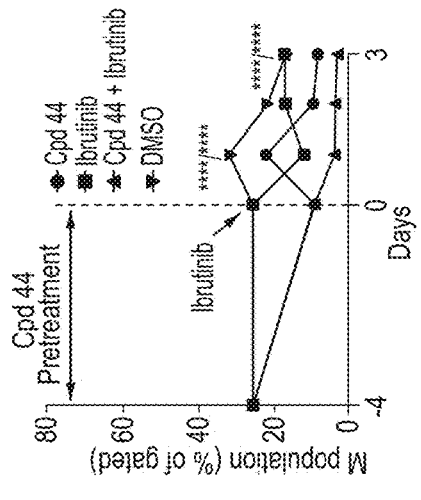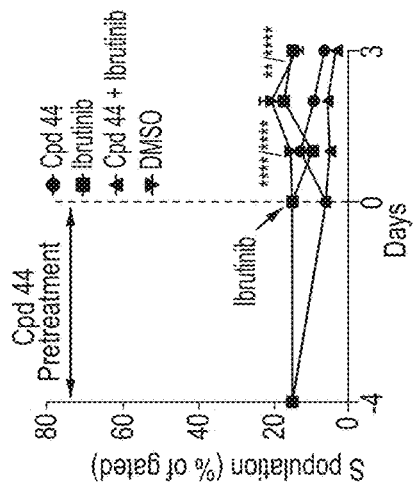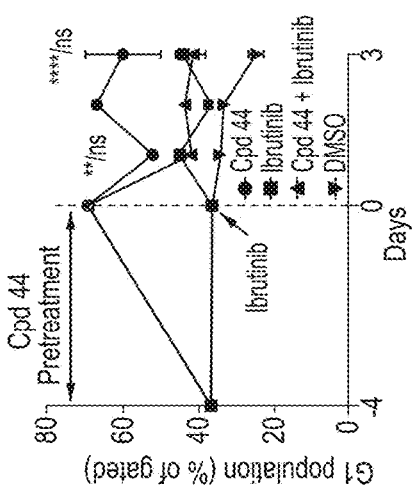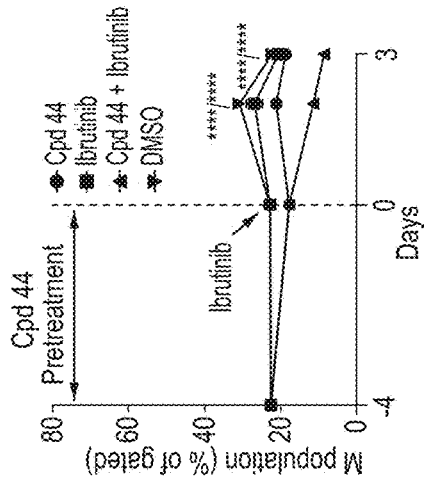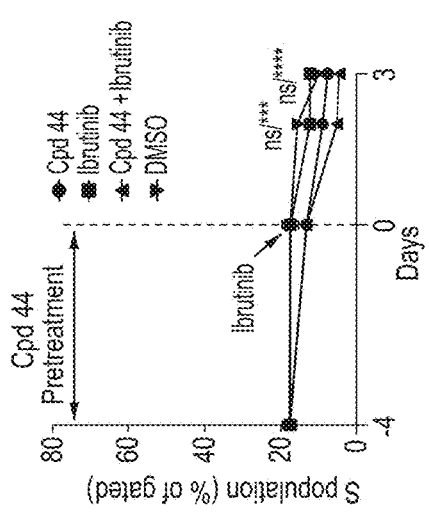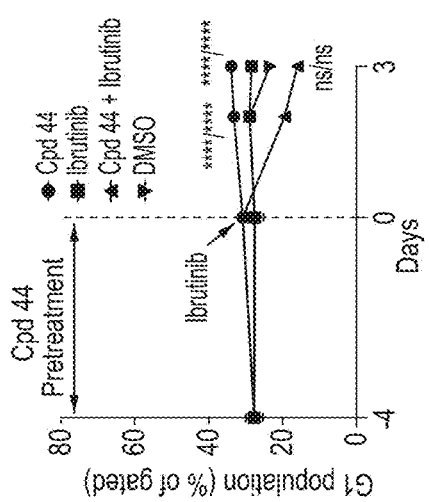

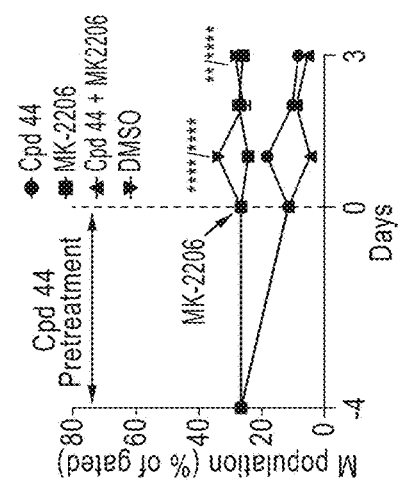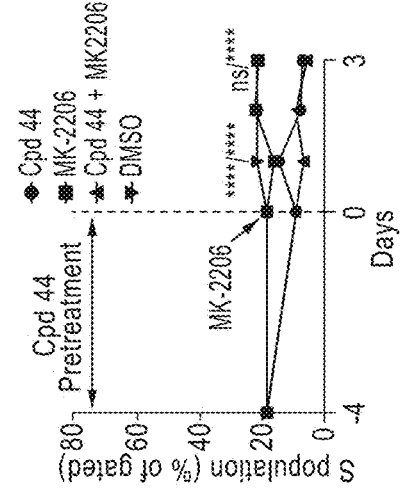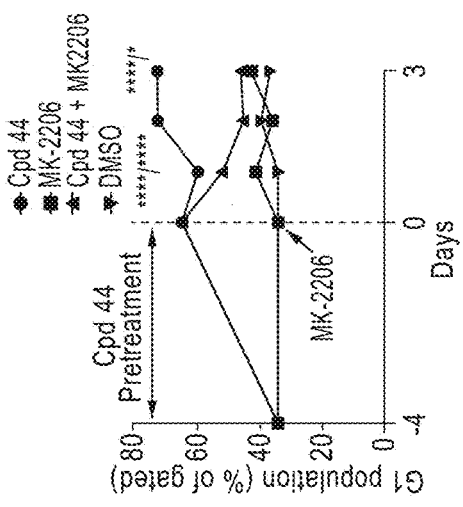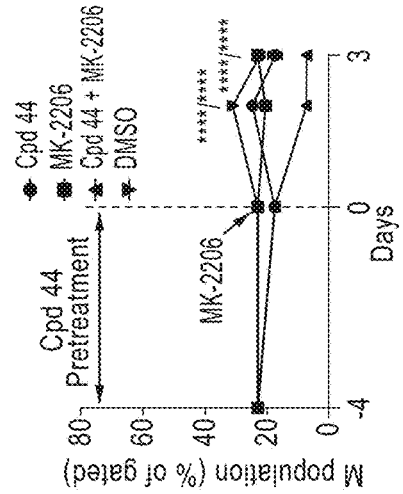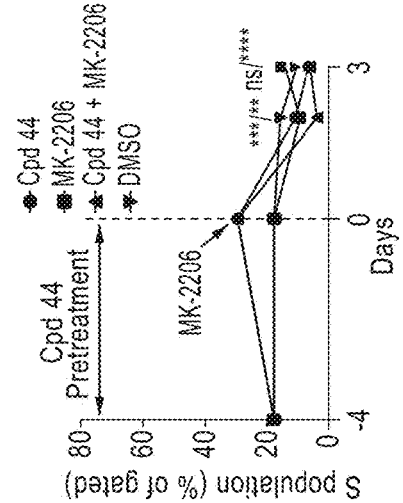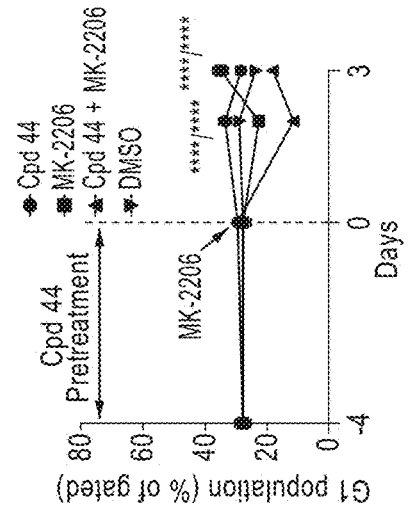

COMBINATION THERAPY FOR TREATING CANCER

RELATED APPLICATIONS

This application is a continuation application of U.S. patent application Ser. No. 15/101,577, filed Jun. 3, 2016, which is a U.S. National Phase application, filed under 35. U.S.C § 371, of International Application No. PCT/US2014/069167, filed Dec. 8, 2014, which claims priority to, and the benefit of, U.S. provisional application Nos. 61/913,063, filed Dec. 6, 2013, 61/934,388, filed Jan. 31, 2014, and 61/992,881, filed May 13, 2014, the contents of each of which are incorporated herein by reference in their entireties.

FIELD OF THE INVENTION

This invention relates to compositions comprising inhibitors of human histone methyltransferase EZH2, the catalytic subunit of the PRC2 complex which catalyzes the mono- through tri-methylation of lysine 27 on histone H3 (H3-K27), and one or more other therapeutic agents, particularly anticancer agents, and methods of combination therapy for treating cancer.

BACKGROUND OF THE INVENTION

Combination-therapy treatments for cancer have become more common, in part due to the perceived advantage of attacking the disease via multiple avenues. Although many effective combination-therapy treatments have been identified over the past few decades; in view of the continuing high number of deaths each year resulting from cancer, a continuing need exists to identify effective therapeutic regimens for use in anticancer treatment.

SUMMARY OF THE INVENTION

The instant invention is based at least in part on the discovery that an EZH2 inhibitor such as Compound 44 (also known as EPZ-6438, E7438)

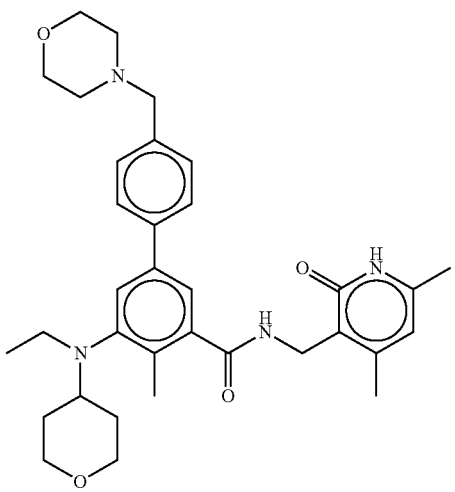

in combination with a variety of agents, including the current standard of care, is very active in the treatment of certain cancers regardless of EZH2 mutation status. In a certain embodiment the cancer is a lymphoma. In a certain embodiment the cancer is a Non-Hodgkin's Lymphoma (NHL) or Diffuse Large B-cell Lymphoma (DLBCL) of germinal center B cell (GCB) origin. In certain embodiments the lymphoma is an EZH2 mutant lymphoma. In certain embodiments the lymphoma is an EZH2 non-mutant or EZH2 wild-type lymphoma. The instant invention is also based upon the discovery that EZH2 inhibitors, such as Compound 44 and glucocorticoid receptor agonists (GRags), such as Prednisone, Prednisolone or Dexamethasone, cooperate to dramatically enhance therapeutic activity in cancer. The combination of Compound 44 and prednisolone extends the range of cells that are sensitive to EZH2 inhibition, from mutant-bearing only to all GCB NHL cells.

In one aspect, the present invention is directed to a method for treating cancer in a patient in need thereof comprising administering a therapeutically effective amount of an EZH2 inhibitor and a therapeutically effective amount of a standard of care agent.

In another aspect, the present invention is directed to a method for treating cancer in a patient in need thereof comprising administering a therapeutically effective amount of a combination comprising an EZH2 inhibitor and a standard of care agent.

Another aspect of the present invention is directed to a method for treating cancer in a patient in need thereof comprising administering a therapeutically effective amount of a composition comprising an EZH2 inhibitor and a standard of care agent.

In some embodiment, the EZH2 mutant lymphoma is an Y646, A682, or A692 mutation.

In some embodiments, the standard of care agent is one or more compounds selected from the group consisting of an R-CHOP component, a BCL inhibitor, and a BCR inhibitor.

In some embodiments, the R-CHOP is a GRag component of CHOP, prednisolone or dexamethasone.

In some embodiments, R-CHOP is a glucocorticosteroid receptor agonist. In certain embodiments, the glucocorticosteroid receptor agonist is prednisolone or dexamethasone.

In some embodiments, doxorubicin is omitted from R-CHOP.

In some embodiments, the BCL inhibitor is navitoclax, obatoclax or ABT-19.

In some embodiments, the BCR inhibitor is rituximab, the AKT inhibitor MK-2206, idelalisib, trametinib, tamatinib, everolimus or ibrutinib.

In some embodiments, the BCR inhibitor is PI3K/Akt/mTOR signaling cascade inhibitor.

In some embodiments, the BCR inhibitor is rituximab, MK-2206, idelalisib, trametinib, tamatinib, everolimus, VELCADE, or ibrutinib.

In some embodiments, the EZH2 inhibitor and the standard of care agent are administered simultaneously or sequentially. In other embodiments, the EZH2 inhibitor is administered prior to administration of the standard of care agent.

In some embodiments, at least one gene is upregulated in the patient. In certain embodiments, the gene that is upregulated is selected from the group consisting of Sestrin, TNF, and GILZ. In other embodiments, the gene the gene that is upregulated is a glucocorticoid target gene.

In some embodiments, the upregulation of a gene is used to determine or adjust the therapeutically effective amount of the EZH2 inhibitor and the standard of care agent.

In another aspect, the present invention is directed to a method of selecting a patient for treatment wherein the patient is selected based on the expression profile of one or more genes selected from the group consisting of Sestrin, TNF and GILZ.

In one aspect, the present invention is directed to a method for treating cancer in a patient in need thereof comprising administering a therapeutically effective amount of an EZH2 inhibitor and a therapeutically effective amount of a standard of care agent wherein the patient has upregulated expression of Sestrin, TNF or GILZ.

In some embodiments, the cancer is an EZH2 inhibitor resistant or refractory cancer.

In some embodiments, the cancer is characterized by increased trimethylation at H3K27.

One aspect of the invention is directed to the combination of the EZH2 inhibitor and the GRag reverses the insensitivity in EZH2-inhibitor resistant or refractory mutant cells, including EZH2 mutation bearing cells.

In certain embodiments, the EZH2 inhibitor is Compound 44, or a pharmaceutically acceptable salt or solvate thereof and one or more other therapeutic agents.

Other features and advantages of the invention will be apparent from the following detailed description and claims.

BRIEF DESCRIPTION OF FIGURES

FIGS. 1A-1F are a series of Fa-CI plots demonstrating combination benefit with CHOP components and Compound 44 (Cpd 44) in mutant EZH2 germinal center B-cell lymphoma cell lines. Compound 44 and doxorubicin act synergistically in the WSU-DLCL2 cells (FIG. 1A) and produce an additive effect in SU-DHL-10 cells (FIG. 1D). Combination benefit is observed with mafosfamide in WSU-DLCL2 cells (FIG. 1C) and SU-DHL-10 cells (FIG. 1F). Combination benefit is also observed with vincristine in both EZH2 Y646 mutant cell lines: WSU-DLCL2 cells (FIG. 1B) and SU-DHL-10 cells (FIG. 1E). In WSU-DLCL2 doses ranged from 0.16-20 nM for doxorubicin, 0.04-5 nM for vincristine, 0.156-10 µM for mafosfamide, and 15-1000 nM for Compound 44. In SU-DHL-10 cells doses ranged from 0.5-60 nM for doxorubicin, 0.016-2 nM for vincristine, 0.156-10 µM for mafosfamide, and 1.56-100 nM for Compound 44. Cells were treated according to pretreatment model A, and data analyzed with the Calcusyn software.

FIGS. 2A-2D are a series of plots demonstrating that glucocorticoid agonists enhance potency of Compound 44 (Cpd 44) in EZH2 mutant lymphoma lines. Potency of Compound 44 is dramatically increased when combined with glucocorticoid agonists. The addition of prednisolone (FIG. 2A, 2C) or dexamethasone (FIG. 2B, 2D) in 2 EZH2 Y646F mutant DLBCL lines according to pre-treatment model A produces a dose dependent shift in the $IC_{50}$ of Compound 44. Doses ranged from 15 nM-1000 nM for prednisolone and 1.5 nM-100 nM for dexamethasone in both cell lines. Doses of Compound 44 ranged from 15-1000 nM in WSU-DLCL2 cells and 1.5-100 nM in SU-DHL-10 cells.

FIGS. 3A-3D are a series of dose response plots demonstrating the benefits of combinations of Compound 44 (Cpd 44) with prednisolone or dexamethasone in WSU-DLCL2 EZH2 mutant (FIG. 3A, 3B) and DOHH2 EZH2 wild-type (FIG. 3C, 3D) GCB lymphoma cell lines, respectively. Doses of Compound 44 ranged from 15.6-1000 nM, doses of prednisolone ranged from 7.8-1000 nM, and doses of dexamethasone ranged from 0.8-100 nM. (FIGS. 3A and 3B). Potency of Compound 44 was increased with prednisolone or dexamethasone in EZH2 mutant WSU-DLCL2 cells (FIGS. 3C and 3D). Compound 44 showed no anti-proliferative effect as a single agent in DOHH2 EZH2 wild-type cells, therefore the potency shift of prednisolone or dexamethasone was measured. The potency of prednisolone or dexamethasone was increased with addition of Compound 44 in DOHH2 cells.

FIG. 4 is a summary table showing that Compound 44 (Cpd 44)/glucocorticoid agonist combination overcomes EZH2 inhibitors (EZH2i) insensitivity in cell lines resistant to EZH2 inhibitors. Overall, a combination of prednisolone and Compound 44 leads to greater sensitivity in all GCB cell lines tested, not just EZH2i sensitive cell lines. Except for RL cells, where sequence of drug addition is crucial as preincubation with prednisolone, followed by Compound 44, is not effective.

FIG. 6 is a summary table of the results from combinations of various drugs and/or drug therapies with Compound 44 (Cpd 44). Combination benefit with Compound 44 was achieved with all drugs tested in EZH2 mutant lymphoma lines. Glucocorticoid agonists demonstrated combination benefit with EZH2 WT and mutant GCB lymphoma lines.

FIGS. 7A-7C are a series of plots demonstrating that Compound 44(Cpd 44)-CHOP combinations show enhanced anti-tumor activity compared to single agents in several EZH2 mutant lymphoma xenograft models. WSU-DLCL2 (EZH2 Y646F) xenografts were treated with Compound 44, CHOP, or the combination for 28 days, as specified in the methods (FIG. 7A). Mean tumor volumes +/−SEM are plotted. Both doses of Compound 44 at 150 mg/kg TID and 225 mg/kg BID were statistically more significant in tumor growth inhibition than vehicle alone (*p value<0.05). Treatment with Compound 44 at 225 mg/kg BID plus CHOP resulted in greater tumor regression than with any single agent alone (***p value<0.001 versus vehicle). Statistics calculated by repeated measures ANOVA. SU-DHL6 (EZH2 Y646N) xenografts were treated with Compound 44, CHOP, or the combination for 28 days, as specified in the methods (FIG. 7B). Mean tumor volumes +/−SEM are plotted in top panel. CHOP or single agent Compound 44 alone had no effect on tumor growth, but treatment with Compound 44 at 225 mg/kg BID plus CHOP resulted in tumor growth regression during the treatment period of 28 days, while also maintaining tumor growth delay after 32 days of dosing cessation (*p value<0.0001). Survival curves (bottom panel) out to 60 days demonstrate significant tumor growth delay in animals treated with a combination of Compound 44 and CHOP (**p value<0.05). Statistics calculated by two-tailed t-test. SUDHL-10 (EZH2 Y646F) xenografts were treated with Compound 44, COP (SOC without the doxorubicin component), or the combination for 28 days, as specified in the methods (FIG. 7C). Mean tumor volumes +/−SEM are plotted in top panel. Percent survival out to 60 days in a tumor growth delay study is plotted in the middle panel (Note: 500 mg/kg and 250 mg/kg+COP survival curves are overlapping). Mean tumor weights are compared in the bottom panel, demonstrating the significant differences in tumor weight between groups (*p value<0.05, p value<0.01, **p value<0.0001).

FIGS. 8A-8C are panels showing the change in expression levels of glucocorticoid target genes Sestrin 1 (SESN1, FIG. 8A), TNF (FIG. 8B) and GILZ (FIG. 8C) when various cell lines are treated with Compound 44, prednisolone, a combination of Compound 44 and prednisolone, or DMSO. As shown in FIGS. 8A-8C, an increase in the expression levels of Sestrin 1, TNF, and GILZ was observed after co-treatment compared to Compound 44 or prednisolone alone.

FIGS. 11A and 11D are Fa-CI plots demonstrating the combination benefit of Compound 44 and everolimus. FIGS. 11B and 11E are panels showing apoptosis in WSU-DLCL2 and SU-DHL-5 cells treated with, Compound 44, everolimus, a combination of Compound 44 and everolimus, or DMSO. FIGS. 11C and 11F are plots showing the changes in the G1 phase of cell cycle observed after co-treatment compared to Compound 44 alone in both WSU-DLCL2 and SU-DHL-5 cells. Strong synergistic effects were observed for a combination of Compound 44 and everolimus in both WSU-DLCL2 cells and SU-DHL-5 (FIG. 11A, 11D).

FIGS. 12A and 12D are Fa-CI plots demonstrating the combination benefit of Compound 44 and ibrutinib. FIGS. 12B and 12E are panels showing apoptosis in WSU-DLCL2 and SU-DHL-5 cells treated with Compound 44, ibrutinib, a combination of Compound 44 and ibrutinib, or DMSO. FIGS. 12C and 12F are plots showing the changes in the G1 phase of cell cycle observed after co-treatment compared to Compound 44 alone in both WSU-DLCL2 and SU-DHL-5 cells. Strong synergistic effects were observed for a combination of Compound 44 and ibrutinib in both WSU-DLCL2 cells and SU-DHL-5 (FIGS. 12A, 12D).

FIGS. 13A, 13D, and 13G are Fa-CI plots demonstrating the combination benefit of Compound 44 and MK-2206 in WSU-DLCL2, SU-DHL-5, and OCI-LY19 cells. FIGS. 13B, 13E, and 13H are panels showing apoptosis in WSU-DLCL2, SU-DHL-5, and OCI-LY19 cells treated with Compound 44, MK-2206, a combination of Compound 44 and MK-2206, or DMSO. FIGS. 13C, 13F, and 13I are plots showing the changes in the G1 phase of cell cycle observed after co-treatment compared to Compound 44 alone in the three cell lines. Strong synergistic effects were observed for a combination of Compound 44 and MK-2206 in WSU-DLCL2 cells, SU-DHL-5, and OCI-LY19 cells (FIGS. 13A, 13D and 13G).

FIGS. 16A and 16D are plots showing the changes in the G1 phase of cell cycle observed after treatment of WSU-DLCL2 and SU-DHL-5 cells with Compound 44, everolimus, a combination of Compound 44 and everolimus, and DMSO. FIGS. 16B and 16E are plots showing the changes in the S phase of cell cycle observed after treatment of WSU-DLCL2 and SU-DHL-5 cells with Compound 44, everolimus, a combination of Compound 44 and everolimus, and DMSO. FIGS. 16C and 16F are plots showing the changes in G2/M phases of the cell cycle observed after treatment of WSU-DLCL2 and SU-DHL-5 cells with Compound 44, everolimus, a combination of Compound 44 and everolimus, and DMSO. Synergistic decrease of cells in G1, S, and G2/M phases of the cell cycle, respectively, is seen 48 hours after co-treatment on SU-DHL-5 cells (FIGS. 16D-16F). No change in sub-G1 phase of the cell cycle was observed when WSU-DLCL2 cells are treated with single agents or in combination (FIG. 16A). Synergistic time-dependent decrease of cells in S phase and G2/M phase of the cell cycle, respectively, was observed when WSU-DLCL2 cells were treated with the combination (FIG. 16B, 16C).

FIGS. 17A and 17D are plots showing the changes in the G1 phase of cell cycle observed after treatment of WSU-DLCL2 and SU-DHL-5 cells with Compound 44, ibrutinib a combination of Compound 44 and ibrutinib and DMSO. FIGS. 17B and 17E are plots showing the changes in the S phase of cell cycle observed after treatment of WSU-DLCL2 and SU-DHL-5 cells with Compound 44, ibrutinib, a combination of Compound 44 and ibrutinib, and DMSO. FIGS. 17C and 17F are plots showing the changes in G2/M phases of the cell cycle observed after treatment of WSU-DLCL2 and SU-DHL-5 cells with Compound 44, ibrutinib, a combination of Compound 44 and ibrutinib, and DMSO. FIGS. 17A-17F show a synergistic decrease of cells in G1, S, and G2/M phases of the cell cycle, respectively, 24 hours after co-treatment of WSU-DLCL2 cells and SU-DHL-5 cells compared to Compound 44 or ibrutinib as single agents.

FIGS. 18A, 18D, and 18G are plots showing the changes in the G1 phase of cell cycle observed after treatment of WSU-DLCL2, SU-DHL-5, and OCI-LY19 cells with Compound 44, MK-2206, a combination of Compound 44 and MK-2206, and DMSO. FIGS. 18B, 18E, and 18H are plots showing the changes in the S phase of cell cycle observed after treatment of WSU-DLCL2, SU-DHL-5, and OCI-LY19 cells with Compound 44, MK-2206, a combination of Compound 44 and MK-2206, and DMSO. FIGS. 18C, 18F, and 18I are plots showing the changes in G2/M phases of the cell cycle observed after treatment of WSU-DLCL2, SU-DHL-5, and OCI-LY19 cells with Compound 44, MK-2206, a combination of Compound 44 and MK-2206, and DMSO. FIGS. 18A-18I show a synergistic decrease of cells in G1, S, and G2/M phases of the cell cycle, respectively after co-treatment of WSU-DLCL2 cells and SU-DHL-5 cells compared to Compound 44 or MK-2206 as single agents.

FIG. 20A is a plot showing the change in tumor weight in SUDHL10 (EZH2 Y646F) xenograft-bearing mice treated with Compound 44, COP (chemotherapy without the Doxorubicin component), or their combination for 28 days. FIG. 20B is a is a plot showing the change in tumor volume in SUDHL10 (EZH2 Y646F) xenograft-bearing mice treated for 28 days with two doses of Compound 44, Prednisone, or their combination. FIG. 20C is a plot showing the change in body weight in SUDHL10 (EZH2 Y646F) xenograft-bearing mice treated with Compound 44, Prednisone, or their combination (See FIG. 20B). Mice dosed with the maximal tolerated dose of Compound 44 or with the Compound 44/COP combination showed 100% survival on day 60, the combination group showed the smallest day 28 tumor weights from all other treatment groups, including the maximal tolerated dose for Compound 44 (FIG. 20A). Prednisone dosing alone did not induce any significant anti-tumor effect (FIG. 20B). In line with the previous study, dosing of Compound 44 generated only a partial response, but co-dosing of Compound 44 with Prednisone, but not with the 2 cycle Prednisone regimen, induced the maximal possible regression achieved with higher doses of Compound 44 alone.

DETAILED DESCRIPTION OF THE INVENTION

Figure 2A:
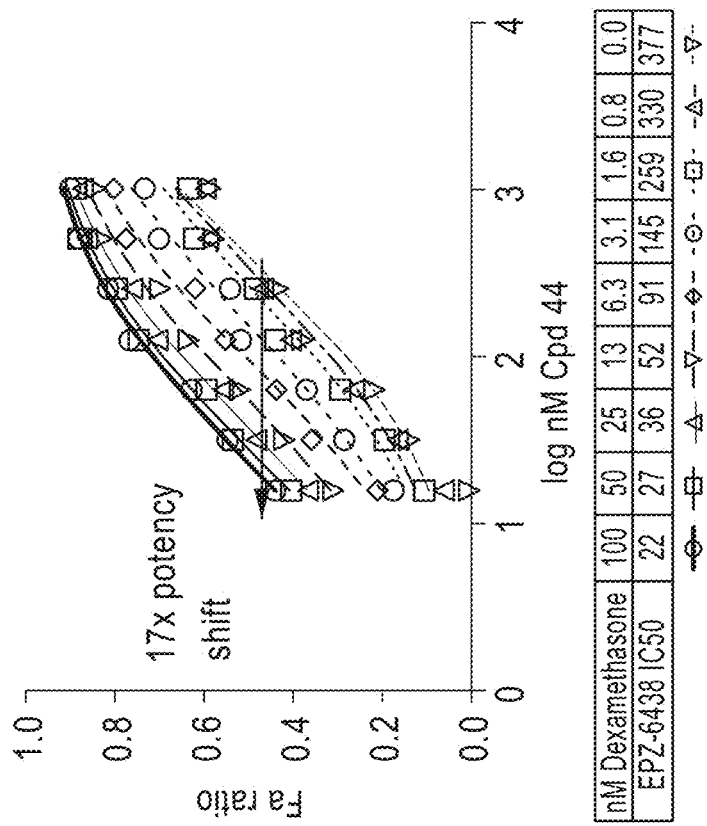

The instant invention is based at least in part on the discovery that Compound 44 in combination with a variety of agents, including the current standard of care, is active in the treatment of certain cancers regardless of EZH2 mutation status. In a certain embodiment the cancer is a lymphoma. In a certain embodiment the cancer is a Non-Hodgkin's Lymphoma (NHL) or Diffuse Large B-cell Lymphoma (DLBCL) of germinal center B cell (GCB) origin. In certain embodiments the lymphoma is an EZH2 mutant lymphoma. In certain embodiments the lymphoma is an EZH2 non-mutant or EZH2 wild-type lymphoma.

In certain aspects of the invention, the EZH2 inhibitor is Compound 44 (also known as EPZ-6438, E7438) having the following formula:

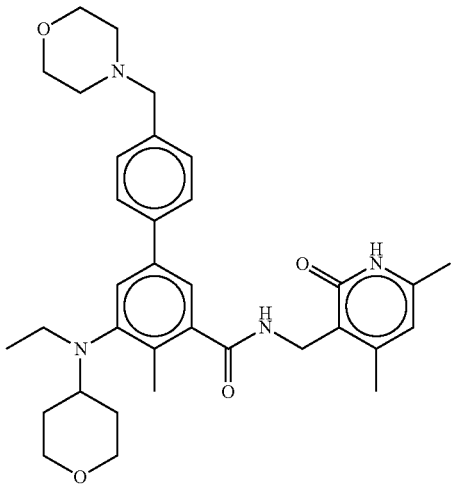

or a pharmaceutically acceptable salt thereof.

The present invention is based upon the discovery that EZH2 histone methyltransferase inhibitors and other anti-cancer agents can be used in combination to treat certain tumors with superior results than those achieved by treating tumors with EZH2 histone methyltransferase inhibitors and the anti-cancer agents alone. Accordingly, the present invention provides a composition comprising an EZH2 histone methyltransferase inhibitor and one or more other therapeutic agents, and methods for their use to treat diseases the course of which can be influenced by modulating the methylation status of histones or other proteins, e.g., cancer. In a certain embodiment, the present invention features a composition comprising Compound 44 and prednisone. The present invention also includes methods for combination therapies comprising EZH2 histone methyltransferase inhibitor and one or more therapeutic agents, such as a Compound 44 and prednisone, to treat cancer, e.g., follicular lymphoma (FL) and diffuse cell large B-cell lymphoma (DCLBL). Specifically, the methods of the present invention are useful for treating or preventing cancer or inhibiting cancer cell proliferation.

An aspect of the present invention relates to methods for treating or alleviating a symptom of cancer or precancerous condition in a subject by administering to a subject expressing a mutant EZH2 a therapeutically effective amount of an EZH2 inhibitor and one or more other therapeutic agents. The mutant EZH2 of the present invention refers to a mutant EZH2 polypeptide or a nucleic acid sequence encoding a mutant EZH2 polypeptide. In certain embodiments the mutant EZH2 comprises one or more mutations in its substrate pocket domain.

Another aspect of the present invention relates to methods for treating or alleviating a symptom of cancer or precancerous condition in a subject by administering to a subject expressing a mutant EZH2 or a wild-type EZH2 a therapeutically effective amount of an EZH2 inhibitor and one or more other therapeutic agents. The mutant EZH2 of the present invention refers to a mutant EZH2 polypeptide or a nucleic acid sequence encoding a mutant EZH2 polypeptide. In certain embodiments the mutant EZH2 comprises one or more mutations in its substrate pocket domain.

In another aspect, the present invention relates to methods for treating or alleviating a symptom of cancer or precancerous condition in a subject by administering to a subject expressing a mutant EZH2 or a wild-type EZH2 a therapeutically effective amount of an EZH2 inhibitor, e.g., Compound 44 and one or more glucocorticoid receptor agonists (GRags), e.g., Prednisone, Prednisolone or Dexamethasone. The mutant EZH2 of the present invention refers to a mutant EZH2 polypeptide or a nucleic acid sequence encoding a mutant EZH2 polypeptide. In certain embodiments the mutant EZH2 comprises one or more mutations in its substrate pocket domain.

Human EZH2 nucleic acids and polypeptides have previously been described. See, e.g., Chen et al. (1996) Genomics 38:30-7 [746 amino acids]; Swiss-Prot Accession No. Q15910 [746 amino acids]; GenBank Accession Nos. NM_004456 and NP_004447 (isoform a [751 amino acids]); and GenBank Accession Nos. NM_152998 and NP_694543 (isoform b [707 amino acids]), each of which is incorporated herein by reference in its entirety.

For purposes of this application, amino acid residue Y641 of human EZH2 is to be understood to refer to the tyrosine residue that is or corresponds to Y641 in Swiss-Prot Accession No. Q15910.

Also for purposes of this application, a Y641 mutant of human EZH2, and, equivalently, a Y641 mutant of EZH2, is to be understood to refer to a human EZH2 in which the amino acid residue corresponding to Y641 of wild-type human EZH2 is substituted by an amino acid residue other than tyrosine.

In certain embodiments the R-CHOP is a GRag component of CHOP, prednisolone or dexamethasone. In certain embodiments the B-cell receptor (BCR) signaling pathways inhibitor is rituximab, the AKT inhibitor MK-2206, idelalisib, trametinib, tamatinib, everolimus or ibrutinib.

The invention is based, in part, on the discovery that inhibitors of the PI3K-AKT-mTOR BCR signaling pathway, e.g., idelalisib, MK-2206 and everolimus, induced very strong synergy in the WSU-DLCL2 and SU-DHL-10 cell lines when combined with Compound 44. The invention is also based, in part, on the discovery that the combination of Compound 44 and inhibitors of the B-cell receptor pathway, e.g., ibrutinib and tamatinib displayed very strong synergy in both mutant cell lines. In certain embodiments, the BCL receptor inhibitor is navoticlax or ABT-199.

In some embodiments, the cancer is a Non-Hodgkin's Lymphoma, Diffuse Large B-cell Lymphoma, or Non-Hodgkin's Lymphoma germinal center B cell.

In some embodiments, the standard of care agent is one or more compounds selected from the group consisting of R-CHOP, a BCL inhibitor, and a BCR inhibitor.

In some embodiments, the R-CHOP is a GRag component of CHOP, prednisolone or dexamethasone.

In some embodiments, the BCR inhibitor is rituximab, the AKT inhibitor MK-2206, idelalisib, trametinib, tamatinib, everolimus or ibrutinib.

In some embodiments, the cancer is an EZH2 mutant cancer.

In some embodiments, the cancer is an EZH2 inhibitor resistant or refractory cancer.

In one embodiment the amino acid sequence of a Y641 mutant of EZH2 differs from the amino acid sequence of wild-type human EZH2 only by substitution of a single amino acid residue corresponding to Y641 of wild-type human EZH2 by an amino acid residue other than tyrosine.

In one embodiment the amino acid sequence of a Y641 mutant of EZH2 differs from the amino acid sequence of wild-type human EZH2 only by substitution of phenylalanine (F) for the single amino acid residue corresponding to Y641 of wild-type human EZH2. The Y641 mutant of EZH2 according to this embodiment is referred to herein as a Y641F mutant or, equivalently, Y641F.

In one embodiment the amino acid sequence of a Y641 mutant of EZH2 differs from the amino acid sequence of wild-type human EZH2 only by substitution of histidine (H) for the single amino acid residue corresponding to Y641 of wild-type human EZH2. The Y641 mutant of EZH2 according to this embodiment is referred to herein as a Y641H mutant or, equivalently, Y641H.

In one embodiment the amino acid sequence of a Y641 mutant of EZH2 differs from the amino acid sequence of wild-type human EZH2 only by substitution of asparagine (N) for the single amino acid residue corresponding to Y641 of wild-type human EZH2. The Y641 mutant of EZH2 according to this embodiment is referred to herein as a Y641N mutant or, equivalently, Y641N.

In one embodiment the amino acid sequence of a Y641 mutant of EZH2 differs from the amino acid sequence of wild-type human EZH2 only by substitution of serine (S) for the single amino acid residue corresponding to Y641 of wild-type human EZH2. The Y641 mutant of EZH2 according to this embodiment is referred to herein as a Y641S mutant or, equivalently, Y641S.

In one embodiment the amino acid sequence of a Y641 mutant of EZH2 differs from the amino acid sequence of wild-type human EZH2 only by substitution of cysteine (C) for the single amino acid residue corresponding to Y641 of wild-type human EZH2. The Y641 mutant of EZH2 according to this embodiment is referred to herein as a Y641C mutant or, equivalently, Y641C.

In one embodiment the amino acid sequence of a A677 mutant of EZH2 differs from the amino acid sequence of wild-type human EZH2 only by substitution of a non-alanine amino acid, preferably glycine (G) for the single amino acid residue corresponding to A677 of wild-type human EZH2. The A677 mutant of EZH2 according to this embodiment is referred to herein as an A677 mutant, and preferably an A677G mutant or, equivalently, A677G. A677 is also referred to as A682.

In one embodiment the amino acid sequence of a A687 mutant of EZH2 differs from the amino acid sequence of wild-type human EZH2 only by substitution of a non-alanine amino acid, preferably valine (V) for the single amino acid residue corresponding to A687 of wild-type human EZH2. The A687 mutant of EZH2 according to this embodiment is referred to herein as an A687 mutant and preferably an A687V mutant or, equivalently, A687V. A687 is also referred to as A692.

In one embodiment the amino acid sequence of a mutant of EZH2 differs from the amino acid sequence of wild-type human EZH2 in one or more amino acid residues in its substrate pocket domain. The mutant of EZH2 according to this embodiment is referred to herein as an EZH2 mutant.

Other exemplary substitution amino acid mutation includes a substitution at amino acid position 677, 687, or 641, such as, but is not limited to a substitution of glycine (G) for the wild type residue alanine (A) at amino acid position 677 (A677G); a substitution of valine (V) for the wild type residue alanine (A) at amino acid position 687 (A687V); a substitution of phenylalanine (F) for the wild type residue tyrosine (Y) at amino acid position 641 (Y641F); a substitution of histidine (H) for the wild type residue tyrosine (Y) at amino acid position 641 (Y641H); a substitution of asparagine (N) for the wild type residue tyrosine (Y) at amino acid position 641 of (Y641N); a substitution of serine (S) for the wild type residue tyrosine (Y) at amino acid position 641 of (Y641S); or a substitution of cysteine (C) for the wild type residue tyrosine (Y) at amino acid position 641 (Y641C). Y641 is also referred to as Y646.

Cells heterozygous for EZH2 would be expected to display a malignant phenotype due to the efficient formation of H3-K27me1 by the WT enzyme and the efficient, subsequent transition of this progenitor species to H3-K27me2, and, especially, H3-K27me3, by the mutant enzyme form(s).

Another aspect of the invention is a method for inhibiting in a subject conversion of H3-K27 to trimethylated H3-K27. The inhibition can involve inhibiting in a subject conversion of unmethylated H3-K27 to monomethylated H3-K27, conversion of monomethylated H3-K27 to dimethylated H3-K27, conversion of dimethylated H3-K27 to trimethylated H3-K27, or any combination thereof, including, for example, conversion of monomethylated H3-K27 to dimethylated H3-K27 and conversion of dimethylated H3-K27 to trimethylated H3-K27. As used herein, unmethylated H3-K27 refers to histone H3 with no methyl group covalently linked to the amino group of lysine 27. As used herein, monomethylated H3-K27 refers to histone H3 with a single methyl group covalently linked to the amino group of lysine 27. Monomethylated H3-K27 is also referred to herein as H3-K27me1. As used herein, dimethylated H3-K27 refers to histone H3 with two methyl groups covalently linked to the amino group of lysine 27. Dimethylated H3-K27 is also referred to herein as H3-K27me2. As used herein, trimethylated H3-K27 refers to histone H3 with three methyl groups covalently linked to the amino group of lysine 27. Trimethylated H3-K27 is also referred to herein as H3-K27me3. A composition of the present invention comprises Compound 44 and one or more other therapeutic agents. The compounds and combinations of the invention are suitable for administration as part of a combination therapy with one or more other therapeutic agents or treatment modality, suitable to be administered together, sequentially, or in alternation. Other compounds suitable for the methods of the invention are described in U.S. Publication 20120264734, the contents of which are hereby incorporated by reference in their entireties.

In certain aspects of the invention an inhibitor of EZH2 "selectively inhibits" histone methyltransferase activity of the mutant EZH2 when it inhibits histone methyltransferase activity of the mutant EZH2 more effectively than it inhibits histone methyltransferase activity of wild-type EZH2. For example, in one embodiment the selective inhibitor has an IC50 for the mutant EZH2 that is at least 40 percent lower than the IC50 for wild-type EZH2. In one embodiment the selective inhibitor has an IC50 for the mutant EZH2 that is at least 50 percent lower than the IC50 for wild-type EZH2. In one embodiment the selective inhibitor has an IC50 for the mutant EZH2 that is at least 60 percent lower than the IC50 for wild-type EZH2. In one embodiment the selective inhibitor has an IC50 for the mutant EZH2 that is at least 70 percent lower than the IC50 for wild-type EZH2. In one embodiment the selective inhibitor has an IC50 for the mutant EZH2 that is at least 80 percent lower than the IC50 for wild-type EZH2. In one embodiment the selective inhibitor has an IC50 for the mutant EZH2 that is at least 90 percent lower than the IC50 for wild-type EZH2.

In certain aspects of the invention the inhibitor inhibits conversion of H3-K27me2 to H3-K27me3. In one embodiment the inhibitor is said to inhibit trimethylation of H3-K27. Since conversion of H3-K27me1 to H3-K27me2 precedes conversion of H3-K27me2 to H3-K27me3, an inhibitor of conversion of H3-K27me1 to H3-K27me2 naturally also inhibits conversion of H3-K27me2 to H3-K27me3, i.e., it inhibits trimethylation of H3-K27. It is also possible to inhibit conversion of H3-K27me2 to H3-K27me3 without inhibition of conversion of H3-K27me1 to H3-K27me2. Inhibition of this type would also result in inhibition of trimethylation of H3-K27, albeit without inhibition of dimethylation of H3-K27.

In one embodiment the inhibitor inhibits conversion of H3-K27me1 to H3-K27me2 and the conversion of H3-K27me2 to H3-K27me3. Such inhibitor may directly inhibit the conversion of H3-K27me1 to H3-K27me2 alone. Alternatively, such inhibitor may directly inhibit both the conversion of H3-K27me1 to H3-K27me2 and the conversion of H3-K27me2 to H3-K27me3.

In certain aspects of the invention, the inhibitor compound inhibits histone methyltransferase activity. Inhibition of histone methyltransferase activity can be detected using any suitable method. The inhibition can be measured, for example, either in terms of rate of histone methyltransferase activity or as product of histone methyltransferase activity. The inhibition is a measurable inhibition compared to a suitable control. In one embodiment, inhibition is at least 10 percent inhibition compared to a suitable control. That is, the rate of enzymatic activity or the amount of product with the inhibitor is less than or equal to 90 percent of the corresponding rate or amount made without the inhibitor. In various other embodiments, inhibition is at least 20, 25, 30, 40, 50, 60, 70, 75, 80, 90, or 95 percent inhibition compared to a suitable control. In one embodiment, inhibition is at least 99 percent inhibition compared to a suitable control. That is, the rate of enzymatic activity or the amount of product with the inhibitor is less than or equal to 1 percent of the corresponding rate or amount made without the inhibitor.

A composition of the present invention comprises an EZH2 inhibitor or Compound 44 or a pharmaceutically acceptable salt thereof, and one or more other therapeutic agents, or a pharmaceutically acceptable salt thereof. The present invention provides for the administration of an EZH2 inhibitor or Compound 44 or a pharmaceutically acceptable salt thereof, and one or more therapeutic agents or a pharmaceutically acceptable salt thereof, as a co-formulation or separate formulations, wherein the administration of formulations is simultaneous, sequential, or in alternation. In certain embodiments, the other therapeutic agents can be an agent that is recognized in the art as being useful to treat the disease or condition being treated by the composition of the present invention. In other embodiment, the other therapeutic agent can be an agent that is not recognized in the art as being useful to treat the disease or condition being treated by the composition of the present invention. In one aspect, the other therapeutic agents can be an agent that imparts a beneficial attribute to the composition of the present invention (e.g., an agent that affects the viscosity of the composition). The beneficial attribute to the composition of the present invention includes, but is not limited to, pharmacokinetic or pharmacodynamic co-action resulting from the combination of an EZH2 inhibitor or Compound 44 and one or more other therapeutic agents. For example, the one or more other therapeutic agents can be anticancer agents or chemotherapeutic agents. For example, the one or more other therapeutic agents can be glucocorticoids. For example, the one or more other therapeutic agents can be selected from prednisone, prednisolone, cyclophosphamide, vincristine, doxorubicin, mafosfamide, cisplatin, AraC, everolimus, decitabine, dexamethasone, or functional analogs, derivatives, prodrugs, and metabolites thereof. In another aspect, the other therapeutic agent can be Prednisone or its active metabolite, Prednisolone.

The therapeutic agents set forth below are for illustrative purposes and not intended to be limiting. The present invention includes at least one other therapeutic agent selected from the lists below. The present invention can include more than one other therapeutic agent, e.g., two, three, four, or five other therapeutic agents such that the composition of the present invention can perform its intended function.

In another embodiment, the other therapeutic agent is a chemotherapeutic agent (also referred to as an anti-neoplastic agent or anti-proliferative agent), selected from the group including an alkylating agent; an antibiotic; an anti-metabolite; a detoxifying agent; an interferon; a polyclonal or monoclonal antibody; an EGFR inhibitor; a HER2 inhibitor; a histone deacetylase inhibitor; a hormone; a mitotic inhibitor; an MTOR inhibitor; a multi-kinase inhibitor; a serine/threonine kinase inhibitor; a tyrosine kinase inhibitors; a VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g., a kinase or a protein methyltransferase), a cytidine analogue drug or any chemotherapeutic, anti-neoplastic or anti-proliferative agent listed in www.cancer.org/docroot/cdg/cdg_0. asp.

The present invention provides methods for combination therapy in which a composition comprising an EZH2 inhibitor or Compound 44 or a pharmaceutically acceptable salt thereof, and one or more other therapeutic agents are administered to a subject in need for treatment of a disease or cancer. The combination therapy can also be administered to cancer cells to inhibit proliferation or induce cell death. In one aspect Compound 44 or a pharmaceutically acceptable salt thereof is administered subsequent to administration of the composition of the present invention comprising Compound 44 or a pharmaceutically acceptable salt thereof, and one or more other therapeutic agents. In one aspect, Compound 44 or a pharmaceutically acceptable salt thereof is administered prior to administration of the composition of the present invention comprising Compound 44 or a pharmaceutically acceptable salt thereof, and one or more other therapeutic agents. In one aspect, Compound 44 or a pharmaceutically acceptable salt thereof is administered subsequent to administration of one or more therapeutic agents, such that the other therapeutic agents are administered either in a single composition or in two or more compositions, e.g. administered simultaneously, sequentially, or in alternation. In one aspect, Compound 44 or a pharmaceutically acceptable salt thereof is administered prior to administration of one or more therapeutic agents, such that the other therapeutic agents are administered either in a single composition or in two or more compositions, e.g. administered simultaneously, sequentially, or in alternation.

In one embodiment, a composition of the present invention includes Compound 44 or a pharmaceutically acceptable salt thereof, and one or more anticancer agents, e.g., CHOP (cyclophosphamide, hydroxydaunorubicin, oncovin, and prednisone or prednisolone) or R-CHOP (rituximab, cyclophosphamide, hydroxydaunorubicin, oncovin, prednisone or prednisolone). In one embodiment, a composition of the present invention includes Compound 44 or a pharmaceutically acceptable salt thereof, and prednisone or prednisolone. Methods of the present invention include the combination therapy of administering a compound of Compound 44 or a pharmaceutically acceptable salt thereof, and anticancer agents, wherein the anticancer agents are CHOP, R-CHOP, prednisone, or prednisolone.

In certain embodiments, "combination comprising an EZH2 inhibitor and a standard of care agent" is intended to embrace administration of therapeutic agents that are not co-formulated.

In certain embodiments, "combination therapy" is intended to embrace administration of these therapeutic agents in a sequential manner, wherein each therapeutic agent is administered at a different time, as well as administration of these therapeutic agents, or at least two of the therapeutic agents concurrently, or in a substantially simultaneous manner. Simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Therapeutic agents may also be administered in alternation.

In certain aspects of the invention, the combination therapies featured in the present invention can result in a synergistic effect in the treatment of a disease or cancer. A "synergistic effect" is defined as where the efficacy of a combination of therapeutic agents is greater than the sum of the effects of any of the agents given alone. A synergistic effect may also be an effect that cannot be achieved by administration of any of the compounds or other therapeutic agents as single agents. The synergistic effect may include, but is not limited to, an effect of treating cancer by reducing tumor size, inhibiting tumor growth, or increasing survival of the subject. The synergistic effect may also include reducing cancer cell viability, inducing cancer cell death, and inhibiting or delaying cancer cell growth.

In certain aspects of the invention "combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

In another aspect, a composition of the present invention, or a pharmaceutically acceptable salt or solvate thereof, may be administered in combination with radiation therapy. Radiation therapy can also be administered in combination with a composition of the present invention and another chemotherapeutic agent described herein as part of a multiple agent therapy.

Combination therapy can be achieved by administering two or more agents, e.g., a Compound 44 and one or more other therapeutic agents, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or 10 weeks of each other. In some cases even longer intervals are possible. While in many cases it is desirable that the two or more agents used in a combination therapy be present in within the patient's body at the same time, this need not be so.

The present invention also provides pharmaceutical compositions comprising Compound 44 or pharmaceutically acceptable salts thereof, and one or more other therapeutic agents disclosed herein, mixed with pharmaceutically suitable carriers or excipient(s) at doses to treat or prevent a disease or condition as described herein. The pharmaceutical compositions of the present invention can also be administered in combination with other therapeutic agents or therapeutic modalities simultaneously, sequentially, or in alternation.

Mixtures of compositions of the present invention can also be administered to the patient as a simple mixture or in suitable formulated pharmaceutical compositions. For example, one aspect of the invention relates to a pharmaceutical composition comprising a therapeutically effective dose of an EZH2 inhibitor or Compound 44, or a pharmaceutically acceptable salt, hydrate, enantiomer or stereoisomer thereof; one or more other therapeutic agents, and a pharmaceutically acceptable diluent or carrier.

A "pharmaceutical composition" is a formulation containing the compounds of the present invention in a form suitable for administration to a subject. Compound 44 and one or more other therapeutic agents described herein each can be formulated individually or in multiple pharmaceutical compositions in any combinations of the active ingredients. Accordingly, one or more administration routes can be properly elected based on the dosage form of each pharmaceutical composition. Alternatively, Compound 44 and one or more other therapeutic agents described herein can be formulated as one pharmaceutical composition.

In one embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the phrase "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A composition of the invention can be administered to a subject in many of the well-known methods currently used for chemotherapeutic treatment. For example, for treatment of cancers, a compound of the invention may be injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

In certain embodiments the therapeutically effective amount of each pharmaceutical agent used in combination will be lower when used in combination in comparison to monotherapy with each agent alone. Such lower therapeutically effective amount could afford for lower toxicity of the therapeutic regimen.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

In therapeutic applications, the dosages of the EZH2 inhibitor compounds described herein, other therapeutic agents described herein, compositions comprising Compound 44 and one or more other therapeutic agents, or the pharmaceutical compositions used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

The composition of the present invention is capable of further forming salts. The composition of the present invention is capable of forming more than one salt per molecule, e.g., mono-, di-, tri-. All of these forms are also contemplated within the scope of the claimed invention.

As used herein, "pharmaceutically acceptable salts" refer to derivatives of the compounds of the present invention wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates), of the same salt.

The composition, or pharmaceutically acceptable salts or solvates thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the invention can be found in *Remington: the Science and Practice of Pharmacy*, $19^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

The present invention provides compositions and methods for treating conditions and diseases the course of which can be influenced by modulating the methylation status of histones or other proteins, wherein said methylation status is mediated at least in part by the activity of EZH2. Modulation of the methylation status of histones can in turn influence the level of expression of target genes activated by methylation, and/or target genes suppressed by methylation. The method includes administering to a subject in need of such treatment, a therapeutically effective amount of a composition of the present invention or a pharmaceutically acceptable salt or solvate thereof, to a subject in need of such treatment.

Based at least on the fact that abnormal histone methylation has been found to be associated with certain cancers and precancerous conditions, a method for treating cancer or a precancerous condition with a mutant EZH2 in a subject comprises administering to the subject in need thereof a therapeutically effective amount of a compound that inhibits methylation. In one embodiment a method for treating cancer or a precancerous condition in a subject comprises administering to the subject in need thereof a therapeutically effective amount of a compound that inhibits conversion of unmethylated H3-K27 to monomethylated H3-K27 (H3-K27me1). In one embodiment a method for treating cancer or a precancerous condition in a subject comprises administering to the subject in need thereof a therapeutically effective amount of a compound that inhibits conversion of monomethylated H3-K27 (H3-K27me1) to dimethylated H3-K27 (H3-K27me2). In one embodiment a method for treating cancer or a precancerous condition in a subject comprises administering to the subject in need thereof a therapeutically effective amount of a compound that inhibits conversion of H3-K27me2 to trimethylated H3-K27 (H3-K27me3). In one embodiment a method for treating cancer or a precancerous condition in a subject comprises administering to the subject in need thereof a therapeutically effective amount of a compound that inhibits both conversion of H3-K27me1 to H3-K27me2 and conversion of H3-K27me2 to H3-K27me3. It is important to note that disease-specific increase in methylation can occur at chromatin in key genomic loci in the absence of a global increase in cellular levels of histone or protein methylation. For example, it is possible for aberrant hypermethylation at key disease-relevant genes to occur against a backdrop of global histone or protein hypomethylation.

Modulators of methylation can be used for modulating cell proliferation, generally. For example, in some cases excessive proliferation may be reduced with agents that decrease methylation, whereas insufficient proliferation may be stimulated with agents that increase methylation. Accordingly, diseases that may be treated include hyperproliferative diseases, such as benign cell growth and malignant cell growth (cancer).

The disorder in which EZH2-mediated protein methylation plays a part can be cancer, a cell proliferative disorder, or a precancerous condition. The present invention further provides the use of a composition of the present invention, or a pharmaceutically acceptable salt or solvate thereof, to a subject in need of such treatment, for the preparation of a medicament useful for the treatment of cancer. Exemplary cancers that may be treated include lymphomas, including non-Hodgkin lymphoma, follicular lymphoma (FL) and diffuse large B-cell lymphoma (DLBCL), including GCB lymphoma.

In general, compounds that are methylation modulators can be used for modulating cell proliferation, generally. For example, in some cases excessive proliferation may be reduced with agents that decrease methylation, whereas insufficient proliferation may be stimulated with agents that increase methylation. Accordingly, diseases that may be treated by the compounds of the invention include hyperproliferative diseases, such as benign cell growth and malignant cell growth.

As used herein, a "subject in need thereof" is a subject having a disorder in which EZH2-mediated protein methylation plays a part, or a subject having an increased risk of developing such disorder relative to the population at large. A subject in need thereof can have a precancerous condition. Preferably, a subject in need thereof has cancer. A "subject" includes a mammal. The mammal can be e.g., any mammal, e.g., a human, primate, bird, mouse, rat, dog, cat, cow, horse, goat, camel, sheep or a pig. Preferably, the mammal is a human.

The subject of the present invention includes any human subject who has been diagnosed with, has symptoms of, or is at risk of developing a cancer or a precancerous condition. The subject of the present invention includes any human subject expressing a mutant EZH2. For example, a mutant EZH2 comprises one or more mutations, wherein the mutation is a substitution, a point mutation, a nonsense mutation, a missense mutation, a deletion, or an insertion or any other EZH2 mutation described herein.

A subject in need thereof may have refractory or resistant cancer. "Refractory or resistant cancer" means cancer that does not respond to treatment. The cancer may be resistant at the beginning of treatment or it may become resistant during treatment. In some embodiments, the subject in need thereof has cancer recurrence following remission on most recent therapy. In some embodiments, the subject in need thereof received and failed all known effective therapies for cancer treatment. In some embodiments, the subject in need thereof received at least one prior therapy. In certain embodiments the prior therapy is monotherapy. In certain embodiments the prior therapy is combination therapy.

In some embodiments, a subject in need thereof may have a secondary cancer as a result of a previous therapy. "Secondary cancer" means cancer that arises due to or as a result from previous carcinogenic therapies, such as chemotherapy.

The subject may also exhibit resistance to EZH2 histone methyltransferase inhibitors or any other therapeutic agent.

The invention also features a method of selecting a combination therapy for a subject having cancer. The method includes the steps of: detecting one or more EZH2 mutations described herein in a sample from the subject; and selecting, based on the presence of the one or more EZH2 mutations, a combination therapy for treating cancer. In one embodiment, the therapy includes administering to the subject a composition of the invention. In one embodiment, the method further includes administrating to the subject a therapeutically effective amount of a composition of the invention. An EZH2 mutation can be detected using any suitable method known in the art. More methods are described in U.S. patent publication US 20130040906, which is incorporated herein by reference in their entireties.

The methods and uses described herein may include steps of detecting one or more EZH2 mutations described herein in a sample from a subject in need thereof prior to and/or after the administration of a composition of the invention (e.g., a composition comprising a Compound 44) or pharmaceutically acceptable salts thereof, and one or more therapeutic agents) to the subject. The presence of the one or more EZH2 mutations described herein in the tested sample indicates the subject is responsive to the combination therapy of the invention.

The present invention provides personalized medicine, treatment and/or cancer management for a subject by genetic screening of one or more EZH2 mutations described herein in the subject. For example, the present invention provides methods for treating or alleviating a symptom of cancer or a precancerous condition in a subject in need thereof by determining responsiveness of the subject to a combination therapy and when the subject is responsive to the combination therapy, administering to the subject a composition of the invention. The responsiveness is determined by obtaining a sample from the subject and detecting one or more EZH2 mutations described herein, and the presence of such one or more EZH2 mutations described herein indicates that the subject is responsive to the composition of the invention. Once the responsiveness of a subject is determined, a therapeutically effective amount of a composition, for example, a composition comprising Compound 44 or pharmaceutically acceptable salts thereof, and one or more therapeutic agents, can be administered. The therapeutically effective amount of a composition can be determined by one of ordinary skill in the art.

As used herein, the term "responsiveness" is interchangeable with terms "responsive", "sensitive", and "sensitivity", and it is meant that a subject is showing therapeutic responses when administered a composition of the invention, e.g., tumor cells or tumor tissues of the subject undergo apoptosis and/or necrosis, and/or display reduced growing, dividing, or proliferation. This term is also meant that a subject will or has a higher probability, relative to the population at large, of showing therapeutic responses when administered a composition of the invention, e.g., tumor cells or tumor tissues of the subject undergo apoptosis and/or necrosis, and/or display reduced growing, dividing, or proliferation.

By "sample" it means any biological sample derived from the subject, includes but is not limited to, cells, tissues samples, body fluids (including, but not limited to, mucus, blood, plasma, serum, urine, saliva, and semen), tumor cells, and tumor tissues. Preferably, the sample is selected from bone marrow, peripheral blood cells, blood, plasma and serum. Samples can be provided by the subject under treatment or testing. Alternatively samples can be obtained by the physician according to routine practice in the art.

As used herein, the term "cell proliferative disorder" refers to conditions in which unregulated or abnormal growth, or both, of cells can lead to the development of an unwanted condition or disease, which may or may not be cancerous. Exemplary cell proliferative disorders of the invention encompass a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue. A cell proliferative disorder includes a precancer or a precancerous condition. A cell proliferative disorder includes cancer. Preferably, the methods provided herein are used to treat or alleviate a symptom of cancer. The term "cancer" includes solid tumors, as well as, hematologic tumors and/or malignancies. A "precancer cell" or "precancerous cell" is a cell manifesting a cell proliferative disorder that is a precancer or a precancerous condition. A "cancer cell" or "cancerous cell" is a cell manifesting a cell proliferative disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through the use of appropriate molecular markers.

A cancer that is to be treated can be evaluated by DNA cytometry, flow cytometry, or image cytometry. A cancer that is to be treated can be typed as having 10%, 20%, 30%, 40%, 50%, 60%, 70%, 80%, or 90% of cells in the synthesis stage of cell division (e.g., in S phase of cell division). A cancer that is to be treated can be typed as having a low S-phase fraction or a high S-phase fraction.

As used herein, a "normal cell" is a cell that cannot be classified as part of a "cell proliferative disorder". A normal cell lacks unregulated or abnormal growth, or both, that can lead to the development of an unwanted condition or disease. Preferably, a normal cell possesses normally functioning cell cycle checkpoint control mechanisms.

As used herein, "contacting a cell" refers to a condition in which a compound or other composition of matter is in direct contact with a cell, or is close enough to induce a desired biological effect in a cell.

As used herein, "candidate compound" refers to a compound of the present invention, or a pharmaceutically acceptable salt or solvate thereof, that has been or will be tested in one or more in vitro or in vivo biological assays, in order to determine if that compound is likely to elicit a desired biological or medical response in a cell, tissue, system, animal or human that is being sought by a researcher or clinician. A candidate compound is a compound of the present invention, or a pharmaceutically acceptable salt or solvate thereof. The biological or medical response can be the treatment of cancer. The biological or medical response can be treatment or prevention of a cell proliferative disorder. In vitro or in vivo biological assays can include, but are not limited to, enzymatic activity assays, electrophoretic mobility shift assays, reporter gene assays, in vitro cell viability assays, and the assays described herein.

As used herein, "treating" or "treat" describes the management and care of a patient for the purpose of combating a disease, condition, or disorder and includes the administration of a compound of the present invention, or a pharmaceutically acceptable salt or solvate thereof, to alleviate the symptoms or complications of a disease, condition or disorder, or to eliminate the disease, condition or disorder.

A composition of the present invention, or a pharmaceutically acceptable salt or solvate thereof, can also be used to prevent a disease, condition or disorder. As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of pharmaceutical compositions of the invention leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

As used herein, the term "severity" is meant to describe the potential of cancer to transform from a precancerous, or benign, state into a malignant state. Alternatively, or in addition, severity is meant to describe a cancer stage, for example, according to the TNM system (accepted by the International Union Against Cancer (UICC) and the American Joint Committee on Cancer (AJCC)) or by other art-recognized methods. Cancer stage refers to the extent or severity of the cancer, based on factors such as the location of the primary tumor, tumor size, number of tumors, and lymph node involvement (spread of cancer into lymph nodes). Alternatively, or in addition, severity is meant to describe the tumor grade by art-recognized methods (see, National Cancer Institute, www.cancer.gov). Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade vary with each type of cancer. Severity also describes a histologic grade, also called differentiation, which refers to how much the tumor cells resemble normal cells of the same tissue type (see, National Cancer Institute, www.cancer.gov). Furthermore, severity describes a nuclear grade, which refers to the size and shape of the nucleus in tumor cells and the percentage of tumor cells that are dividing (see, National Cancer Institute, www-.cancer.gov).

In another aspect of the invention, severity describes the degree to which a tumor has secreted growth factors, degraded the extracellular matrix, become vascularized, lost adhesion to juxtaposed tissues, or metastasized. Moreover, severity describes the number of locations to which a primary tumor has metastasized. Finally, severity includes the difficulty of treating tumors of varying types and locations. For example, inoperable tumors, those cancers which have greater access to multiple body systems (hematological and immunological tumors), and those which are the most resistant to traditional treatments are considered most severe. In these situations, prolonging the life expectancy of the subject and/or reducing pain, decreasing the proportion of cancerous cells or restricting cells to one system, and improving cancer stage/tumor grade/histological grade/nuclear grade are considered alleviating a sign or symptom of the cancer.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. But signs are defined as things that can be seen by a doctor, nurse, or other health care professional.

Cancer is a group of diseases that may cause almost any sign or symptom. The signs and symptoms will depend on where the cancer is, the size of the cancer, and how much it affects the nearby organs or structures. If a cancer spreads (metastasizes), then symptoms may appear in different parts of the body.

Treating cancer can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer can result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer can result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in increase in average survival time of a population of treated subjects in comparison to a population receiving monotherapy with a drug that is not a compound of the present invention, or a pharmaceutically acceptable salt or solvate thereof. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound of the present invention, or a pharmaceutically acceptable salt or solvate thereof. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer can result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer can result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder can result in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder can result in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells can be equivalent to the mitotic index.

Treating or preventing a cell proliferative disorder can result in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder can result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

As used herein, the term "selectively" means tending to occur at a higher frequency in one population than in another population. The compared populations can be cell populations. Preferably, a compound of the present invention, or a pharmaceutically acceptable salt or solvate thereof, acts selectively on a cancer or precancerous cell but not on a normal cell. Preferably, a compound of the present invention, or a pharmaceutically acceptable salt or solvate thereof, acts selectively to modulate one molecular target (e.g., a target protein methyltransferase) but does not significantly modulate another molecular target (e.g., a non-target protein methyltransferase). The invention also provides a method for selectively inhibiting the activity of an enzyme, such as a protein methyltransferase. Preferably, an event occurs selectively in population A relative to population B if it occurs greater than two times more frequently in population A as compared to population B. An event occurs selectively if it occurs greater than five times more frequently in population A. An event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in cancer cells if it occurred greater than twice as frequently in cancer cells as compared to normal cells.

A composition of the present invention, e.g., Compound 44 or pharmaceutically acceptable salt thereof, and one or more other therapeutic agents, such as prednisone, can modulate the activity of a molecular target (e.g., a target protein methyltransferase). Modulating refers to stimulating or inhibiting an activity of a molecular target. Preferably, a compound of the present invention, or a pharmaceutically acceptable salt or solvate thereof, modulates the activity of a molecular target if it stimulates or inhibits the activity of the molecular target by at least 2-fold relative to the activity of the molecular target under the same conditions but lacking only the presence of said compound. More preferably, a compound of the present invention, or a pharmaceutically acceptable salt or solvate thereof, modulates the activity of a molecular target if it stimulates or inhibits the activity of the molecular target by at least 5-fold, at least 10-fold, at least 20-fold, at least 50-fold, at least 100-fold relative to the activity of the molecular target under the same conditions but lacking only the presence of said compound. The activity of a molecular target may be measured by any reproducible means. The activity of a molecular target may be measured in vitro or in vivo. For example, the activity of a molecular target may be measured in vitro by an enzymatic activity assay or a DNA binding assay, or the activity of a molecular target may be measured in vivo by assaying for expression of a reporter gene.

A composition of the present invention does not significantly modulate the activity of a molecular target if the addition of the compound does not stimulate or inhibit the activity of the molecular target by greater than 10% relative to the activity of the molecular target under the same conditions but lacking only the presence of said compound.

As used herein, the term "isozyme selective" means preferential inhibition or stimulation of a first isoform of an enzyme in comparison to a second isoform of an enzyme (e.g., preferential inhibition or stimulation of a protein methyltransferase isozyme alpha in comparison to a protein methyltransferase isozyme beta). Preferably, a compound of the present invention, or a pharmaceutically acceptable salt or solvate thereof, demonstrates a minimum of a fourfold differential, preferably a tenfold differential, more preferably a fifty fold differential, in the dosage required to achieve a biological effect. Preferably, a compound of the present invention, or a pharmaceutically acceptable salt or solvate thereof, demonstrates this differential across the range of inhibition, and the differential is exemplified at the $IC_{50}$, i.e., a 50% inhibition, for a molecular target of interest.

Administering a composition of the present invention to a cell or a subject in need thereof can result in modulation (i.e., stimulation or inhibition) of an activity of a protein methyltransferase of interest.

Administering a compound of the present invention, e.g., a composition comprising Compound 44 or pharmaceutically acceptable salt thereof, and one or more other therapeutic agents, such as prednisone, to a cell or a subject in need thereof results in modulation (i.e., stimulation or inhibition) of an activity of an intracellular target (e.g., substrate). Several intracellular targets can be modulated with the compounds of the present invention, including, but not limited to, protein methyltransferase.

Activating refers to placing a composition of matter (e.g., protein or nucleic acid) in a state suitable for carrying out a desired biological function. A composition of matter capable of being activated also has an unactivated state. An activated composition of matter may have an inhibitory or stimulatory biological function, or both. Elevation refers to an increase in a desired biological activity of a composition of matter (e.g., a protein or a nucleic acid). Elevation may occur through an increase in concentration of a composition of matter.

As used herein, "a cell cycle checkpoint pathway" refers to a biochemical pathway that is involved in modulation of a cell cycle checkpoint. A cell cycle checkpoint pathway may have stimulatory or inhibitory effects, or both, on one or more functions comprising a cell cycle checkpoint. A cell cycle checkpoint pathway is comprised of at least two compositions of matter, preferably proteins, both of which contribute to modulation of a cell cycle checkpoint. A cell cycle checkpoint pathway may be activated through an activation of one or more members of the cell cycle checkpoint pathway. Preferably, a cell cycle checkpoint pathway is a biochemical signaling pathway.

As used herein, "cell cycle checkpoint regulator" refers to a composition of matter that can function, at least in part, in modulation of a cell cycle checkpoint. A cell cycle checkpoint regulator may have stimulatory or inhibitory effects, or both, on one or more functions comprising a cell cycle checkpoint. A cell cycle checkpoint regulator can be a protein or not a protein.

Treating cancer or a cell proliferative disorder can result in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. A number of cells in a population can be measured by fluorescence activated cell sorting (FACS), immunofluorescence microscopy and light microscopy. Methods of measuring cell death are as shown in Li et al., *Proc. Natl. Acad. Sci. USA.* 100(5): 2674-8, 2003. In an aspect, cell death occurs by apoptosis.

Preferably, an effective amount of a composition of the present invention, or a pharmaceutically acceptable salt or solvate thereof, is not significantly cytotoxic to normal cells. A therapeutically effective amount of a compound is not significantly cytotoxic to normal cells if administration of the compound in a therapeutically effective amount does not induce cell death in greater than 10% of normal cells. A therapeutically effective amount of a compound does not significantly affect the viability of normal cells if administration of the compound in a therapeutically effective amount does not induce cell death in greater than 10% of normal cells. In an aspect, cell death occurs by apoptosis.

Contacting a cell with a composition of the present invention, or a pharmaceutically acceptable salt or solvate thereof, can induce or activate cell death selectively in cancer cells. Administering to a subject in need thereof a compound of the present invention, or a pharmaceutically acceptable salt or solvate thereof, can induce or activate cell death selectively in cancer cells. Contacting a cell with a composition of the present invention, or a pharmaceutically acceptable salt or solvate thereof, can induce cell death selectively in one or more cells affected by a cell proliferative disorder. Preferably, administering to a subject in need thereof a composition of the present invention, or a pharmaceutically acceptable salt or solvate thereof, induces cell death selectively in one or more cells affected by a cell proliferative disorder.

The present invention relates to a method of treating or preventing cancer by administering a composition of the present invention, or a pharmaceutically acceptable salt or solvate thereof, to a subject in need thereof, where administration of the composition of the present invention, or a pharmaceutically acceptable salt or solvate thereof, results in one or more of the following: prevention of cancer cell proliferation by accumulation of cells in one or more phases of the cell cycle (e.g. G1, G1/S, G2/M), or induction of cell senescence, or promotion of tumor cell differentiation; promotion of cell death in cancer cells via cytotoxicity, necrosis or apoptosis, without a significant amount of cell death in normal cells, antitumor activity in animals with a therapeutic index of at least 2. As used herein, "therapeutic index" is the maximum tolerated dose divided by the efficacious dose.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* (3$^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., 18$^{th}$ edition (1990). These texts can, of course, also be referred to in making or using an aspect of the invention.

EXAMPLE 1

Synergistic Anti-Tumor Activity of EZH2 Inhibitors and Glucocorticoid

Compound 44 was synthesized as described in U.S. Pat. No. 8,410,088 which is incorporated herein by reference in its entirety.

Dramatic synergy was observed when Compound 44 (Cpd 44) is combined just with the glucocorticoid receptor agonist (GRag) prednisolone of CHOP or with other GRag, such as dexamethasone. When combined with CHOP, the antiproliferative effects of Compound 44 were greatly enhanced and most of this synergy can be ascribed to the GRag component of CHOP, prednisolone (the active metabolite of prednisone). Remarkably, the combination of Compound 44 and prednisolone extends the range of cells that are sensitive to EZH2 inhibition, from mutant-bearing only to all GCB NHL cells.

Two EZH2 mutant cell lines, WSU-DLCL2 and SU-DHL10, were pre-treated with Compound 44 for 4 days and then co-treated with the combination of Compound 44 plus individual CHOP components for 3 additional days (4+3 model). Mafosfamide (an analog of cyclophosphamide), doxorubicin, and vincristine, all showed concentration-dependent growth inhibition in the mutant cell lines by themselves. Hence, combination indices (CI, calculated using Calcusyn software) were obtained for these drugs in combination with Compound 44. These cell lines, however, showed no sensitivity to prednisolone (the active metabolite of prednisone) by itself. Thus, in this case a CI could not be determined and instead an enhancement of potency was calculated based on the shift in IC$_{50}$ of Compound 44 seen with a concentration-response curve of prednisolone.

Figure 2B:
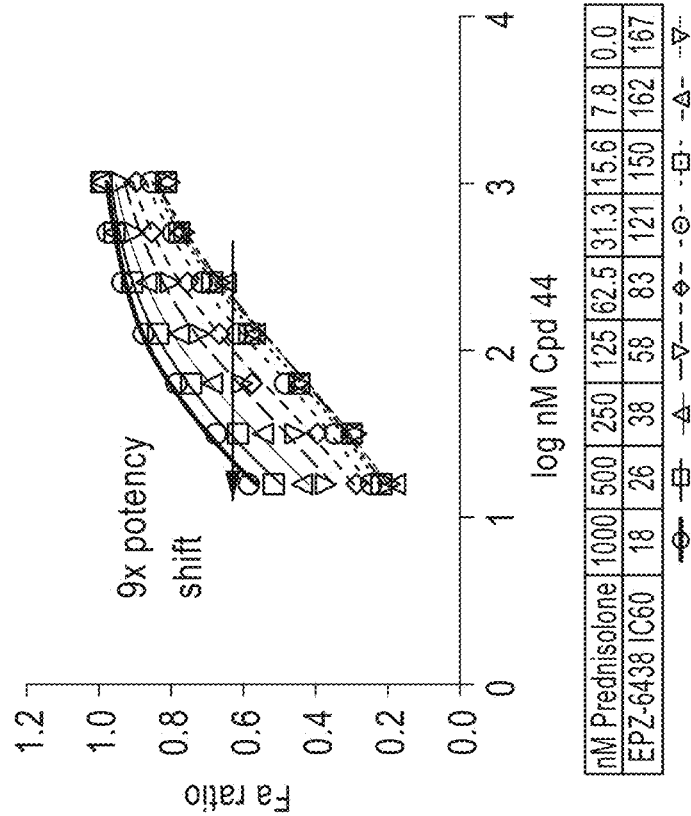

The combination of Compound 44 and mafosfamide led to an overall additive combination benefit in both EZH2 mutant cell lines (FIG. 1C, 1F). In WSU-DLCL2 cells, the combination of Compound 44 and doxorubicin acted synergistically in the 4+3 model (FIG. 1A), while this combination was additive in SU-DHL10 cells (FIG. 1D). The combination of Compound 44 and vincristine also demonstrated additivity in both EZH2 mutant cell lines (FIG. 1B, 1E). When WSU-DLCL2 cells were treated with the combination of prednisolone and Compound 44, a 9-fold shift to greater potency was observed for Compound 44. Treatment with a different GRag, dexamethasone, resulted in an even greater shift in the IC$_{50}$ of Compound 44 of 17-fold (FIG. 2A, 2B). A similar trend in potency shift for Compound 44 was observed in SU-DHL10 cells (FIG. 2C, 2D).

Whether the combination effect of Compound 44 and CHOP could render WT EZH2 lymphoma cell lines, sensitive to Compound 44 was investigated. Since Compound 44 treatment alone does not induce growth inhibition in EZH2 WT lymphoma lines, shifts in potency were calculated based on the concentration-response curves of the individual CHOP components. Of the four CHOP components tested, only the combination of GRag and Compound 44 led to a potency shift in a WT GCB lymphoma cell line.

Figure 3B:
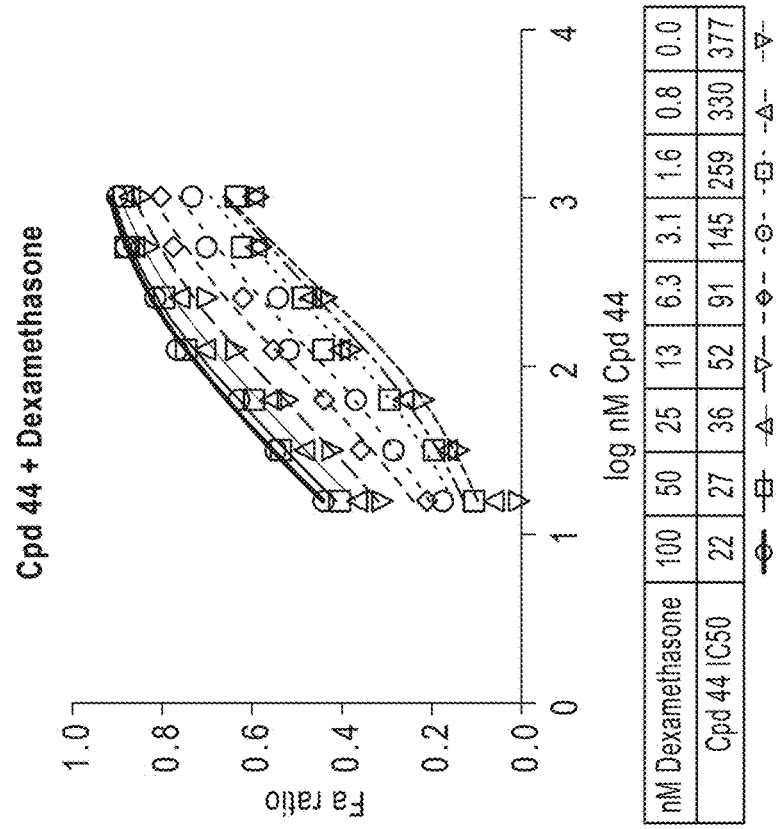
Figure 3A:
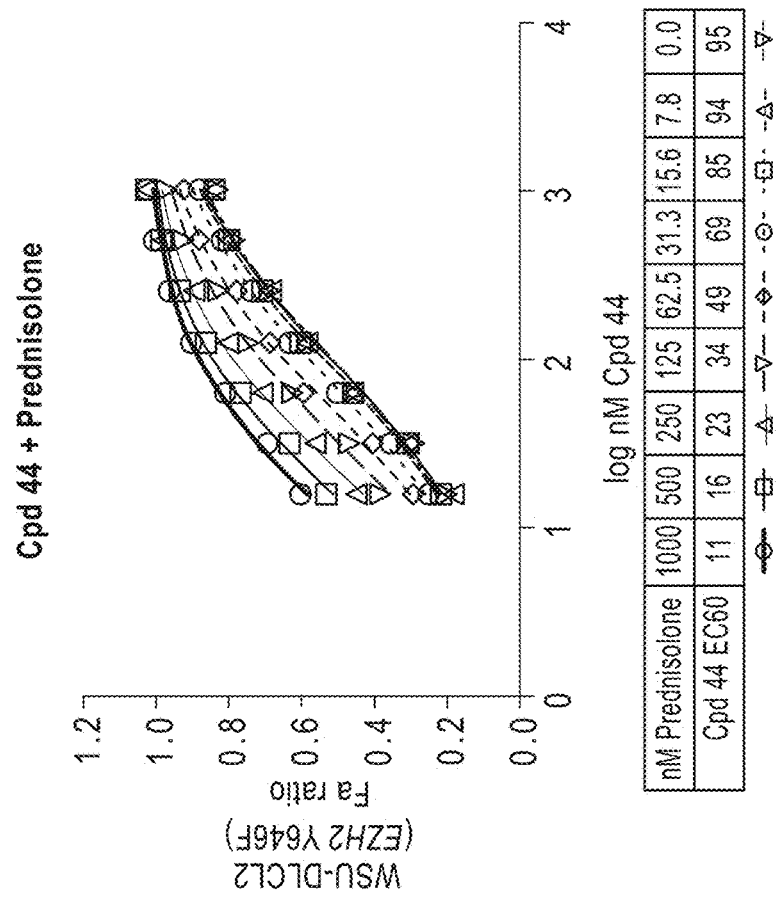
Figure 5B:
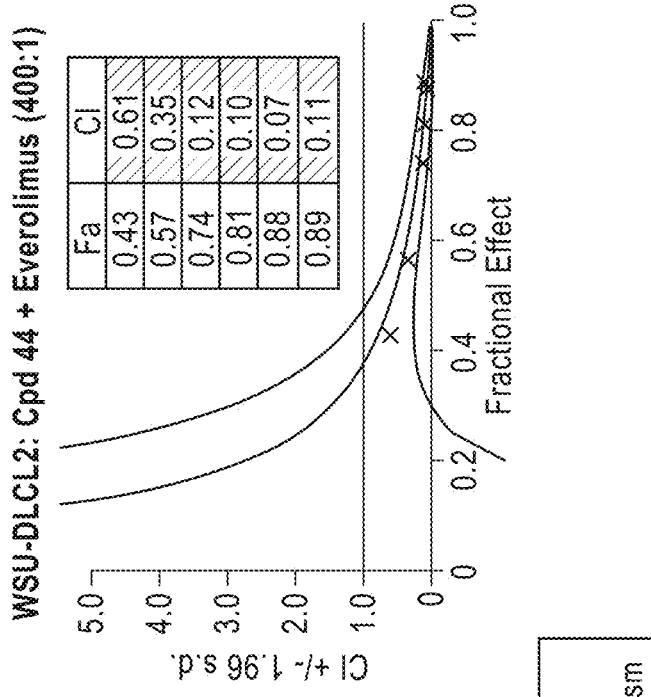
FIGS. 5A and 5B are two plots showing the very strong synergy observed in the EZH2 mutant lymphoma cell line with the combination of Compound 44 (Cpd 44) and other targeted therapies. Very strong synergy is observed when Compound 44 is combined with the BCL2 inhibitor navitoclax (in FIG. 5A), as well as with the mTOR inhibitor everolimus (in FIG. 5B). Dose ranges for navitoclax are 0.16-10 0.04-5 nM for everolimus, and 31-2000 nM for Compound 44. These data were generated in the pretreatment model A and data analyzed with Calcusyn software.
Figure 5A:
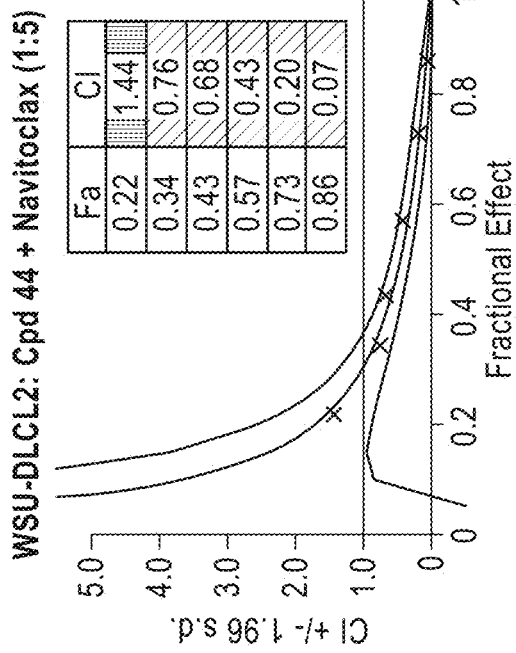

Whether the combination effect of Compound 44 and CHOP could render EZH2 mutant and wild-type cell lines, WSU-DLCL2 EZH2 mutant (FIG. 3A, 3B) and DOHH2 EZH2 wild-type (FIG. 3C, 3D) GCB lymphoma cell lines, sensitive to Compound 44 was investigated next. Treatment of WSU-DLCL2 cells with a combination of Prednisolone and Compound 44 caused an enhancement of Compound 44 activity (FIG. 3A), with a maximum 24-fold reduction in Compound 44 IC$_{50}$. Treatment with a different GRag, Dexamethasone, resulted in an even greater 30-fold reduction in the IC$_{50}$ of Compound 44 (FIG. 3B). At biologically relevant concentrations of 1 µM for Prednisolone and 100 nM for Dexamethasone the potency enhancements were 7 and 15-fold, respectively. Compound 44 showed no anti-proliferative effect as a single agent in DOHH2 EZH2 wild-type cells (FIG. 3C, 3D), therefore the potency shift of Prednisolone or Dexamethasone was measured. Interestingly, when compound 44 was tested in a wild-type GCB lymphoma cell line (DOHH2), only the GRag component of CHOP demonstrated enhanced potency in the presence of Compound 44 (FIG. 3C, 3D). The potency of Prednisolone or Dexamethasone was increased with addition of Compound 44 in DOHH2 cells (FIG. 3C, 3D).

Given that only the GRag and EZH2i combination induced dramatically enhanced antiproliferative effects, compared to either single agent, in EZH2 WT and mutant GCB lymphoma cell lines, whether duration of treatment and/or sequence of addition of compounds affected sensitivity was determined. The cell line panel was also extended to include EZH2 WT, EZH2 mutant, Compound 44 sensitive, and EZH2 mutant, Compound 44 insensitive cell line (previously reported by McCabe et al, and unpublished internal data). In the previous 4+3 model, the potency shift was based on either Compound 44 (in EZH2 Y646 (also known as Y641) sensitive cell lines) or prednisolone (in EZH2 WT cell lines) exposure. For this set of experiments, the Compound 44 IC$_{50}$ shift at a fixed concentration of prednisolone was used to determine the combination benefit in cell lines treated with either the 4+3 model, 4 day or 7 day co-treatment, or 4 day prednisolone pre-treatment plus 3 days of co-treatment. When EZH2 mutant, Compound 44 sensitive cell lines were co-treated for 4 days, a 30-60 fold lower IC$_{50}$ of Compound 44 was observed, demonstrating similar trends to that of the 4+3 treatment schedule (Table 1). Similar results were observed with 7 day co-treatment, and the 4+3 model (Table 1). In EZH2 WT GCB cell lines, despite yielding no measureable Compound 44 $IC_{50}$ after 4 days, both cell lines exhibited decreased proliferation and a measurable Compound 44 $IC_{50}$ after 4 days of co-treatment with prednisolone (Table 1). EZH2 WT GCB cells also responded to the 4+3 model and/or 7 day co-treatment schedules (Table 1). Strikingly, EZH2 mutant, Compound 44 insensitive cell lines, which also exhibit no measurable Compound 44 $IC_{50}$ after 4 day treatment, demonstrated decreased proliferation with 4 day co-treatment, with even greater response to the combination with the 4+3 treatment schedule as well as with 7 day co-treatment (Table 1). Only one of the cell lines demonstrated a combination benefit when cells were pre-treated with prednisolone, then co-treated with Compound 44 and prednisolone, suggesting that the order of drug addition is important for the synergy effect (Table 1).

Figure 9A:
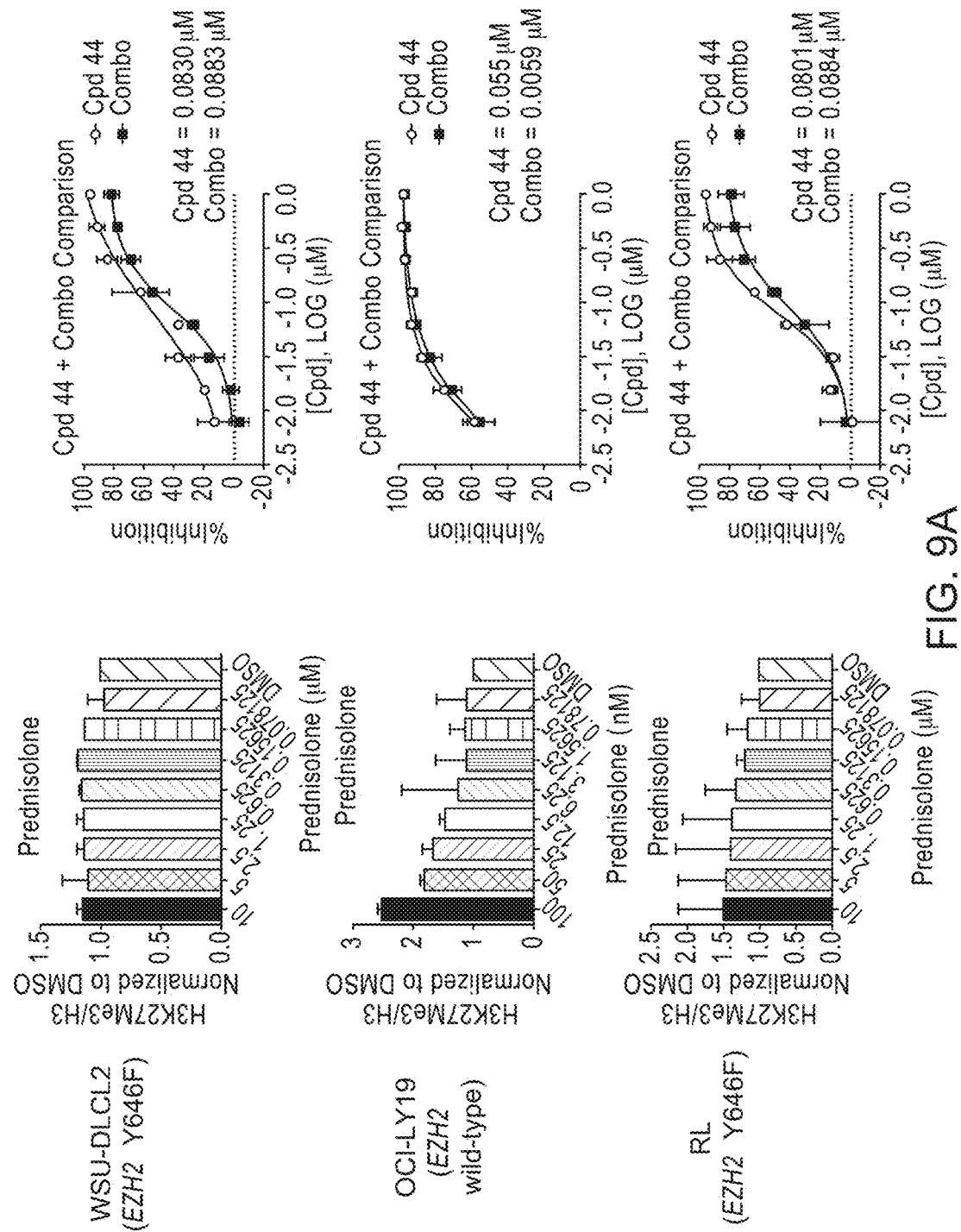
FIGS. 9A-9D are panels showing that global H3K27 acetylation and trimethylation are unaffected by prednisolone or combination treatment. Cells were treated for 4 days with increasing doses of prednisolone, Compound 44 (Cpd 44), or a combination of Compound 44 with a constant dose of prednisolone. Acid extracted histones were analyzed by ELISA for H3K27Me3 levels (FIG. 9A) (prednisolone alone, left panel; Compound 44/prednisolone combination, right panel, with $IC_{50}$ values as insets of each graph). For prednisolone treatment, H3K27Me3 values are represented as a bar graph as there were no dose dependent changes observed with this compound. WSU-DLCL2 (FIG. 9B), OCI-LY19 (FIG. 9C) or RL cells (FIG. 9D) were treated for 4 days with increasing doses of prednisolone, Compound 44, or a combination of Compound 44 with a constant dose of prednisolone. Acid extracted histones were analyzed by western blot for H3K27 acetylation levels.
Figure 9B:
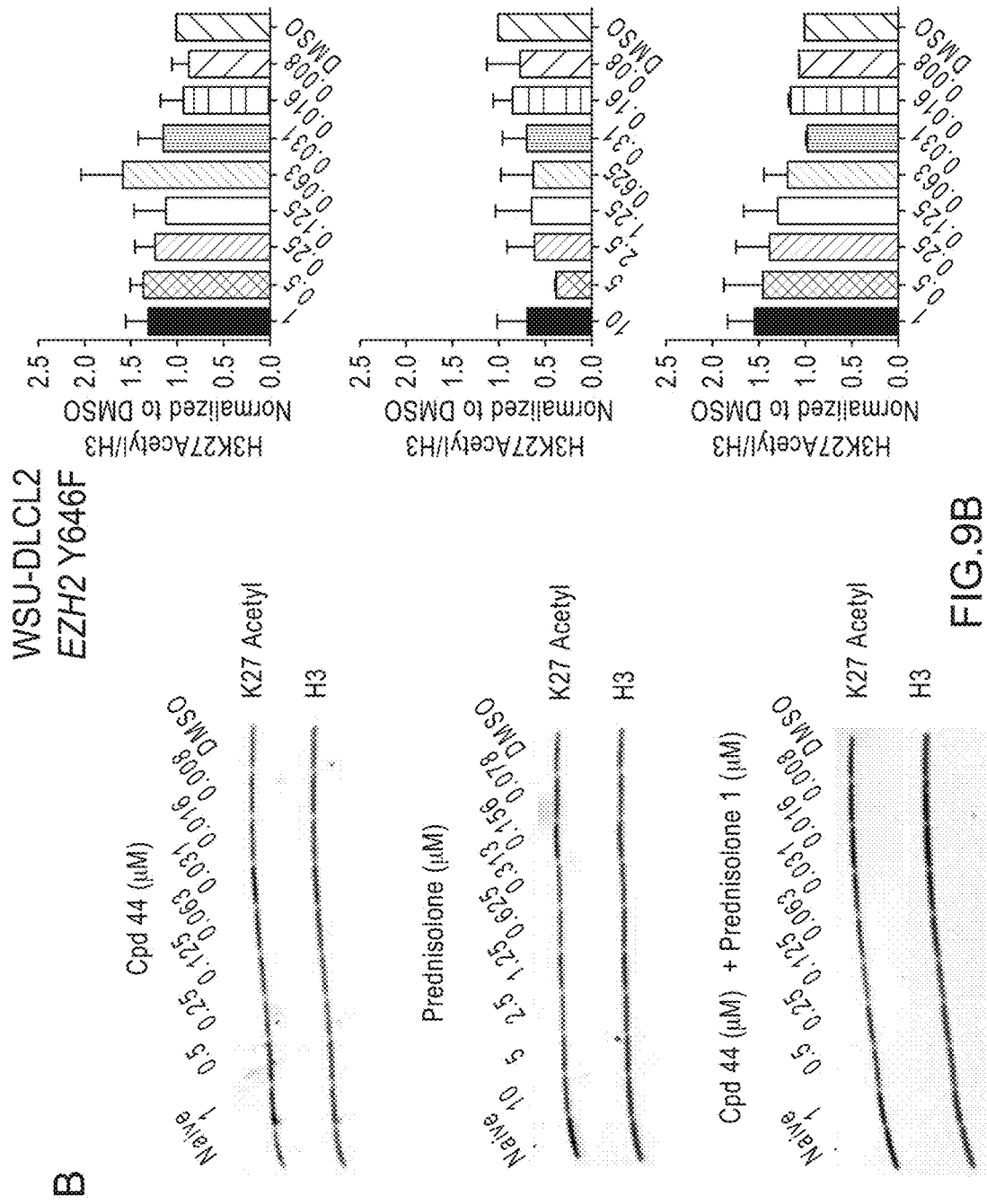
Figure 9C:
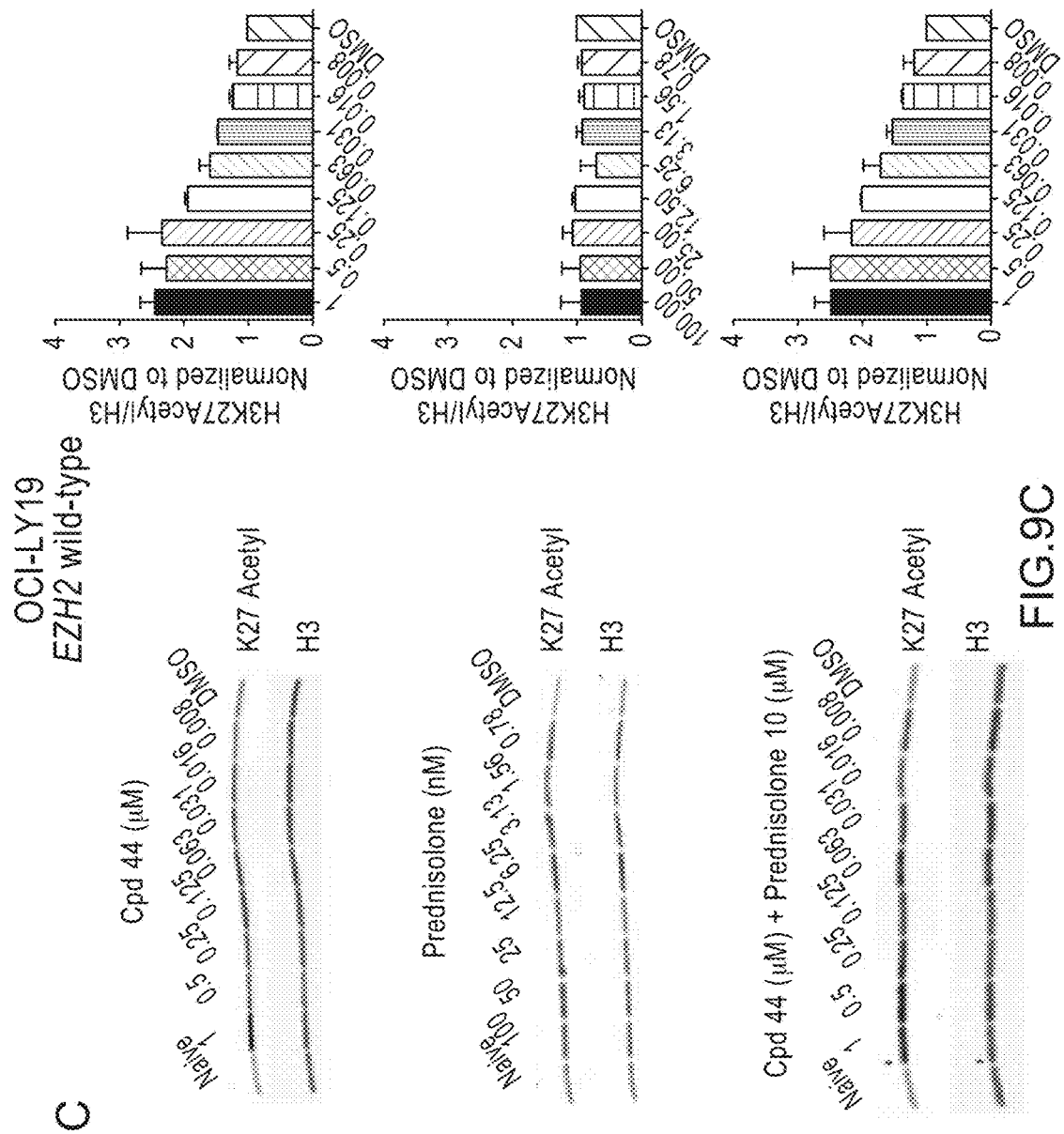
Figure 9D:
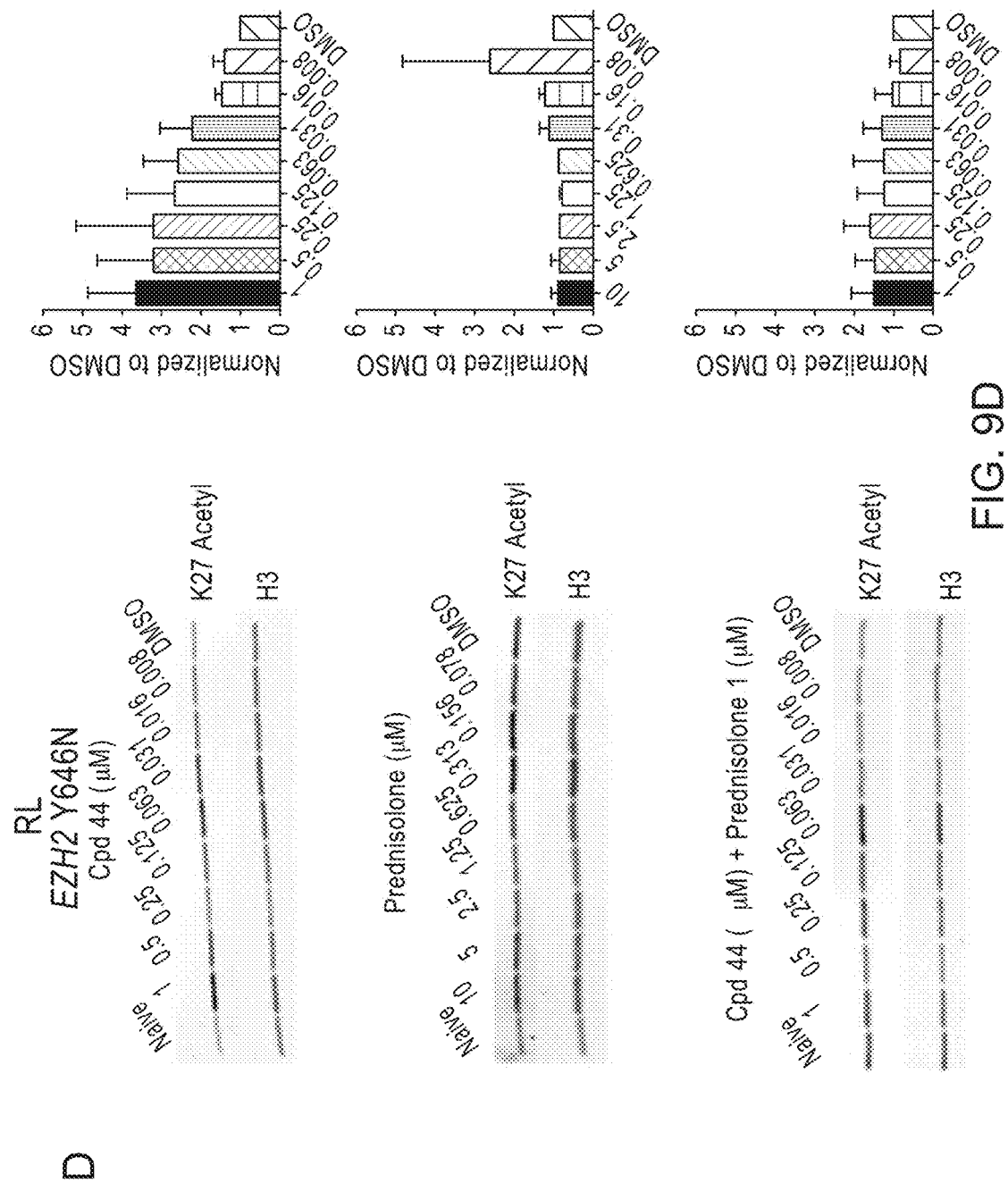
Figure 10:
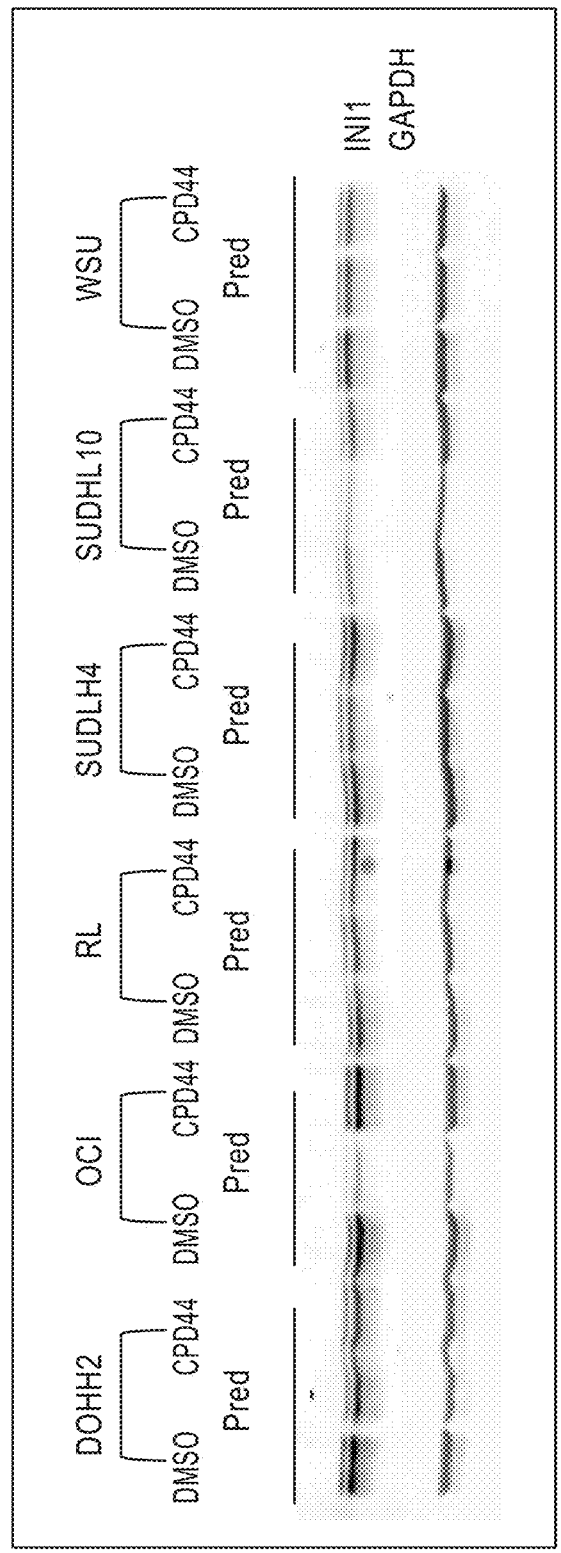
FIG. 10 is a western blot showing that single agent treatment with Compound 44 or prednisolone has no effect on SMARCB1 protein levels.

To evaluate potential mechanisms responsible for the observed combination benefits of Compound 44 and GRag in these cell lines, we determined whether Prednisolone treatment affected global methylation and acetylation of H3K27 following a four day treatment either alone or in combination with Compound 44 in WSU-DLCL2, OCI-LY19, and RL cells (two independent experiments). Single agent Prednisolone had no effect on H3K27Me3 levels in WSU-DLCL2 or RL cells, but did increase H3K27Me3 levels at higher doses in OCI-LY19 cells (FIG. 9A). Due to the high sensitivity of OCI-LY19 cells to Prednisolone, in contrast to the Prednisolone-insensitive EZH2 mutant lines, a lower Prednisolone dose was necessary for the treatment of OCY-LY19 cells. The inclusion of Prednisolone did not alter the Compound 44 $IC_{50}$ for H3K27Me3 inhibition in any cell line (FIG. 9A). Likewise, global H3K27 acetylation levels were not affected by Prednisolone alone or the combination of Compound 44 and prednisolone (FIGS. 9B, 9C & 9D).

Having found that global levels of H3K27 acetylation or trimethylation were unaffected, transcriptional regulation of GR signaling pathways was studied. WSU-DLCL2, SU-DHL10, RL, SU-DHL4, OCI-LY19, and DOHH2 cells were treated with a single concentration of Compound 44, prednisolone, or the combination for 4 days, and gene expression was analyzed using a glucocorticoid signaling PCR array (Table 4). Overall, a larger number of genes were down-regulated with both prednisolone and combination treatments in all cell lines, pointing to a role of GR as both activator and repressor of gene expression. Here, the activating function of GR was focused on and 3 genes which have a synergistic up-regulation in the panel of cell lines with combination treatment were described. Sestrin (SESN1), a putative tumor suppressor that inhibits mTOR signaling (ref), was identified as a gene commonly up-regulated among the 4 EZH2 mutant cell lines in a synergistic manner to with combination treatment, but not in EZH2 WT cell lines (FIG. 8A and Table 2). TNF expression was synergistically up-regulated only in one of the two EZH2 mutant, Compound 44 insensitive cell lines (SUDHL4), with a trend for the other EZH2 mutant, Compound 44 insensitive cell line (RL) showing the same result (FIG. 8B and Table 2). Expression of TSC22D3/GILZ, while up-regulated in all cell lines by prednisolone, is only synergistically enhanced by combination treatment in EZH2 mutant, Compound 44 sensitive cells (FIG. 8C and Table 2).

TABLE 1

Compound 44/GRag Combination Increases EZH2i Sensitivity in EZH2 Y646 (Y641) Cell Lines and Overcomes EZH2i Insensitivity in Cell Lines Resistant to EZH2i

| | 4 Day Cpd44 $IC_{50}$ (uM) | | 7 Day Cpd44 $IC_{50}$ (uM) | | |
|---|---|---|---|---|---|
| Cell Line | Cpd44 Alone | Cpd44 Co-treatment | 4 d Cpd44 Pre/ 3 d Co-treat | 4 d Pred Pre/ 3 d Co-treat | 7 d Co-treatment |
| WSU (Y646-Sens) | 0.53 +/− 0.014 | 0.020 +/− 0.021 | 0.011 +/− 0.0062 | >1 | 0.014 +/− 0.0049 |
| SU-DHL10 (Y646-Sens) | 0.64 +/− 0.26 | 0.0092 +/− 0.0044 | 0.0027 +/− 0.0013 | 0.52, >1 | 0.020 +/− 0.0057 |
| RL (Y646-Res) | >1 | 0.0096 +/− 0.0066 | <<0.004 | 0.38 | <0.004 |
| SU-DHL4 (Y646-Res) | >1 | >1, 0.2, >1 | 0.035 +/− 0.043 | >1 | 0.51 +/− 0.35 |
| DOHH2 (WT) | >1 | 0.20 +/− 0.25 | >1, 0.03, >1 | >1 | 0.34 +/− 0.078 |
| OCI-Ly19 (WT) | >1 | 0.19 +/− 0.11 | 0.0055 +/− 0.0047 | >1 | 0.026, <0.004 |

TABLE 2

Statistical Analysis of Gene Expression Data Presented in FIG. 8A-8C

| | | Sestrin | | TNF | | GILZ | |
|---|---|---|---|---|---|---|---|
| Cell Line | Comparison | P Value | P Value Summary | P Value | P Value Summary | P Value | P Value Summary |
| OCI-LY19 | DMSO vs Combo | 0.9164 | ns | 0.0071 | ** | 0.0075 | ** |
| OCI-LY19 | EPZ-6438 vs Combo | 0.3232 | ns | 0.1553 | ns | 0.0326 | * |

TABLE 2-continued

Statistical Analysis of Gene Expression Data Presented in FIG. 8A-8C

| Cell Line | Comparison | Sestrin P Value | Sestrin P Value Summary | TNF P Value | TNF P Value Summary | GILZ P Value | GILZ P Value Summary |
|---|---|---|---|---|---|---|---|
| OCI-LY19 | Prednisolone vs Combo | 0.1486 | ns | 0.5050 | ns | 0.6353 | ns |
| DOHH2 | DMSO vs Combo | 0.0063 | ** | 0.0589 | ns | 0.0056 | ** |
| DOHH2 | EPZ-6438 vs Combo | 0.0186 | * | 0.1401 | ns | 0.0071 | ** |
| DOHH2 | Prednisolone vs Combo | 0.557 | ns | 0.1000 | ns | 0.2828 | ns |
| WSU-DLCL2 | DMSO vs Combo | <0.0001 | **** | 0.0001 | *** | <0.0001 | **** |
| WSU-DLCL2 | EPZ-6438 vs Combo | <0.0001 | **** | 0.3813 | ns | <0.0001 | **** |
| WSU-DLCL2 | Prednisolone vs Combo | <0.0001 | **** | 0.9483 | ns | 0.0001 | *** |
| SUDHL10 | DMSO vs Combo | 0.0073 | ** | 0.0058 | ** | 0.0102 | * |
| SUDHL10 | EPZ-6438 vs Combo | 0.0081 | ** | 0.0050 | ** | 0.0076 | ** |
| SUDHL10 | Prednisolone vs Combo | 0.0126 | * | 0.1159 | ns | 0.0236 | * |
| RL | DMSO vs Combo | 0.0449 | * | 0.0529 | ns | 0.0623 | ns |
| RL | EPZ-6438 vs Combo | 0.0484 | * | 0.0639 | ns | 0.0635 | ns |
| RL | Prednisolone vs Combo | 0.2329 | ns | 0.0997 | ns | 0.5716 | ns |
| SUDHL4 | DMSO vs Combo | 0.0033 | ** | 0.0043 | ** | 0.0275 | * |
| SUDHL4 | EPZ-6438 vs Combo | 0.0045 | ** | 0.0059 | ** | 0.0196 | * |
| SUDHL4 | Prednisolone vs Combo | 0.010 | * | 0.0205 | * | 0.0107 | ns |

Figure 19:
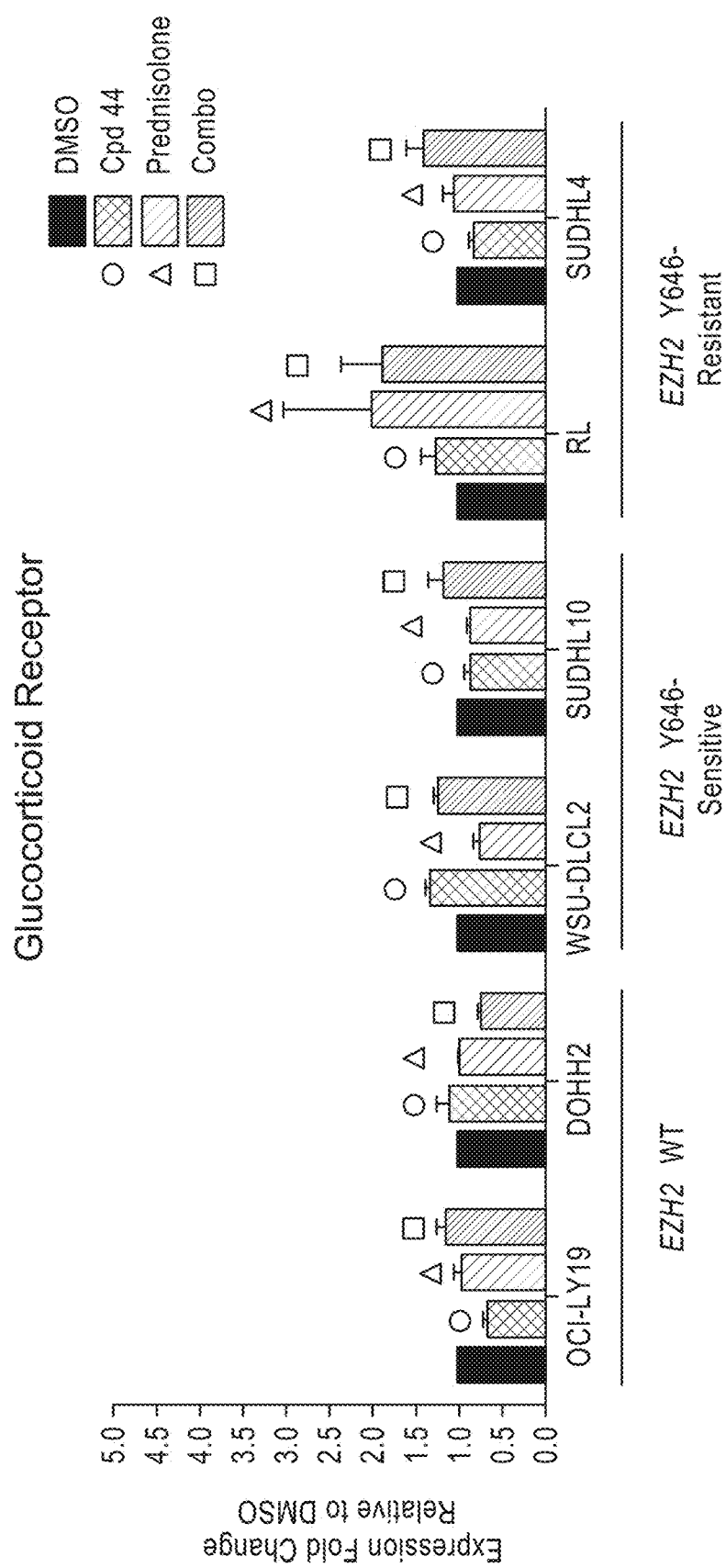
FIG. 19 is a bar graph showing the change in expression levels of the glucocorticoid receptor, normalized to DMSO controls, for EZH2 wild-type (OCI-LY19, DOHH2), EZH2 Y646-sensitive (WSU-DLCL2, SUDHL10), and EZH2 Y646-resistant (RL, SUDHL) cell lines treated with the Compound 44, prednisolone, a combination of Compound 44 and prednisolone, or DMSO. Fold change values were quantified using the ΔΔCt method and ACTB, B2M and GAPDH as reference genes. As the results show, the expression levels of glucocorticoid receptors were not commonly affected among cell lines in the combination.

Pairwise statistical comparisons were performed by two-tailed t test.
ns: not significant;
* $p < 0.05$;
** $p < 0.01$;
*** $p < 0.001$;
**** $p < 0.0001$ Expression levels of glucocorticoid receptor, normalized to DMSO controls, for EZH2 wild-type (i.e., OCI-LY19, DOHH2), EZH2 Y646-sensitive (i.e., WSU-DLCL2, SUDHL10), and EZH2 Y646 resistant (i.e., RL, SUDHL4) cell lines were measured after treatment with the indicated Compound 44, Prednisolone, the combination of Compound 44 and prednisolone, or DMSO (2 biological replicates, see methods materials and methods section 5 for details). As the results show, the expression levels of glucocorticoid receptors were not commonly affected among cell lines in the combination. (FIG. 19) Fold change values were quantified using the $\Delta\Delta Ct$ method and ACTB, B2M and GAPDH as reference genes.

Figure 20A:
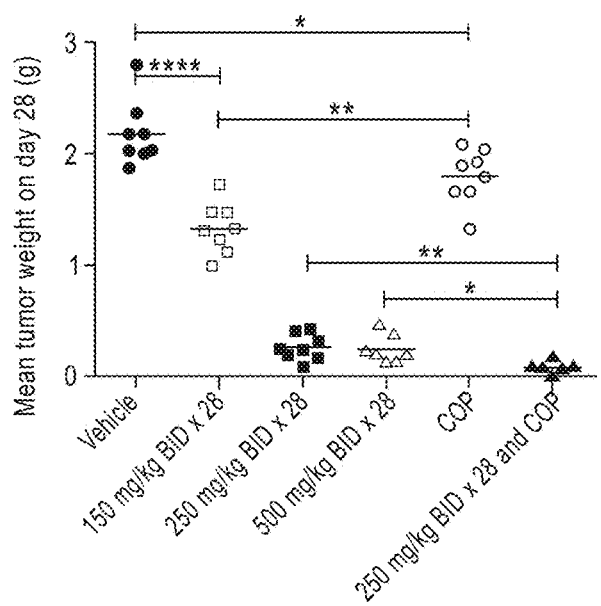
FIGS. 20A-20C show the effects of omitting one or all chemotherapy components from the CHOP regime in xenograft-bearing mice.

The effects of omitting one or all chemotherapy components from the CHOP regime in two additional xenograft studies were then examined. SUDHL10 (EZH2 Y646F) xenograft-bearing mice were treated with Compound 44, COP (chemotherapy without the Doxorubicin component), or their combination for 28 days (FIG. 20A). Mean tumor weights from 8/16 mice, euthanized on day 28, were compared, demonstrating the significant differences in tumor weight between groups (*p<0.05, p<0.01, **p<0.0001; two-tailed t test). Mice dosed with the maximal tolerated dose of Compound 44 or with the Compound 44/COP combination showed 100% survival on day 60, the combination group showed the smallest day 28 tumor weights, statistically different (p<0.05) from all other treatment groups, including the maximal tolerated dose for Compound 44 (FIG. 20A).

Figure 20B:
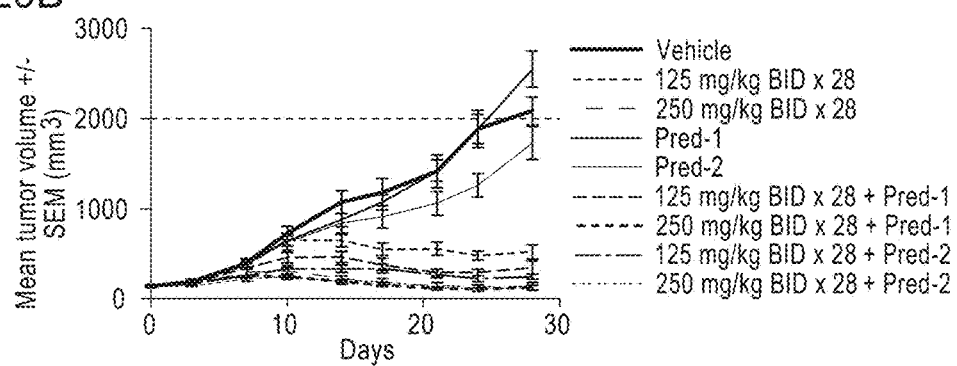
Figure 20C:
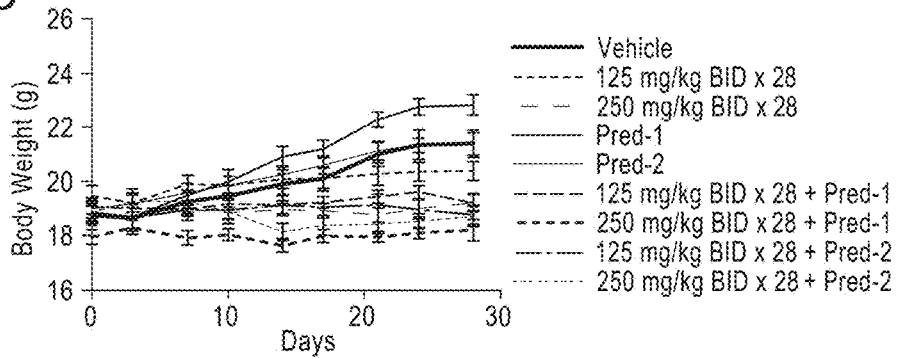

Then, we investigated combination dosing of Compound 44 with Prednisone for 28 days in the SUDHL10 xenograft model with two doses of Compound 44 or Prednisone at two different schedules (Pred-1=Prednisone at 0.15 mg/kg BID×5 on days 1-5 and 22-26; Pred-2=Prednisone 0.15 mg/kg BID×28). As suggested by the in vitro data, Prednisone dosing alone did not induce any significant anti-tumor effect (FIG. 20B). In line with the previous study, 125 mg/kg BID (twice daily) dosing of Compound 44 generated only a partial response, but co-dosing of Compound 44 with Prednisone at 0.15 mg/kg BID, but not with the 2 cycle Prednisone regimen, induced the maximal possible regression achieved with higher doses of Compound 44 alone. Body weight for all mice dosed is shown in FIG. 20C.

SUDHL10 (EZH2 Y646F) xenograft-bearing mice were treated with Compound 44, COP (chemotherapy without the Doxorubicin component), or their combination for 28 days, as specified in the methods. Mean tumor weights from 8/16 mice, euthanized on day 28, are compared, demonstrating the significant differences in tumor weight between groups (*p<0.05, p<0.01, **p<0.0001; two-tailed t test). B) SUDHL10 (EZH2 Y646F) xenograft-bearing mice were treated for 28 days with two doses of Compound 44 or Prednisone at two different schedules (Pred-1=Prednisone at 0.15 mg/kg BID×5 on days 1-5 and 22-26; Pred-2=Prednisone 0.15 mg/kg BID×28). Both compounds were also administered in combination as indicated. Mean tumor volumes ±SEM (n=10) are plotted in top panel. All groups administered EPZ-6438 show statistically significant reduction in tumor growth (p<0.01 at least, vs. vehicle or Prednisone single agent at both schedules; repeated measures ANOVA, Dunnett's post test), while Prednisone single agent did not elicit any significant anti-tumor effect compared to vehicle.

TABLE 3

Summary of Combinations with Compound 44

| | Cell Lines | | | | | | |
|---|---|---|---|---|---|---|---|
| | EZH2 Mutant GCB | | | | EZH2 WT GCB | | |
| | WSU-DLCL2 | SU-DHL10 | SU-DHL6 | DOHH2 | SU-DHL5 | OCI-LY-19 | Toledo |
| C Mafosfamide | Additive | Additive | Additive | No effect | — | — | No effect |
| H Doxorubicin | Synergy | Additive | Additive | No effect | — | — | No effect |
| O Vincristine | Additive | Additive | Additive | No effect | — | — | No effect |
| P Prednisolone | Synergy | Synergy | Synergy | Synergy | Synergy | Synergy | No effect |
| Dexamethasone | Synergy | Synergy | Synergy | Synergy | Synergy | Synergy | No effect |

Finally, tumor growth inhibition was assessed in 3 different EZH2 mutant lymphoma xenograft models. SCID or nude mice bearing subcutaneous lymphoma xenografts were co-dosed with Compound 44 and chemotherapy, either CHOP or COP (CHOP without doxorubicine), and compared to single agent treatments. In WSU-DLCL2 xenograft bearing mice, tumor growth inhibition was achieved at all Compound 44 doses and schedules employed, and was better than CHOP chemotherapy alone (FIG. 7A). Moreover, the combination therapy of Compound 44 and CHOP induced a robust anti-tumor response and significantly (p<0.001) better tumor growth inhibition (93%) than with either single agent alone (45% and 71%, for CHOP and Compound 44, respectively). All single treatments were tolerated; there was minor body weight loss (11.3%) in the Compound 44/CHOP combo group after the first cycle after which the mice recovered before the next cycle of treatment.

In a SU-DHL6 xenograft model, significant tumor growth inhibition was not observed with CHOP alone, or with Compound 44 (FIG. 7B, top panel), in contrast to results previously published by Beguelin et al. using the EZH2 inhibitor GSK503. Strikingly, the combination of Compound 44/CHOP resulted in tumor regression. When dosing was stopped at day 28 and mice were observed out to day 60 for tumor growth delay, this combination resulted in tumor free survival in 58% of the mice (FIG. 7B, bottom panel).

Figure 7C:
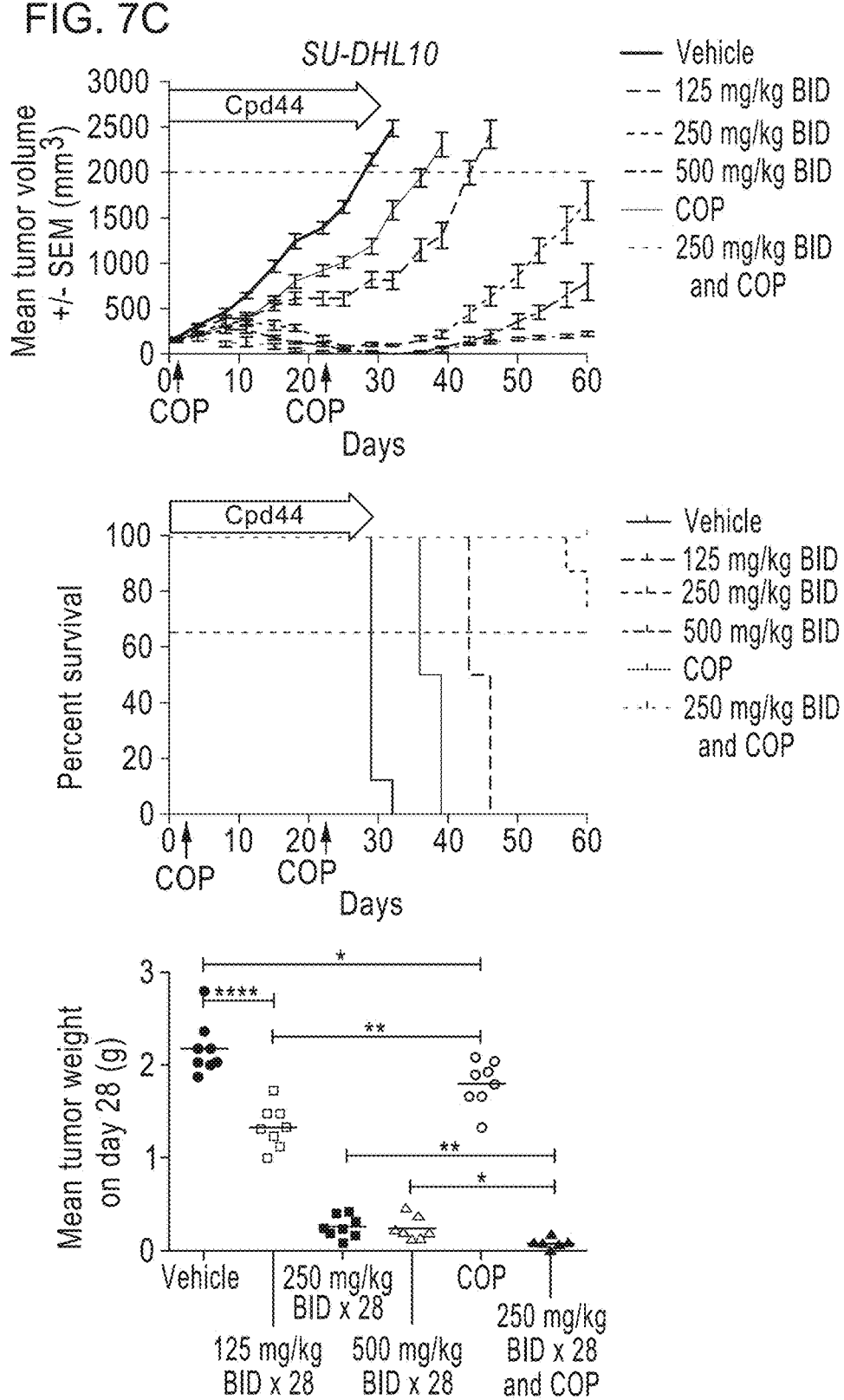

The doxorubicin component of CHOP has a lifetime cumulative dosing limit of <550mg/m$^2$ due to its cardiotoxicity. Therefore, the combination benefit of a Compound 44/chemotherapy regimen that eliminated this component was investigated. In a third study, SU-DHL10 xenograft bearing mice were treated for 28 days with either increasing doses of Compound 44 (BID), doxorubicin-free chemotherapy regimen (COP), or a combination of COP and Compound 44 Tumor growth inhibition was observed at all Compound 44 doses as well as with COP (FIG. 7C, top panel). The 266 mg/kg, 532 mg/kg and COP/Compound 44 combination treatments resulted in regressions that were statistically different from vehicle (p>0.001) as assessed by repeated measures ANOVA and Dunnett's post test, with the Compound 44/COP combination group demonstrating the best overall response. After the 28 day dosing, a sub-group of mice with the smallest tumor burden (8 mice per group) were kept alive without further dosing for a tumor growth delay endpoint. There was a clear dose dependent tumor growth delay benefit for mice treated with Compound 44, while COP treated tumors progressed faster than those treated with Compound 44 (FIG. 7C, middle panel). While mice treated with the maximal tolerated dose of Compound 44 or with the Compound 44/COP combination showed 100% survival on Day 60, the combination group showed the smallest terminal tumor weights, statistically different (p>0.05) from all other treatment groups, including the maximal tolerated dose for Compound 44 (FIG. 7C, bottom panel).

Standard treatments for B-cell NHL are combination chemotherapy regimens composed of cyclophosphamide, doxorubicin, vincristine and prednisolone. While complete response rates of 40-50% can be achieved, a substantial proportion of patients relapse, with 3-year overall survival rates of only about 30%. Relapsed lymphomas can exhibit resistance to a wide range of anticancer drugs, which poses a severe challenge in the clinic to manage these aggressive malignancies. Acquisition of drug resistance in lymphoma is partly driven by the genetic heterogeneity and instability of the tumor cells. Successful treatment of chemoresistant NHL will thus require rational combinations of drugs targeting multiple pathways specific to the different subtypes of B-cell NHL. For instance, in lymphomas of the activated B cell type, constitutive activation of the NFkB pathway has been implicated in therapy resistance, and several novel targeted therapies have shown promise in this subtype.

Epigenetic effectors, such as polycomb, have also been implicated in cancer cell chemo-resistance. EZH2, the catalytic subunit of polycomb repressive complex 2 (PRC2) is a critical oncogenic driver in germinal center derived B-cell lymphomas. These more primitive B-cell malignancies, especially variants expressing EZH2 mutants with altered catalytic activity, require EZH2 for proliferation and survival. Results from preclinical studies forecast great promise for EZH2 catalytic inhibitors for the treatment of such genetically defined cancers, and EZH2 inhibitors may also mitigate chemotherapy resistance. The data presented herein show that Compound 44, a clinical stage EZH2 inhibitor, shows various degrees of combination benefit, ranging from additivity to synergy, with the components of CHOP. Those combination effects were specifically found in lymphomas of the germinal center origin, and, in the case of cyclophosphamide, doxorubicine and vincristine, were restricted to EZH2 mutant-bearing cells. Significant synergy in lymphoma cell killing was also found when Compound 44 was co-dosed with CHOP in vivo. This was especially true in the SU-DHL6 xenograft model where neither single agent showed any significant antitumor activity, but the combination induced durable regressions in >50% of mice. This reiterates the potential importance of overactive EZH2 in chemoresistance of EZH2 mutant lymphoma. Among the CHOP components, Compound 44 combinations with prednisone induced the strongest antiproliferative activity, and this combination could also render insensitive GCB lymphoma cell lines sensitive to EZH2 inhibition, regardless of the EZH2 mutational status. Additionally, this combination benefit is more apparent when Compound 44 and prednisolone are either dosed together or in a sequence specific manner; thus, priming cells with an EZH2 inhibitor, followed by treatment with GR agonists proved particularly effective. This surprising finding has potentially important implications for the application of EZH2 inhibitors in the clinic. First, the widely used GRag are frequently co-administrated with anticancer drugs to prevent drug-induced allergic reactions and to relieve pain, nausea, and emesis, and are pivotal in the treatment of hematopoietic malignancies owing to their ability to induce apoptosis in these cancers. Compared to the other CHOP components, GRag induces the least severe adverse effects. Further, the opportunity to eliminate doxorubicin from the CHOP regime while preserving a combination benefit with Compound 44, as suggested by the data in the SU-DHL10 xenograft model, could spare patients from the dose-limiting cardiotoxic side effects of doxorubicin. Finally, preclinical studies have shown that single agent EZH2 inhibitors induce significant cell killing only in EZH2 mutant-bearing lymphomas, which represent a fraction (20%) of GCB lymphoma patients with high unmet clinical need. The results here demonstrate that GRag/EZH2 inhibitor combinations may have clinical utility in all germinal center derived B cell lymphomas.

Glucocorticoid bound GR molecules move to the nucleus and can act as either transcriptional activator or repressor, depending on the cellular environment. It has been suggested that GR constantly samples the nucleosome for a productive interaction, and the purpose of chromatin-modifying enzymes is to provide regulated access of GR, its cofactors and the basal transcription machinery to DNA. Other studies show that GR often binds to preexisting regions of open chromatin, and the chromatin architecture in a given cell type is organized such that GR can act in a tissue specific manner. Accessibility to GR binding sites can further be enhanced by ATP-dependent chromatin remodeling, and the SWI/SNF complex plays a key role in this activity. Not wishing to be bound by a particular theory or a specific mechanism of action, it is conceivable that aberrant chromatin repression, induced by EZH2 mediated hypertrimethylation of H3K27, can block some of the otherwise accessible GR binding sites, interfering with normal GR mediated gene induction or repression. Indeed, all EZH2 mutant lymphoma cell lines are insensitive to GRag treatment, while concentration-dependent cell killing is observed in EZH2 WT cells. The observation that pretreatment with prednisolone, followed by Compound 44 treatment, cannot induce synergy in almost all cell lines tested, points towards the possibility of EZH2 inhibitor induced chromatin remodeling being the rate limiting step for the enhanced action of GR. Also, PRC2 is known to antagonize with SWI/SNF function and the down-regulation of core subunits of the SWI/SNF complex—SMARCA4, ARID1A, and INI1— have been associated with resistance to prednisolone in acute lymphoblastic T-cell leukemia. Since the relationship of INI1 loss and EZH2 over-activation has been established in rhabdoid tumors, whether global INI1 protein levels would increase in various lymphoma cells exposed to Compound 44 or prednisolone, potentially allowing greater accessibility of GR to its binding sites after increased SWI/SNF function, was investigated.

GR pathway gene expression arrays revealed both increased and decreased gene expression after treatment of several GCB lymphoma cells (both EZH2 WT and mutant) with Compound 44, prednisolone or their combination, confirming the dual function of GR. The only gene that was synergistically up-regulated with the combination in all EZH2 mutant lymphoma cells was SESN1, a TP53 tumor suppressor with functions in cellular response to DNA damage and oxidative stress. Sestrins inhibit cell growth by activating AMP-activated protein kinase, resulting in the inhibition of the mTOR pathway. Hence SESN1 mediated mTOR pathway inhibition may be an important mechanism of reintroducing GRag sensitivity in EZH2 mutant lymphoma cells after Compound 44 treatment.

Conversely, GRag/Compound 44 combination treatment could also induce cell killing in those EZH2 mutant lymphoma cell lines that have been reported as refractory to EZH2 inhibitor treatment (RL, SU-DHL4). SESN1 was induced with combination treatment in those cell lines as well, but an additional synergistic up-regulation of TNF, a potent inflammatory cytokine, was observed specifically in RL and SU-DHL4 cells. This observation seems surprising as TNF and glucocorticoids usually act antagonistically. TNF, through its receptor TNFR-1, can induce apoptosis, but also has the ability to transduce survival signals, mainly through the NFkB pathway. It is thus possible that increased TNF expression, induced by the Compound 44/prednisolone combination, may shift TNF action towards apoptosis in the context of GR agonist repression of NFkB-mediated transcription. It is unclear, however, why this mechanism would result in synergistic cell killing in Compound 44 insensitive EZH2 mutant cells. The potential importance of aberrant repression of negative regulators of the NFkB pathway in GRag resistance and the potential role of EZH2 mediating that is further supported by our observation that GILZ is synergistically up-regulated in 2 out of 6 cells lines with the combination.

Methods

Medium Throughput Assay

Lymphoma cells were seeded into flasks (50,000 cells/mL for WSU-DLCL2, and DOHH2, 10,000 cells/mL for SU-DHL10, and 100,000 cells/mL for Toledo) and pretreated with 7 doses of Compound 44 or DMSO for 4 days or 6 days for Toledo assays. Cells were then split back to 50,000 cells/mL for WSU-DLCL2 and DOHH2 or 30,000 cells/mL for SU-DHL-10 and co-treated with Compound 44 and compound of interest using the HP D300 digital dispenser (Tecan). Both drugs were serially diluted two-fold and combined in a matrix with constant ratios diagonally across the plate with a final DMSO content of 0.11% (v/v). After 3 days of co-treatment (5 days for Toledo assays), cell viability was measured via ATP content using CellTiter-Glo® (Promega) and luminescence was detected using a SpectraMax M5 microplate reader (Molecular Devices).

Synergy quantification is performed using the Chou-Talalay method for drug combination (Ref 1). The Combination Index (CI) equation offers a quantitative definition for additivity (CI=1), synergism (CI<1), and antagonism (CI>1). This equation used fractional effect (Fa) values from a constant ratio of drug combination to determine CI values. The resulting plot (Fa-CI) plot shows the resultant CI values bracketed by 95% confidence intervals. These Fa-CI plots are generated using the Calcusyn for Windows software (Ref 2). CI values<1 with confidence interval lines also below 1 indicate statistically significant synergism.

For drug combinations where only one drug showed more than 50% inhibition, Potency shifts were determined. Dose responses were plotted using Graphpad Prism and either 50% or 60% inhibitory concentrations were interpolated from the dose response curves. Potency shifts were considered significant when confidence intervals for dose responses did not overlap.

Cell Lines, Compounds, and Treatment Outline

WSU-DLCL2, SU-DHL10, RL, SU-DHL4, OCI-LY19, and DOHH2 were previously described (NatChemBio 2012). For combination studies, a modified version of our proliferation assay in suspension cells was used, as previously described (Daigle et al, Cancel Cell, Vol. 20, 1. Pg. 53-65 (2011); Daigle et al., Blood, 121, 13, 2533-2541 (2013)). Briefly, on day 0, cells were plated in triplicate in 96-well plates at initial densities to ensure linear log phase growth over 4 days. Cells were treated with either a dose curve of Compound 44 (starting at a top dose of 1 µM), a single dose of prednisolone (Catalog# and Manufacturer) at a concentration 10-fold lower than the 4-day IC50 of the drug, or a combination of Compound 44 and prednisolone. On day 4, cells were counted using Viacount reagent in the guava easyCyte flow cytometer, and the viable cell number was used to replate cells at the original densities for 3 additional days. Cells that were pre-treated with Compound 44 either received continuous Compound 44 alone, or the combination of Compound 44 and prednisolone (constant dose); cells pre-treated with prednisolone either received continuous prednisolone, or the combination of prednisolone and Compound 44; cells co-treated for 4 days continued to receive co-treatment through 7 days.

Xenograft Studies

All the procedures related to animal handling, care and the treatment in this study were performed according to the guidelines approved by the Institutional Animal Care and Use Committee (IACUC) of CRL Piedmont and Shanghai ChemPartner following the guidance of the Association for Assessment and Accreditation of Laboratory Animal Care (AAALAC). WSU-DLCL2, SU-DHL6, or SU-DHL10 cells were harvested during mid-log phase growth, and re-suspended in PBS with 50% Matrigel™ (BD Biosciences), and injected into immune-compromised mice. Each mouse received 1×107 cells (0.2 mL cell suspension) subcutaneously in the right flank, and once tumors reached a predetermined size, mice were orally dosed with different doses of Compound 44 at various schedules for up to 28 days and/or CHOP/COP on the following schedules: Cyclophosphamide was administered intraperitoneally (i.p.), and doxorubicin and vincristine were each administered via bolus tail vein injections (i.v.); each was given once daily on Days 1 and 8 in the SU-DHL6 study, and on Days 1 and 22 in the WSU-DLCL2 and SU-DHL10 studies. Prednisone was administered p.o. on two cycles of five daily doses, starting on Days 1 and 8 ((qd×5)×2, Days 1, 8) in the SU-DHL6 study, and on Days 1 and 22 ((qd×5)×2, Days 1, 22) in the WSU-DLCL2 and SU-DHL10 studies. Each dose was delivered in a volume of 0.2 mL/20 g mouse (10 mL/kg), and adjusted for the last recorded weight of individual animals. Tumor measurements and body weights were collected twice-weekly for 28 days for all studies. To determine tumor growth delay in the SU-DHL10 and SU-DHL6 studies, each test animal was euthanized when its neoplasm reached the endpoint volume of 2000 mm3 or on the last day of the study (day 60), whichever came first.

Quantitative PCR

WSU-DLCL2, SU-DHL10, RL, SU-DHL4, OCI-LY19, and DOHH2 cells were treated in parallel with DMSO, 1 µM of Compound 44 (SU-DHL10 treated with 100 nM Compound 44), a dose of prednisolone at a concentration 10-fold lower than the 4-day $IC_{50}$, or the combination of drugs for 4 days. Cells were harvested and total mRNA was extracted from cell pellets using the RNeasy Plus Mini Kit (Qiagen; 74134). For the RT2 Glucocorticoid Signaling PCR array (Qiagen; PAHS-154ZE-4), cDNA was made by RT2 First Strand Kit (Qiagen; 330401). Array RT-PCR was performed using ViiA 7 Real-Time PCR Systems [Applied Biosystems (AB)] with RT2 SYBR Green ROX qPCR Mastermix (Qiagen; 330521). Gene expression was normalized to array's B2M and fold change compared to DMSO was calculated using the $\Delta\Delta Ct$ method. To validate array data, TaqMan probe based qPCR was carried out using TaqMan Fast Advanced Master Mix (AB; 4444964) and TaqMan primer/probe sets for Sestrin (AB; Hs00902787_m1) and TNF (AB; Hs01113624_m1). Fold change was calculated as above, normalizing to RPLPO (AB; 4333761F).

ELISA

Histones were extracted from tumor samples as described above. Histones were prepared in equivalent concentrations in coating buffer (PBS+0.05%BSA) yielding 0.5 ng/µl of sample, and 100 µl of sample or standard was added in duplicate to 2 96-well ELISA plates (Thermo Labsystems, Immulon 4HBX #3885). The plates were sealed and incubated overnight at 4° C. The following day, plates were washed 3× with 300 µl/well PBST (PBS+0.05% Tween 20; 10× PBST, KPL #51-14-02) on a Bio Tek plate washer. Plates were blocked with 300 µl/well of diluent (PBS+2%BSA+0.05% Tween 20), incubated at RT for 2 hours, and washed 3× with PB ST. All antibodies were diluted in diluent. 100 µl/well of anti-H3K27me3 (CST #9733, 50% glycerol stock 1:1,000) or anti-total H3 (Abcam ab1791, 50% glycerol 1:10,000) was added to each plate. Plates were incubated for 90 min at RT and washed 3× with PBST. 100 µl/well of anti-Rb-IgG-HRP (Cell Signaling Technology, 7074) was added 1:2,000 to the H3K27Me3 plate and 1:6,000 to the H3 plate and incubated for 90 min at RT. Plates were washed 4× with PBST. For detection, 100 µl/well of TMB substrate (BioFx Laboratories, #TMBS) was added and plates incubated in the dark at RT for 5 min. Reaction was stopped with 100 µl/well 1N $H_2SO_4$. Absorbance at 450 nm was read on SpectaMax M5 Microplate reader.

TABLE 4a

Ct values and fold changes from the RT2 Glucocorticoid signaling PCR array analysis for OCI cell line.

| | Ct Values | | | | ΔCT (B2M) | | | |
|---|---|---|---|---|---|---|---|---|
| Gene | DMSO | Cpd44 | Pred | Combo | DMSO | Cpd44 | Pred | Combo |
| ADARB1 | 24.373 | 23.799 | 24.946 | 24.323 | 7.368 | 6.580 | 7.319 | 7.177 |
| AFF1 | 21.574 | 21.780 | 21.892 | 21.613 | 4.569 | 4.561 | 4.265 | 4.467 |

TABLE 4a-continued

Ct values and fold changes from the RT2 Glucocorticoid signaling PCR array analysis for OCI cell line.

| | | | | | | | | |
|---|---|---|---|---|---|---|---|---|
| AK2 | 20.300 | 20.497 | 20.859 | 20.656 | 3.295 | 3.278 | 3.232 | 3.510 |
| AMPD3 | 27.424 | 26.984 | 27.937 | 27.892 | 10.419 | 9.765 | 10.310 | 10.746 |
| ANGPTL4 | 30.465 | 30.374 | 30.333 | 29.769 | 13.460 | 13.155 | 12.706 | 12.623 |
| ANXA4 | 23.319 | 23.379 | 24.130 | 23.394 | 6.314 | 6.160 | 6.503 | 6.248 |
| AQP1 | Undetermined | 31.992 | Undetermined | Undetermined | #VALUE! | 14.773 | #VALUE! | #VALUE! |
| ARID5B | 22.092 | 22.537 | 22.635 | 22.538 | 5.087 | 5.318 | 5.008 | 5.392 |
| ASPH | 27.926 | 27.556 | 28.894 | 27.701 | 10.921 | 10.337 | 11.267 | 10.555 |
| ATF4 | 18.500 | 18.838 | 19.578 | 19.368 | 1.495 | 1.619 | 1.951 | 2.222 |
| BCL6 | 27.421 | 26.240 | 28.282 | 26.459 | 10.416 | 9.021 | 10.655 | 9.313 |
| BMPER | Undetermined | 34.674 | Undetermined | 32.290 | #VALUE! | 17.455 | #VALUE! | 15.144 |
| CALCR | Undetermined | Undetermined | Undetermined | Undetermined | #VALUE! | #VALUE! | #VALUE! | #VALUE! |
| CEBPA | 30.199 | 27.522 | 30.852 | 28.731 | 13.194 | 10.303 | 13.225 | 11.585 |
| CEBPB | 23.119 | 23.723 | 24.427 | 24.678 | 6.114 | 6.504 | 6.800 | 7.532 |
| COL4A2 | 32.777 | 33.300 | 35.000 | 32.293 | 15.772 | 16.081 | 17.373 | 15.147 |
| CREB1 | 22.477 | 22.697 | 23.159 | 22.702 | 5.472 | 5.478 | 5.532 | 5.556 |
| CREB3 | 24.708 | 24.979 | 25.174 | 24.863 | 7.703 | 7.760 | 7.547 | 7.717 |
| CREB3L4 | 24.162 | 24.000 | 24.936 | 24.497 | 7.157 | 6.781 | 7.309 | 7.351 |
| CTGF | 21.557 | 21.719 | 21.099 | 20.311 | 4.552 | 4.500 | 3.472 | 3.165 |
| CYB561 | Undetermined | 33.134 | Undetermined | 32.534 | #VALUE! | 15.915 | #VALUE! | 15.388 |
| DDIT4 | 24.102 | 23.567 | 23.551 | 23.195 | 7.097 | 6.348 | 5.924 | 6.049 |
| DIRAS2 | Undetermined | Undetermined | Undetermined | Undetermined | #VALUE! | #VALUE! | #VALUE! | #VALUE! |
| DUSP1 | 20.981 | 20.800 | 21.767 | 21.200 | 3.976 | 3.581 | 4.140 | 4.054 |
| EDN1 | Undetermined | Undetermined | 33.433 | 32.487 | #VALUE! | #VALUE! | 15.806 | 15.341 |
| EHD3 | 28.984 | 28.117 | 28.833 | 27.236 | 11.979 | 10.898 | 11.206 | 10.090 |
| ERRFI1 | Undetermined | Undetermined | 32.824 | Undetermined | #VALUE! | #VALUE! | 15.197 | #VALUE! |
| FKBP5 | 22.604 | 22.499 | 22.353 | 21.699 | 5.599 | 5.280 | 4.726 | 4.553 |
| FOSL2 | 26.226 | 26.214 | 26.368 | 25.547 | 9.221 | 8.995 | 8.741 | 8.401 |
| GDPD1 | 26.444 | 26.638 | 27.196 | 26.808 | 9.439 | 9.419 | 9.569 | 9.662 |
| GHRHR | 37.467 | 33.641 | 35.486 | 36.113 | 20.462 | 16.422 | 17.859 | 18.967 |
| GLUL | 22.916 | 22.385 | 23.448 | 22.402 | 5.911 | 5.166 | 5.821 | 5.256 |
| GOT1 | 23.094 | 23.224 | 23.810 | 23.450 | 6.089 | 6.005 | 6.183 | 6.304 |
| H6PD | 26.842 | 26.141 | 26.981 | 26.440 | 9.837 | 8.922 | 9.354 | 9.294 |
| HAS2 | Undetermined | Undetermined | Undetermined | Undetermined | #VALUE! | #VALUE! | #VALUE! | #VALUE! |
| HNRPLL | 29.840 | 29.708 | 30.306 | 29.439 | 12.835 | 12.489 | 12.679 | 12.293 |
| IL10 | Undetermined | Undetermined | 34.155 | Undetermined | #VALUE! | #VALUE! | 16.528 | #VALUE! |
| IL1RN | 33.932 | 32.902 | Undetermined | Undetermined | 16.927 | 15.683 | #VALUE! | #VALUE! |
| IL6 | Undetermined | Undetermined | Undetermined | 32.602 | #VALUE! | #VALUE! | #VALUE! | 15.456 |
| IL6R | Undetermined | Undetermined | Undetermined | Undetermined | #VALUE! | #VALUE! | #VALUE! | #VALUE! |
| KLF13 | 23.416 | 23.178 | 23.963 | 23.145 | 6.411 | 5.959 | 6.336 | 5.999 |
| KLF9 | 29.546 | 28.545 | 28.597 | 27.791 | 12.541 | 11.326 | 10.970 | 10.546 |
| LOX | 33.344 | 32.825 | 32.787 | 31.904 | 16.339 | 15.606 | 15.160 | 14.758 |
| MERTK | 29.340 | 28.749 | 29.685 | 28.885 | 12.335 | 11.530 | 12.058 | 11.739 |
| MT1E | Undetermined | Undetermined | Undetermined | Undetermined | #VALUE! | #VALUE! | #VALUE! | #VALUE! |
| MT2A | 22.845 | 22.941 | 23.298 | 22.515 | 5.840 | 5.722 | 5.671 | 5.369 |
| NFKBIA | 21.672 | 21.905 | 22.337 | 21.755 | 4.667 | 4.686 | 4.710 | 4.609 |
| NR3C1 | 20.940 | 21.131 | 21.276 | 20.605 | 3.935 | 3.912 | 3.649 | 3.459 |
| PDCD7 | 23.121 | 23.359 | 28.314 | 23.491 | 6.116 | 6.140 | 10.687 | 6.345 |
| PDGFRB | 32.160 | 33.308 | 30.540 | 30.932 | 15.155 | 16.089 | 12.913 | 13.786 |
| PDP1 | 26.092 | 25.788 | 26.292 | 25.520 | 9.087 | 8.569 | 8.665 | 8.374 |
| PER1 | 24.615 | 25.503 | 25.500 | 26.016 | 7.610 | 8.284 | 7.873 | 8.870 |
| PER2 | Undetermined | 23.177 | 23.707 | 23.482 | #VALUE! | 5.958 | 6.080 | 6.336 |
| PIK3R1 | 23.175 | 23.115 | 23.678 | 23.317 | 6.170 | 5.896 | 6.051 | 6.171 |
| PLD1 | Undetermined | Undetermined | Undetermined | 33.540 | #VALUE! | #VALUE! | #VALUE! | 16.394 |
| PLEKHF1 | 30.216 | 29.694 | 30.977 | 30.285 | 13.211 | 12.475 | 13.350 | 13.139 |
| POU2F1 | 24.562 | 24.656 | 25.232 | 24.555 | 7.557 | 7.437 | 7.605 | 7.409 |
| POU2F2 | 31.495 | 31.740 | 31.543 | 31.643 | 14.490 | 14.521 | 13.916 | 14.497 |
| RASA3 | 23.112 | 23.251 | 23.743 | 23.462 | 6.107 | 6.032 | 6.115 | 6.316 |
| RGS2 | 28.455 | 27.701 | 29.467 | 28.122 | 11.450 | 10.482 | 11.840 | 10.976 |
| RHOB | 22.108 | 20.944 | 20.967 | 19.659 | 5.103 | 3.725 | 3.340 | 2.513 |
| RHOJ | Undetermined | Undetermined | Undetermined | Undetermined | #VALUE! | #VALUE! | #VALUE! | #VALUE! |
| SESN1 | 22.463 | 22.424 | 23.126 | 22.491 | 5.458 | 5.205 | 5.499 | 5.345 |
| SGK1 | 26.351 | 26.107 | 25.819 | 24.816 | 9.346 | 8.888 | 8.192 | 7.670 |
| SLC10A6 | 31.403 | 30.432 | 31.656 | 32.746 | 14.398 | 13.213 | 14.029 | 15.600 |
| SLC19A2 | 24.878 | 24.881 | 25.910 | 25.274 | 7.873 | 7.662 | 8.283 | 8.128 |
| SLC22A5 | 29.254 | 29.101 | 30.112 | 29.115 | 12.249 | 11.882 | 12.485 | 11.969 |
| SNTA1 | 28.151 | 27.457 | 28.892 | 28.483 | 11.146 | 10.238 | 11.265 | 11.337 |
| SPHK1 | 28.555 | 28.787 | 29.199 | 29.124 | 11.550 | 11.568 | 11.572 | 11.978 |
| SPSB1 | 27.338 | 27.455 | 28.347 | 28.097 | 10.333 | 10.236 | 10.720 | 10.951 |
| STAT5A | 22.115 | 22.442 | 22.673 | 22.391 | 5.110 | 5.223 | 5.046 | 5.245 |
| STAT5B | 22.886 | 22.979 | 23.838 | 23.297 | 5.881 | 5.760 | 6.211 | 6.151 |
| TBL1XR1 | 21.317 | 21.488 | 21.705 | 21.430 | 4.312 | 4.269 | 4.078 | 4.284 |
| TNF | 24.763 | 24.377 | 24.612 | 23.620 | 7.758 | 7.158 | 6.985 | 6.474 |
| TNFAIP3 | 22.296 | 22.827 | 23.168 | 23.327 | 5.291 | 5.608 | 5.541 | 6.181 |
| TSC22D3 | 25.692 | 25.235 | 24.619 | 24.219 | 8.687 | 8.016 | 6.992 | 7.073 |
| USP2 | 33.949 | 31.341 | 33.986 | 32.493 | 16.944 | 14.122 | 16.359 | 15.347 |
| USP54 | 24.856 | 25.235 | 25.764 | 24.989 | 7.851 | 8.016 | 8.137 | 7.843 |
| VDR | 25.093 | 24.754 | 24.985 | 24.651 | 8.088 | 7.535 | 7.358 | 7.505 |
| VLDLR | 28.968 | 28.902 | 29.671 | 29.488 | 11.963 | 11.683 | 12.044 | 12.342 |

TABLE 4a-continued

Ct values and fold changes from the RT2 Glucocorticoid signaling PCR array analysis for OCI cell line.

| | | | | | | | | |
|---|---|---|---|---|---|---|---|---|
| XDH | Undetermined | Undetermined | Undetermined | Undetermined | #VALUE! | #VALUE! | #VALUE! | #VALUE! |
| ZFP36 | 24.550 | 25.191 | Undetermined | 25.349 | 7.545 | 7.972 | #VALUE! | 8.203 |
| ZHX3 | 24.941 | 24.761 | 24.833 | 24.322 | 7.936 | 7.542 | 7.206 | 7.176 |
| ZNF281 | 22.504 | 23.249 | 23.997 | 23.695 | 5.499 | 6.030 | 6.370 | 6.549 |
| ACTB | 15.098 | 14.892 | 16.093 | 14.987 | −1.907 | −2.327 | −1.534 | −2.159 |
| B2M | 17.005 | 17.219 | 17.627 | 17.146 | 0.000 | 0.000 | 0.000 | 0.000 |
| GAPDH | 15.880 | 16.149 | 16.519 | 16.647 | −1.125 | −1.070 | −1.108 | −0.499 |
| HPRT1 | 21.462 | 21.828 | 22.125 | 21.813 | 4.457 | 4.609 | 4.498 | 4.667 |
| RPLP0 | 14.351 | 14.350 | 15.011 | 14.197 | −2.654 | −2.869 | −2.616 | −2.949 |
| HGDC | Undetermined | Undetermined | Undetermined | Undetermined | #VALUE! | #VALUE! | #VALUE! | #VALUE! |
| RTC | 22.174 | 21.961 | 21.962 | 22.251 | 5.169 | 4.742 | 4.335 | 5.105 |
| RTC | 22.089 | 21.953 | 22.140 | 22.008 | 5.084 | 4.734 | 4.513 | 4.862 |
| RTC | 22.195 | 21.961 | 22.167 | 21.993 | 5.190 | 4.742 | 4.540 | 4.847 |
| PPC | 18.397 | 18.268 | 18.432 | 18.371 | 1.392 | 1.049 | 0.805 | 1.225 |
| PPC | 18.426 | 18.330 | 18.320 | 18.347 | 1.421 | 1.111 | 0.693 | 1.201 |
| PPC | 18.301 | 17.672 | 18.372 | 18.378 | 1.296 | 0.453 | 0.745 | 1.232 |

| | Cpd44 | | Pred | | Combo | |
|---|---|---|---|---|---|---|
| Gene | ΔΔCT | Fold Change | ΔΔCT | Fold Change | ΔΔCT | Fold Change |
| ADARB1 | −0.788 | 1.727 | −0.049 | 1.035 | −0.191 | 1.142 |
| AFF1 | −0.008 | 1.006 | −0.304 | 1.235 | −0.102 | 1.073 |
| AK2 | −0.017 | 1.012 | −0.063 | 1.045 | 0.215 | 0.862 |
| AMPD3 | −0.654 | 1.574 | −0.109 | 1.078 | 0.327 | 0.797 |
| ANGPTL4 | −0.305 | 1.235 | −0.754 | 1.686 | −0.837 | 1.786 |
| ANXA4 | −0.154 | 1.113 | 0.189 | 0.877 | −0.066 | 1.047 |
| AQP1 | #VALUE! | #VALUE! | #VALUE! | #VALUE! | #VALUE! | #VALUE! |
| ARID5B | 0.231 | 0.852 | −0.079 | 1.056 | 0.305 | 0.809 |
| ASPH | −0.584 | 1.499 | 0.346 | 0.787 | −0.366 | 1.289 |
| ATF4 | 0.124 | 0.918 | 0.456 | 0.729 | 0.727 | 0.604 |
| BCL6 | −1.395 | 2.630 | 0.239 | 0.847 | −1.103 | 2.148 |
| BMPER | #VALUE! | #VALUE! | #VALUE! | #VALUE! | #VALUE! | #VALUE! |
| CALCR | #VALUE! | #VALUE! | #VALUE! | #VALUE! | #VALUE! | #VALUE! |
| CEBPA | −2.891 | 7.418 | 0.031 | 0.979 | −1.609 | 3.050 |
| CEBPB | 0.390 | 0.763 | 0.686 | 0.622 | 1.418 | 0.374 |
| COL4A2 | 0.309 | 0.807 | 1.601 | 0.330 | −0.625 | 1.542 |
| CREB1 | 0.006 | 0.996 | 0.060 | 0.959 | 0.084 | 0.943 |
| CREB3 | 0.057 | 0.961 | −0.156 | 1.114 | 0.014 | 0.990 |
| CREB3L4 | −0.376 | 1.298 | 0.152 | 0.900 | 0.194 | 0.874 |
| CTGF | −0.052 | 1.037 | −1.080 | 2.114 | −1.387 | 2.615 |
| CYB561 | #VALUE! | #VALUE! | #VALUE! | #VALUE! | #VALUE! | #VALUE! |
| DDIT4 | −0.749 | 1.681 | −1.173 | 2.255 | −1.048 | 2.068 |
| DIRAS2 | #VALUE! | #VALUE! | #VALUE! | #VALUE! | #VALUE! | #VALUE! |
| DUSP1 | −0.395 | 1.315 | 0.164 | 0.893 | 0.078 | 0.947 |
| EDN1 | #VALUE! | #VALUE! | #VALUE! | #VALUE! | #VALUE! | #VALUE! |
| EHD3 | −1.081 | 2.116 | −0.773 | 1.709 | −1.889 | 3.704 |
| ERRFI1 | #VALUE! | #VALUE! | #VALUE! | #VALUE! | #VALUE! | #VALUE! |
| FKBP5 | −0.319 | 1.247 | −0.873 | 1.831 | −1.046 | 2.065 |
| FOSL2 | −0.226 | 1.170 | −0.480 | 1.395 | −0.820 | 1.765 |
| GDPD1 | −0.020 | 1.014 | 0.130 | 0.914 | 0.223 | 0.857 |
| GHRHR | −4.040 | 16.450 | −2.603 | 6.075 | −1.495 | 2.819 |
| GLUL | −0.745 | 1.675 | −0.090 | 1.064 | −0.655 | 1.575 |
| GOT1 | −0.084 | 1.060 | 0.094 | 0.937 | 0.215 | 0.862 |
| H6PD | −0.915 | 1.886 | −0.483 | 1.398 | −0.543 | 1.457 |
| HAS2 | #VALUE! | #VALUE! | #VALUE! | #VALUE! | #VALUE! | #VALUE! |
| HNRPLL | −0.346 | 1.271 | −0.156 | 1.114 | −0.542 | 1.456 |
| IL10 | #VALUE! | #VALUE! | #VALUE! | #VALUE! | #VALUE! | #VALUE! |
| IL1RN | −1.244 | 2.369 | #VALUE! | #VALUE! | #VALUE! | #VALUE! |
| IL6 | #VALUE! | #VALUE! | #VALUE! | #VALUE! | #VALUE! | #VALUE! |
| IL6R | #VALUE! | #VALUE! | #VALUE! | #VALUE! | #VALUE! | #VALUE! |
| KLF13 | −0.452 | 1.368 | −0.075 | 1.053 | −0.412 | 1.331 |
| KLF9 | −1.215 | 2.321 | −1.571 | 2.971 | −1.896 | 3.722 |
| LOX | −0.733 | 1.662 | −1.179 | 2.264 | −1.581 | 2.992 |
| MERTK | −0.805 | 1.747 | −0.277 | 1.212 | −0.596 | 1.512 |
| MT1E | #VALUE! | #VALUE! | #VALUE! | #VALUE! | #VALUE! | #VALUE! |
| MT2A | −0.118 | 1.085 | −0.169 | 1.124 | −0.471 | 1.386 |
| NFKBIA | 0.019 | 0.987 | 0.043 | 0.971 | −0.058 | 1.041 |
| NR3C1 | −0.023 | 1.016 | −0.286 | 1.219 | −0.476 | 1.391 |
| PDCD7 | 0.024 | 0.984 | 4.571 | 0.042 | 0.229 | 0.853 |
| PDGFRB | 0.934 | 0.523 | −2.242 | 4.731 | −1.369 | 2.583 |
| PDP1 | −0.518 | 1.432 | −0.422 | 1.340 | −0.713 | 1.639 |
| PER1 | 0.674 | 0.627 | 0.263 | 0.833 | 1.260 | 0.418 |
| PER2 | #VALUE! | #VALUE! | #VALUE! | #VALUE! | #VALUE! | #VALUE! |
| PIK3R1 | −0.274 | 1.209 | −0.119 | 1.086 | 0.001 | 0.999 |
| PLD1 | #VALUE! | #VALUE! | #VALUE! | #VALUE! | #VALUE! | #VALUE! |
| PLEKHF1 | −0.736 | 1.666 | 0.139 | 0.908 | −0.072 | 1.051 |
| POU2F1 | −0.120 | 1.087 | 0.048 | 0.967 | −0.148 | 1.108 |

TABLE 4a-continued

Ct values and fold changes from the RT2 Glucocorticoid signaling PCR array analysis for OCI cell line.

| | | | | | | |
|---|---|---|---|---|---|---|
| POU2F2 | 0.031 | 0.979 | −0.574 | 1.489 | 0.007 | 0.995 |
| RASA3 | −0.075 | 1.053 | 0.009 | 0.994 | 0.209 | 0.865 |
| RGS2 | −0.968 | 1.956 | 0.390 | 0.763 | −0.474 | 1.389 |
| RHOB | −1.378 | 2.599 | −1.763 | 3.394 | −2.590 | 6.021 |
| RHOJ | #VALUE! | #VALUE! | #VALUE! | #VALUE! | #VALUE! | #VALUE! |
| SESN1 | −0.253 | 1.192 | 0.041 | 0.972 | −0.113 | 1.081 |
| SGK1 | −0.458 | 1.374 | −1.154 | 2.225 | −1.676 | 3.195 |
| SLC10A6 | −1.185 | 2.274 | −0.369 | 1.291 | 1.202 | 0.435 |
| SLC19A2 | −0.211 | 1.157 | 0.410 | 0.753 | 0.255 | 0.838 |
| SLC22A5 | −0.367 | 1.290 | 0.236 | 0.849 | −0.280 | 1.214 |
| SNTA1 | −0.908 | 1.876 | 0.119 | 0.921 | 0.191 | 0.876 |
| SPHK1 | 0.018 | 0.988 | 0.022 | 0.985 | 0.428 | 0.743 |
| SPSB1 | −0.097 | 1.070 | 0.387 | 0.765 | 0.618 | 0.652 |
| STAT5A | 0.113 | 0.925 | −0.064 | 1.045 | 0.135 | 0.911 |
| STAT5B | −0.121 | 1.087 | 0.330 | 0.796 | 0.270 | 0.829 |
| TBL1XR1 | −0.043 | 1.030 | −0.234 | 1.176 | −0.028 | 1.020 |
| TNF | −0.600 | 1.516 | −0.773 | 1.709 | −1.284 | 2.435 |
| TNFAIP3 | 0.317 | 0.803 | 0.250 | 0.841 | 0.890 | 0.540 |
| TSC22D3 | −0.671 | 1.592 | −1.695 | 3.238 | −1.614 | 3.061 |
| USP2 | −2.822 | 7.071 | −0.585 | 1.500 | −1.597 | 3.025 |
| USP54 | 0.165 | 0.892 | 0.286 | 0.820 | −0.008 | 1.006 |
| VDR | −0.553 | 1.467 | −0.730 | 1.659 | −0.583 | 1.498 |
| VLDLR | −0.280 | 1.214 | 0.081 | 0.945 | 0.379 | 0.769 |
| XDH | #VALUE! | #VALUE! | #VALUE! | #VALUE! | #VALUE! | #VALUE! |
| ZFP36 | 0.427 | 0.744 | #VALUE! | #VALUE! | 0.658 | 0.634 |
| ZHX3 | −0.394 | 1.314 | −0.730 | 1.659 | −0.760 | 1.693 |
| ZNF281 | 0.531 | 0.692 | 0.871 | 0.547 | 1.050 | 0.483 |
| ACTB | | | | | | |
| B2M | | | | | | |
| GAPDH | | | | | | |
| HPRT1 | | | | | | |
| RPLP0 | | | | | | |
| HGDC | | | | | | |
| RTC | | | | | | |
| RTC | | | | | | |
| RTC | | | | | | |
| PPC | | | | | | |
| PPC | | | | | | |
| PPC | | | | | | |

TABLE 4b

Ct values and fold changes from the RT2 Glucocorticoid signaling PCR array analysis for DOHH2 cell line.

| | Ct Values | | | | ΔCT (B2M) | | | |
|---|---|---|---|---|---|---|---|---|
| Gene | DMSO | Cpd44 | Pred | Combo | DMSO | Cpd44 | Pred | Combo |
| ADARB1 | 31.818 | 31.431 | 33.560 | 30.189 | 12.809 | 12.855 | 14.676 | 12.038 |
| AFF1 | 24.684 | 23.888 | 23.992 | 23.224 | 5.675 | 5.312 | 5.108 | 5.073 |
| AK2 | 20.334 | 20.173 | 20.262 | 19.961 | 1.325 | 1.597 | 1.378 | 1.810 |
| AMPD3 | 26.401 | 26.146 | 27.535 | 26.852 | 7.392 | 7.570 | 8.651 | 8.701 |
| ANGPTL4 | 31.134 | 30.820 | 31.538 | 30.854 | 12.125 | 12.244 | 12.654 | 12.703 |
| ANXA4 | 24.817 | 24.273 | 24.997 | 24.268 | 5.808 | 5.697 | 6.113 | 6.117 |
| AQP1 | Undetermined | Undetermined | Undetermined | Undetermined | #VALUE! | #VALUE! | #VALUE! | #VALUE! |
| ARID5B | 23.881 | 23.782 | 23.885 | 23.886 | 4.872 | 5.206 | 5.001 | 5.735 |
| ASPH | 22.970 | 22.823 | 23.369 | 22.996 | 3.961 | 4.247 | 4.485 | 4.845 |
| ATF4 | 19.156 | 19.190 | 19.313 | 18.983 | 0.147 | 0.614 | 0.429 | 0.832 |
| BCL6 | 21.529 | 21.323 | 21.801 | 21.773 | 2.520 | 2.747 | 2.917 | 3.622 |
| BMPER | 38.037 | 39.092 | 39.378 | 39.656 | 19.028 | 20.516 | 20.494 | 21.505 |
| CALCR | Undetermined | 33.630 | Undetermined | Undetermined | #VALUE! | 15.054 | #VALUE! | #VALUE! |
| CEBPA | 34.654 | 30.676 | 32.188 | 30.646 | 15.645 | 12.100 | 13.304 | 12.495 |
| CEBPB | 23.911 | 23.925 | 24.317 | 24.001 | 4.902 | 5.349 | 5.433 | 5.850 |
| COL4A2 | 32.314 | 34.119 | 38.993 | 34.143 | 13.305 | 15.543 | 20.109 | 15.992 |
| CREB1 | 22.930 | 22.746 | 22.890 | 22.730 | 3.921 | 4.170 | 4.006 | 4.579 |
| CREB3 | 24.929 | 24.840 | 24.865 | 24.647 | 5.920 | 6.264 | 5.981 | 6.496 |
| CREB3L4 | 24.405 | 24.110 | 24.616 | 24.373 | 5.396 | 5.534 | 5.732 | 6.222 |
| CTGF | 33.711 | 32.760 | 33.728 | 33.696 | 14.702 | 14.184 | 14.844 | 15.545 |
| CYB561 | 37.790 | 31.945 | 39.582 | 34.331 | 18.781 | 13.369 | 20.698 | 16.180 |
| DDIT4 | 23.934 | 23.508 | 24.105 | 22.948 | 4.925 | 4.932 | 5.221 | 4.797 |
| DIRAS2 | Undetermined | Undetermined | Undetermined | Undetermined | #VALUE! | #VALUE! | #VALUE! | #VALUE! |
| DUSP1 | 27.604 | 27.132 | 27.866 | 27.262 | 8.595 | 8.556 | 8.982 | 9.111 |
| EDN1 | 31.233 | 32.260 | 32.263 | 31.224 | 12.224 | 13.684 | 13.379 | 13.073 |
| EHD3 | 32.315 | 28.852 | 31.098 | 28.674 | 13.306 | 10.276 | 12.214 | 10.523 |
| ERRFI1 | 32.525 | 30.163 | 32.635 | 29.588 | 13.516 | 11.587 | 13.751 | 11.437 |

TABLE 4b-continued

Ct values and fold changes from the RT2 Glucocorticoid signaling PCR array analysis for DOHH2 cell line.

| | | | | | | | | |
|---|---|---|---|---|---|---|---|---|
| FKBP5 | 21.985 | 21.520 | 20.912 | 20.512 | 2.976 | 2.944 | 2.028 | 2.361 |
| FOSL2 | 31.767 | 29.872 | 31.543 | 29.925 | 12.758 | 11.296 | 12.659 | 11.774 |
| GDPD1 | 27.532 | 27.570 | 27.884 | 27.396 | 8.523 | 8.994 | 9.000 | 9.245 |
| GHRHR | 37.684 | 39.644 | 36.095 | 37.813 | 18.675 | 21.068 | 17.211 | 19.662 |
| GLUL | 36.133 | 36.671 | 34.574 | 36.099 | 17.124 | 18.095 | 15.690 | 17.948 |
| GOT1 | 23.427 | 23.126 | 23.532 | 22.880 | 4.418 | 4.550 | 4.648 | 4.729 |
| H6PD | 24.717 | 24.377 | 24.969 | 24.453 | 5.708 | 5.801 | 6.085 | 6.302 |
| HAS2 | Undetermined | Undetermined | Undetermined | Undetermined | #VALUE! | #VALUE! | #VALUE! | #VALUE! |
| HNRPLL | 30.324 | 29.151 | 33.284 | 31.380 | 11.315 | 10.575 | 14.400 | 13.229 |
| IL10 | Undetermined | Undetermined | Undetermined | Undetermined | #VALUE! | #VALUE! | #VALUE! | #VALUE! |
| IL1RN | Undetermined | 32.271 | 33.560 | 31.586 | #VALUE! | 13.695 | 14.676 | 13.435 |
| IL6 | Undetermined | Undetermined | 34.758 | 37.608 | #VALUE! | #VALUE! | 15.874 | 19.457 |
| IL6R | Undetermined | 31.962 | Undetermined | 32.383 | #VALUE! | 13.386 | #VALUE! | 14.232 |
| KLF13 | 22.951 | 22.420 | 22.546 | 21.765 | 3.942 | 3.844 | 3.662 | 3.614 |
| KLF9 | 28.691 | 28.439 | 28.547 | 27.741 | 9.682 | 9.863 | 9.663 | 9.590 |
| LOX | 33.562 | 32.997 | 34.158 | 32.855 | 14.553 | 14.421 | 15.274 | 14.704 |
| MERTK | 32.997 | 32.456 | 32.892 | 31.474 | 13.988 | 13.880 | 14.008 | 13.323 |
| MT1E | 39.692 | Undetermined | Undetermined | Undetermined | 20.683 | #VALUE! | #VALUE! | #VALUE! |
| MT2A | 39.646 | Undetermined | Undetermined | Undetermined | 20.637 | #VALUE! | #VALUE! | #VALUE! |
| NFKBIA | 22.891 | 22.625 | 22.830 | 22.625 | 3.882 | 4.049 | 3.946 | 4.474 |
| NR3C1 | 22.602 | 22.430 | 22.794 | 22.573 | 3.593 | 3.854 | 3.910 | 4.422 |
| PDCD7 | 23.656 | 23.417 | 23.552 | 23.397 | 4.647 | 4.841 | 4.668 | 5.246 |
| PDGFRB | Undetermined | 35.193 | 34.934 | 31.552 | #VALUE! | 16.617 | 16.050 | 13.401 |
| PDP1 | 25.863 | 25.175 | 25.682 | 25.330 | 6.854 | 6.599 | 6.798 | 7.179 |
| PER1 | 24.944 | 24.717 | 25.142 | 25.289 | 5.935 | 6.141 | 6.258 | 7.138 |
| PER2 | 24.642 | 23.835 | 24.159 | 23.476 | 5.633 | 5.259 | 5.275 | 5.325 |
| PIK3R1 | 24.177 | 23.712 | 23.850 | 23.610 | 5.168 | 5.136 | 4.966 | 5.459 |
| PLD1 | 37.038 | Undetermined | 37.120 | 38.323 | 18.029 | #VALUE! | 18.236 | 20.172 |
| PLEKHF1 | 29.886 | 28.946 | 29.414 | 28.738 | 10.877 | 10.370 | 10.530 | 10.587 |
| POU2F1 | 24.378 | 24.003 | 24.648 | 23.667 | 5.369 | 5.427 | 5.764 | 5.516 |
| POU2F2 | 22.469 | 22.167 | 22.489 | 21.930 | 3.460 | 3.591 | 3.605 | 3.779 |
| RASA3 | 27.152 | 27.636 | 27.803 | 28.392 | 8.143 | 9.060 | 8.919 | 10.241 |
| RGS2 | 24.790 | 24.861 | 25.514 | 25.639 | 5.781 | 6.285 | 6.630 | 7.488 |
| RHOB | 32.661 | 30.745 | 33.162 | 30.702 | 13.652 | 12.169 | 14.278 | 12.551 |
| RHOJ | Undetermined | Undetermined | Undetermined | Undetermined | #VALUE! | #VALUE! | #VALUE! | #VALUE! |
| SESN1 | 24.226 | 23.848 | 22.839 | 21.993 | 5.217 | 5.272 | 3.955 | 3.842 |
| SGK1 | 27.633 | 27.821 | 29.628 | 29.125 | 8.624 | 9.245 | 10.744 | 10.974 |
| SLC10A6 | 34.483 | 36.435 | 36.176 | 32.738 | 15.474 | 17.859 | 17.292 | 14.587 |
| SLC19A2 | 25.600 | 24.859 | 25.455 | 24.769 | 6.591 | 6.283 | 6.571 | 6.618 |
| SLC22A5 | 28.392 | 27.992 | 28.915 | 27.835 | 9.383 | 9.416 | 10.031 | 9.684 |
| SNTA1 | 24.584 | 24.550 | 25.124 | 25.000 | 5.575 | 5.974 | 6.240 | 6.849 |
| SPHK1 | 30.677 | 28.863 | 29.971 | 28.646 | 11.668 | 10.287 | 11.087 | 10.495 |
| SPSB1 | 27.110 | 26.652 | 26.911 | 26.621 | 8.101 | 8.076 | 8.027 | 8.470 |
| STAT5A | 24.237 | 23.771 | 23.885 | 23.477 | 5.228 | 5.195 | 5.001 | 5.326 |
| STAT5B | 22.503 | 22.328 | 22.632 | 22.414 | 3.494 | 3.752 | 3.748 | 4.263 |
| TBL1XR1 | 21.397 | 20.994 | 21.304 | 21.133 | 2.388 | 2.418 | 2.420 | 2.982 |
| TNF | 31.328 | 31.849 | 31.956 | 31.194 | 12.319 | 13.273 | 13.072 | 13.043 |
| TNFAIP3 | 28.260 | 27.520 | Undetermined | 30.586 | 9.251 | 8.944 | #VALUE! | 12.435 |
| TSC22D3 | 25.176 | 24.752 | 23.310 | 22.374 | 6.167 | 6.176 | 4.426 | 4.223 |
| USP2 | 24.104 | 23.684 | 23.501 | 22.971 | 5.095 | 5.108 | 4.617 | 4.820 |
| USP54 | 26.599 | 25.892 | 26.683 | 25.856 | 7.590 | 7.316 | 7.799 | 7.705 |
| VDR | 27.406 | 26.426 | 26.847 | 26.577 | 8.397 | 7.850 | 7.963 | 8.426 |
| VLDLR | 27.166 | 27.232 | 28.584 | 27.543 | 8.157 | 8.656 | 9.700 | 9.392 |
| XDH | Undetermined | Undetermined | Undetermined | Undetermined | #VALUE! | #VALUE! | #VALUE! | #VALUE! |
| ZFP36 | 24.170 | 23.980 | 24.270 | 24.094 | 5.161 | 5.404 | 5.386 | 5.943 |
| ZHX3 | 25.200 | 24.611 | 24.418 | 23.897 | 6.191 | 6.035 | 5.534 | 5.746 |
| ZNF281 | 24.066 | 23.541 | 23.828 | 23.343 | 5.057 | 4.965 | 4.944 | 5.192 |
| ACTB | 14.843 | 14.519 | 14.721 | 14.509 | −4.166 | −4.057 | −4.163 | −3.642 |
| B2M | 19.009 | 18.576 | 18.884 | 18.151 | 0.000 | 0.000 | 0.000 | 0.000 |
| GAPDH | 16.513 | 16.197 | 16.551 | 16.157 | −2.496 | −2.379 | −2.333 | −1.994 |
| HPRT1 | 21.698 | 21.561 | 21.777 | 21.657 | 2.689 | 2.985 | 2.893 | 3.506 |
| RPLP0 | 15.187 | 14.935 | 15.128 | 14.595 | −3.822 | −3.641 | −3.756 | −3.556 |
| HGDC | Undetermined | Undetermined | Undetermined | Undetermined | #VALUE! | #VALUE! | #VALUE! | #VALUE! |
| RTC | 21.284 | 21.345 | 21.449 | 21.483 | 2.275 | 2.769 | 2.565 | 3.332 |
| RTC | 21.287 | 21.410 | 21.464 | 21.371 | 2.278 | 2.834 | 2.580 | 3.220 |
| RTC | 21.358 | 21.384 | 21.483 | 21.483 | 2.349 | 2.808 | 2.599 | 3.332 |
| PPC | 18.611 | 18.672 | 18.684 | 18.624 | −0.398 | 0.096 | −0.200 | 0.473 |
| PPC | 18.638 | 19.142 | 18.699 | 18.587 | −0.371 | 0.566 | −0.185 | 0.436 |
| PPC | 18.646 | 18.711 | 19.076 | 18.685 | −0.363 | 0.135 | 0.192 | 0.534 |

| | Cpd44 | | Pred | | Combo | |
|---|---|---|---|---|---|---|
| Gene | ΔΔCT | Fold Change | ΔΔCT | Fold Change | ΔΔCT | Fold Change |
| ADARB1 | 0.046 | 0.969 | 1.867 | 0.274 | −0.771 | 1.706 |
| AFF1 | −0.363 | 1.286 | −0.567 | 1.481 | −0.602 | 1.518 |
| AK2 | 0.272 | 0.828 | 0.053 | 0.964 | 0.485 | 0.714 |
| AMPD3 | 0.178 | 0.884 | 1.259 | 0.418 | 1.309 | 0.404 |

TABLE 4b-continued

Ct values and fold changes from the RT2 Glucocorticoid signaling PCR array analysis for DOHH2 cell line.

| | | | | | | |
|---|---|---|---|---|---|---|
| ANGPTL4 | 0.119 | 0.921 | 0.529 | 0.693 | 0.578 | 0.670 |
| ANXA4 | −0.111 | 1.080 | 0.305 | 0.809 | 0.309 | 0.807 |
| AQP1 | #VALUE! | #VALUE! | #VALUE! | #VALUE! | #VALUE! | #VALUE! |
| ARID5B | 0.334 | 0.793 | 0.129 | 0.914 | 0.863 | 0.550 |
| ASPH | 0.286 | 0.820 | 0.524 | 0.695 | 0.884 | 0.542 |
| ATF4 | 0.467 | 0.723 | 0.282 | 0.822 | 0.685 | 0.622 |
| BCL6 | 0.227 | 0.854 | 0.397 | 0.759 | 1.102 | 0.466 |
| BMPER | 1.488 | 0.357 | 1.466 | 0.362 | 2.477 | 0.180 |
| CALCR | #VALUE! | #VALUE! | #VALUE! | #VALUE! | #VALUE! | #VALUE! |
| CEBPA | −3.545 | 11.672 | −2.341 | 5.067 | −3.150 | 8.877 |
| CEBPB | 0.447 | 0.734 | 0.531 | 0.692 | 0.948 | 0.518 |
| COL4A2 | 2.238 | 0.212 | 6.804 | 0.009 | 2.687 | 0.155 |
| CREB1 | 0.249 | 0.841 | 0.085 | 0.943 | 0.658 | 0.634 |
| CREB3 | 0.344 | 0.788 | 0.061 | 0.959 | 0.576 | 0.671 |
| CREB3L4 | 0.138 | 0.909 | 0.336 | 0.792 | 0.826 | 0.564 |
| CTGF | −0.518 | 1.432 | 0.142 | 0.906 | 0.843 | 0.557 |
| CYB561 | −5.412 | 42.577 | 1.917 | 0.265 | −2.601 | 6.067 |
| DDIT4 | 0.007 | 0.995 | 0.296 | 0.815 | −0.128 | 1.093 |
| DIRAS2 | #VALUE! | #VALUE! | #VALUE! | #VALUE! | #VALUE! | #VALUE! |
| DUSP1 | −0.039 | 1.027 | 0.387 | 0.765 | 0.516 | 0.699 |
| EDN1 | 1.460 | 0.363 | 1.155 | 0.449 | 0.849 | 0.555 |
| EHD3 | −3.030 | 8.168 | −1.092 | 2.132 | −2.783 | 6.883 |
| ERRFI1 | −1.929 | 3.808 | 0.235 | 0.850 | −2.079 | 4.225 |
| FKBP5 | −0.032 | 1.022 | −0.948 | 1.929 | −0.615 | 1.532 |
| FOSL2 | −1.462 | 2.755 | −0.099 | 1.071 | −0.984 | 1.978 |
| GDPD1 | 0.471 | 0.721 | 0.477 | 0.718 | 0.722 | 0.606 |
| GHRHR | 2.393 | 0.190 | −1.464 | 2.759 | 0.987 | 0.505 |
| GLUL | 0.971 | 0.510 | −1.434 | 2.702 | 0.824 | 0.565 |
| GOT1 | 0.132 | 0.913 | 0.230 | 0.853 | 0.311 | 0.806 |
| H6PD | 0.093 | 0.938 | 0.377 | 0.770 | 0.594 | 0.663 |
| HAS2 | #VALUE! | #VALUE! | #VALUE! | #VALUE! | #VALUE! | #VALUE! |
| HNRPLL | −0.740 | 1.670 | 3.085 | 0.118 | 1.914 | 0.265 |
| IL10 | #VALUE! | #VALUE! | #VALUE! | #VALUE! | #VALUE! | #VALUE! |
| IL1RN | #VALUE! | #VALUE! | #VALUE! | #VALUE! | #VALUE! | #VALUE! |
| IL6 | #VALUE! | #VALUE! | #VALUE! | #VALUE! | #VALUE! | #VALUE! |
| IL6R | #VALUE! | #VALUE! | #VALUE! | #VALUE! | #VALUE! | #VALUE! |
| KLF13 | −0.098 | 1.070 | −0.280 | 1.214 | −0.328 | 1.255 |
| KLF9 | 0.181 | 0.882 | −0.019 | 1.013 | −0.092 | 1.066 |
| LOX | −0.132 | 1.096 | 0.721 | 0.607 | 0.151 | 0.901 |
| MERTK | −0.108 | 1.078 | 0.020 | 0.986 | −0.665 | 1.586 |
| MT1E | #VALUE! | #VALUE! | #VALUE! | #VALUE! | #VALUE! | #VALUE! |
| MT2A | #VALUE! | #VALUE! | #VALUE! | #VALUE! | #VALUE! | #VALUE! |
| NFKBIA | 0.167 | 0.891 | 0.064 | 0.957 | 0.592 | 0.663 |
| NR3C1 | 0.261 | 0.835 | 0.317 | 0.803 | 0.829 | 0.563 |
| PDCD7 | 0.194 | 0.874 | 0.021 | 0.986 | 0.599 | 0.660 |
| PDGFRB | #VALUE! | #VALUE! | #VALUE! | #VALUE! | #VALUE! | #VALUE! |
| PDP1 | −0.255 | 1.193 | −0.056 | 1.040 | 0.325 | 0.798 |
| PER1 | 0.206 | 0.867 | 0.323 | 0.799 | 1.203 | 0.434 |
| PER2 | −0.374 | 1.296 | −0.358 | 1.282 | −0.308 | 1.238 |
| PIK3R1 | −0.032 | 1.022 | −0.202 | 1.150 | 0.291 | 0.817 |
| PLD1 | #VALUE! | #VALUE! | 0.207 | 0.866 | 2.143 | 0.226 |
| PLEKHF1 | −0.507 | 1.421 | −0.347 | 1.272 | −0.290 | 1.223 |
| POU2F1 | 0.058 | 0.961 | 0.395 | 0.760 | 0.147 | 0.903 |
| POU2F2 | 0.131 | 0.913 | 0.145 | 0.904 | 0.319 | 0.802 |
| RASA3 | 0.917 | 0.530 | 0.776 | 0.584 | 2.098 | 0.234 |
| RGS2 | 0.504 | 0.705 | 0.849 | 0.555 | 1.707 | 0.306 |
| RHOB | −1.483 | 2.795 | 0.626 | 0.648 | −1.101 | 2.145 |
| RHOJ | #VALUE! | #VALUE! | #VALUE! | #VALUE! | #VALUE! | #VALUE! |
| SESN1 | 0.055 | 0.963 | −1.262 | 2.398 | −1.375 | 2.594 |
| SGK1 | 0.621 | 0.650 | 2.120 | 0.230 | 2.350 | 0.196 |
| SLC10A6 | 2.385 | 0.191 | 1.818 | 0.284 | −0.887 | 1.849 |
| SLC19A2 | −0.308 | 1.238 | −0.020 | 1.014 | 0.027 | 0.981 |
| SLC22A5 | 0.033 | 0.977 | 0.648 | 0.638 | 0.301 | 0.812 |
| SNTA1 | 0.399 | 0.758 | 0.665 | 0.631 | 1.274 | 0.414 |
| SPHK1 | −1.381 | 2.604 | −0.581 | 1.496 | −1.173 | 2.255 |
| SPSB1 | −0.025 | 1.017 | −0.074 | 1.053 | 0.369 | 0.774 |
| STAT5A | −0.033 | 1.023 | −0.227 | 1.170 | 0.098 | 0.934 |
| STAT5B | 0.258 | 0.836 | 0.254 | 0.839 | 0.769 | 0.587 |
| TBL1XR1 | 0.030 | 0.979 | 0.032 | 0.978 | 0.594 | 0.663 |
| TNF | 0.954 | 0.516 | 0.753 | 0.593 | 0.724 | 0.605 |
| TNFAIP3 | −0.307 | 1.237 | #VALUE! | #VALUE! | 3.184 | 0.110 |
| TSC22D3 | 0.009 | 0.994 | −1.741 | 3.343 | −1.944 | 3.848 |
| USP2 | 0.013 | 0.991 | −0.478 | 1.393 | −0.275 | 1.210 |
| USP54 | −0.274 | 1.209 | 0.209 | 0.865 | 0.115 | 0.923 |
| VDR | −0.547 | 1.461 | −0.434 | 1.351 | 0.029 | 0.980 |
| VLDLR | 0.499 | 0.708 | 1.543 | 0.343 | 1.235 | 0.425 |
| XDH | #VALUE! | #VALUE! | #VALUE! | #VALUE! | #VALUE! | #VALUE! |
| ZFP36 | 0.243 | 0.845 | 0.225 | 0.856 | 0.782 | 0.582 |

TABLE 4b-continued

Ct values and fold changes from the RT2 Glucocorticoid signaling PCR array analysis for DOHH2 cell line.

|  |  |  |  |  |  |  |
|---|---|---|---|---|---|---|
| ZHX3 | −0.156 | 1.114 | −0.657 | 1.577 | −0.445 | 1.361 |
| ZNF281 | −0.092 | 1.066 | −0.113 | 1.081 | 0.135 | 0.911 |
| ACTB |  |  |  |  |  |  |
| B2M |  |  |  |  |  |  |
| GAPDH |  |  |  |  |  |  |
| HPRT1 |  |  |  |  |  |  |
| RPLP0 |  |  |  |  |  |  |
| HGDC |  |  |  |  |  |  |
| RTC |  |  |  |  |  |  |
| RTC |  |  |  |  |  |  |
| RTC |  |  |  |  |  |  |
| PPC |  |  |  |  |  |  |
| PPC |  |  |  |  |  |  |
| PPC |  |  |  |  |  |  |

TABLE 4c

Ct values and fold changes from the RT2 Glucocorticoid signaling PCR array analysis for WSU cell line.

| | Ct Values | | | | ΔCT (B2M) | | | |
|---|---|---|---|---|---|---|---|---|
| Gene | DMSO | Cpd44 | Pred | Combo | DMSO | Cpd44 | Pred | Combo |
| ADARB1 | 26.316 | 25.386 | 26.108 | 26.018 | 6.866 | 5.701 | 6.963 | 5.845 |
| AFF1 | 28.103 | 27.925 | 27.334 | 26.727 | 8.653 | 8.240 | 8.189 | 6.554 |
| AK2 | 20.644 | 21.365 | 20.433 | 22.069 | 1.194 | 1.680 | 1.288 | 1.896 |
| AMPD3 | 28.467 | 27.162 | 27.943 | 26.847 | 9.017 | 7.477 | 8.798 | 6.674 |
| ANGPTL4 | 31.444 | 30.487 | 30.810 | 31.510 | 11.994 | 10.802 | 11.665 | 11.337 |
| ANXA4 | 27.736 | 24.659 | 27.406 | 25.013 | 8.286 | 4.974 | 8.261 | 4.840 |
| AQP1 | Undetermined | 33.645 | 33.595 | 32.796 | #VALUE! | 13.960 | 14.450 | 12.623 |
| ARID5B | 26.244 | 26.126 | 26.721 | 27.140 | 6.794 | 6.441 | 7.576 | 6.967 |
| ASPH | 22.285 | 22.415 | 21.939 | 22.834 | 2.835 | 2.730 | 2.794 | 2.661 |
| ATF4 | 19.874 | 20.470 | 19.659 | 20.871 | 0.424 | 0.785 | 0.514 | 0.698 |
| BCL6 | 20.954 | 20.795 | 20.898 | 21.133 | 1.504 | 1.110 | 1.753 | 0.960 |
| BMPER | 39.814 | Undetermined | Undetermined | 38.494 | 20.364 | #VALUE! | #VALUE! | 18.321 |
| CALCR | Undetermined | Undetermined | Undetermined | Undetermined | #VALUE! | #VALUE! | #VALUE! | #VALUE! |
| CEBPA | 28.438 | 27.014 | 27.838 | 27.647 | 8.988 | 7.329 | 8.693 | 7.474 |
| CEBPB | 25.266 | 26.770 | 25.775 | 27.187 | 5.816 | 7.085 | 6.630 | 7.014 |
| COL4A2 | Undetermined | Undetermined | 34.328 | Undetermined | #VALUE! | #VALUE! | 15.183 | #VALUE! |
| CREB1 | 23.170 | 23.413 | 22.732 | 23.778 | 3.720 | 3.728 | 3.587 | 3.605 |
| CREB3 | 25.309 | 25.459 | 24.551 | 25.393 | 5.859 | 5.774 | 5.406 | 5.220 |
| CREB3L4 | 25.072 | 24.392 | 24.437 | 24.344 | 5.622 | 4.707 | 5.292 | 4.171 |
| CTGF | Undetermined | Undetermined | Undetermined | Undetermined | #VALUE! | #VALUE! | #VALUE! | #VALUE! |
| CYB561 | 36.874 | 31.478 | 32.971 | 33.799 | 17.424 | 11.793 | 13.826 | 13.626 |
| DDIT4 | 24.229 | 24.404 | 22.252 | 22.739 | 4.779 | 4.719 | 3.107 | 2.566 |
| DIRAS2 | Undetermined | Undetermined | Undetermined | Undetermined | #VALUE! | #VALUE! | #VALUE! | #VALUE! |
| DUSP1 | 25.679 | 27.284 | 25.828 | 26.552 | 6.229 | 7.599 | 6.683 | 6.379 |
| EDN1 | Undetermined | 26.349 | 30.819 | 26.407 | #VALUE! | 6.664 | 11.674 | 6.234 |
| EHD3 | 29.674 | 24.270 | 27.724 | 24.166 | 10.224 | 4.585 | 8.579 | 3.993 |
| ERRFI1 | Undetermined | 32.771 | Undetermined | 32.896 | #VALUE! | 13.086 | #VALUE! | 12.723 |
| FKBP5 | 22.873 | 23.267 | 21.321 | 21.824 | 3.423 | 3.582 | 2.176 | 1.651 |
| FOSL2 | 31.109 | 34.140 | 33.647 | 34.690 | 11.659 | 14.455 | 14.502 | 14.517 |
| GDPD1 | 28.371 | 27.494 | 28.235 | 27.303 | 8.921 | 7.809 | 9.090 | 7.130 |
| GHRHR | 34.636 | 39.957 | 37.789 | Undetermined | 15.186 | 20.272 | 18.644 | #VALUE! |
| GLUL | Undetermined | 28.395 | 31.475 | 30.591 | #VALUE! | 8.710 | 12.330 | 10.418 |
| GOT1 | 22.884 | 23.827 | 22.841 | 24.411 | 3.434 | 4.142 | 3.696 | 4.238 |
| H6PD | 26.360 | 25.976 | 26.197 | 25.435 | 6.910 | 6.291 | 7.052 | 5.262 |
| HAS2 | Undetermined | Undetermined | Undetermined | Undetermined | #VALUE! | #VALUE! | #VALUE! | #VALUE! |
| HNRPLL | 23.972 | 24.170 | 24.750 | 26.864 | 4.522 | 4.485 | 5.605 | 6.691 |
| IL10 | Undetermined | 34.229 | 34.306 | 35.010 | #VALUE! | 14.544 | 15.161 | 14.837 |
| IL1RN | 32.606 | 28.388 | 33.599 | 29.393 | 13.156 | 8.703 | 14.454 | 9.220 |
| IL6 | Undetermined | Undetermined | Undetermined | Undetermined | #VALUE! | #VALUE! | #VALUE! | #VALUE! |
| IL6R | Undetermined | 33.814 | Undetermined | Undetermined | #VALUE! | 14.129 | #VALUE! | #VALUE! |
| KLF13 | 24.539 | 23.800 | 23.792 | 23.671 | 5.089 | 4.115 | 4.647 | 3.498 |
| KLF9 | 30.841 | 28.881 | 30.105 | 28.187 | 11.391 | 9.196 | 10.960 | 8.014 |
| LOX | 34.266 | 34.399 | 34.511 | 34.207 | 14.816 | 14.714 | 15.366 | 14.034 |
| MERTK | Undetermined | 31.323 | 32.524 | Undetermined | #VALUE! | 11.638 | 13.379 | #VALUE! |
| MT1E | Undetermined | Undetermined | Undetermined | Undetermined | #VALUE! | #VALUE! | #VALUE! | #VALUE! |
| MT2A | 24.717 | 23.499 | 24.518 | 24.350 | 5.267 | 3.814 | 5.373 | 4.177 |
| NFKBIA | 22.371 | 23.807 | 22.895 | 23.454 | 2.921 | 4.122 | 3.750 | 3.281 |
| NR3C1 | 23.250 | 23.121 | 23.110 | 23.300 | 3.800 | 3.436 | 3.965 | 3.127 |
| PDCD7 | 24.179 | 24.740 | 23.874 | 25.248 | 4.729 | 5.055 | 4.729 | 5.075 |
| PDGFRB | Undetermined | Undetermined | Undetermined | Undetermined | #VALUE! | #VALUE! | #VALUE! | #VALUE! |
| PDP1 | 25.371 | 25.226 | 24.957 | 25.536 | 5.921 | 5.541 | 5.812 | 5.363 |
| PER1 | 25.109 | 25.820 | 24.989 | 26.651 | 5.659 | 6.135 | 5.844 | 6.478 |

TABLE 4c-continued

Ct values and fold changes from the RT2 Glucocorticoid signaling PCR array analysis for WSU cell line.

| | | | | | | | | |
|---|---|---|---|---|---|---|---|---|
| PER2 | 24.451 | 24.837 | 24.218 | 25.563 | 5.001 | 5.152 | 5.073 | 5.390 |
| PIK3R1 | 23.734 | 24.332 | 23.429 | 24.080 | 4.284 | 4.647 | 4.284 | 3.907 |
| PLD1 | Undetermined | Undetermined | 35.266 | Undetermined | #VALUE! | #VALUE! | 16.121 | #VALUE! |
| PLEKHF1 | 27.205 | 28.660 | 26.977 | 29.585 | 7.755 | 8.975 | 7.832 | 9.412 |
| POU2F1 | 24.234 | 24.671 | 24.368 | 24.732 | 4.784 | 4.986 | 5.223 | 4.559 |
| POU2F2 | 23.123 | 22.678 | 22.565 | 22.920 | 3.673 | 2.993 | 3.420 | 2.747 |
| RASA3 | 23.952 | 23.208 | 23.454 | 23.293 | 4.502 | 3.523 | 4.309 | 3.120 |
| RGS2 | 22.902 | 24.869 | 23.962 | 27.302 | 3.452 | 5.184 | 4.817 | 7.129 |
| RHOB | 29.724 | 27.234 | 28.803 | 27.392 | 10.274 | 7.549 | 9.658 | 7.219 |
| RHOJ | Undetermined | Undetermined | Undetermined | Undetermined | #VALUE! | #VALUE! | #VALUE! | #VALUE! |
| SESN1 | 28.689 | 25.215 | 25.915 | 21.378 | 9.239 | 5.530 | 6.770 | 1.205 |
| SGK1 | 25.579 | 28.624 | 27.309 | 30.174 | 6.129 | 8.939 | 8.164 | 10.001 |
| SLC10A6 | 36.617 | 35.684 | 37.200 | 39.653 | 17.167 | 15.999 | 18.055 | 19.480 |
| SLC19A2 | 26.638 | 26.125 | 25.887 | 26.101 | 7.188 | 6.440 | 6.742 | 5.928 |
| SLC22A5 | 28.901 | 26.640 | 29.427 | 27.488 | 9.451 | 6.955 | 10.282 | 7.315 |
| SNTA1 | 24.438 | 24.181 | 24.329 | 25.156 | 4.988 | 4.496 | 5.184 | 4.993 |
| SPHK1 | 29.643 | 29.333 | 29.804 | 29.702 | 10.193 | 9.648 | 10.659 | 9.529 |
| SPSB1 | 29.613 | 26.952 | 29.963 | 27.294 | 10.163 | 7.267 | 10.818 | 7.121 |
| STAT5A | 25.567 | 25.495 | 25.699 | 24.956 | 6.117 | 5.810 | 6.554 | 4.783 |
| STAT5B | 23.414 | 23.453 | 23.270 | 23.985 | 3.964 | 3.768 | 4.125 | 3.812 |
| TBL1XR1 | 21.602 | 22.111 | 21.479 | 22.588 | 2.152 | 2.426 | 2.334 | 2.415 |
| TNF | 23.694 | 25.079 | 24.151 | 25.675 | 4.244 | 5.394 | 5.006 | 5.502 |
| TNFAIP3 | 24.946 | 26.903 | 26.733 | 28.675 | 5.496 | 7.218 | 7.588 | 8.502 |
| TSC22D3 | 25.514 | 25.390 | 22.481 | 21.679 | 6.064 | 5.705 | 3.336 | 1.506 |
| USP2 | 22.646 | 21.903 | 20.884 | 20.640 | 3.196 | 2.218 | 1.739 | 0.467 |
| USP54 | 26.549 | 26.807 | 26.453 | 27.306 | 7.099 | 7.122 | 7.308 | 7.133 |
| VDR | 30.102 | 27.293 | 29.232 | 27.319 | 10.652 | 7.608 | 10.087 | 7.146 |
| VLDLR | 28.252 | 32.346 | 30.596 | Undetermined | 8.802 | 12.661 | 11.451 | #VALUE! |
| XDH | Undetermined | Undetermined | Undetermined | Undetermined | #VALUE! | #VALUE! | #VALUE! | #VALUE! |
| ZFP36 | 24.367 | 25.541 | 25.166 | 26.450 | 4.917 | 5.856 | 6.021 | 6.277 |
| ZHX3 | 25.774 | 24.831 | 25.570 | 25.485 | 6.324 | 5.146 | 6.425 | 5.312 |
| ZNF2B1 | 24.007 | 23.913 | 23.608 | 24.577 | 4.557 | 4.228 | 4.463 | 4.404 |
| ACTB | 14.801 | 15.450 | 14.572 | 16.143 | −4.649 | −4.235 | −4.573 | −4.030 |
| B2M | 19.450 | 19.685 | 19.145 | 20.173 | 0.000 | 0.000 | 0.000 | 0.000 |
| GAPDH | 16.528 | 17.275 | 16.349 | 17.416 | −2.922 | −2.410 | −2.796 | −2.757 |
| HPRT1 | 21.509 | 22.793 | 21.361 | 23.732 | 2.059 | 3.108 | 2.216 | 3.559 |
| RPLP0 | 15.697 | 15.681 | 15.330 | 15.349 | −3.753 | −4.004 | −3.815 | −4.824 |
| HGDC | Undetermined | Undetermined | Undetermined | Undetermined | #VALUE! | #VALUE! | #VALUE! | #VALUE! |
| RTC | 21.199 | 20.891 | 21.392 | 21.368 | 1.749 | 1.206 | 2.247 | 1.195 |
| RTC | 21.219 | 20.949 | 21.293 | 21.425 | 1.769 | 1.264 | 2.148 | 1.252 |
| RTC | 21.216 | 20.945 | 21.237 | 21.320 | 1.766 | 1.260 | 2.092 | 1.147 |
| PPC | 18.984 | 18.798 | 18.835 | 18.992 | −0.466 | −0.887 | −0.310 | −1.181 |
| PPC | 18.832 | 18.877 | 18.870 | 18.841 | −0.618 | −0.808 | −0.275 | −1.332 |
| PPC | 18.869 | 19.007 | 18.873 | 18.835 | −0.581 | −0.678 | −0.272 | −1.338 |

| | Cpd44 | | Pred | | Combo | |
|---|---|---|---|---|---|---|
| Gene | ΔΔCT | Fold Change | ΔΔCT | Fold Change | ΔΔCT | Fold Change |
| ADARB1 | −1.165 | 2.242 | 0.097 | 0.935 | −1.021 | 2.029 |
| AFF1 | −0.413 | 1.331 | −0.464 | 1.379 | −2.099 | 4.284 |
| AK2 | 0.486 | 0.714 | 0.094 | 0.937 | 0.702 | 0.615 |
| AMPD3 | −1.540 | 2.908 | −0.219 | 1.164 | −2.343 | 5.074 |
| ANGPTL4 | −1.192 | 2.285 | −0.329 | 1.256 | −0.657 | 1.577 |
| ANXA4 | −3.312 | 9.931 | −0.025 | 1.017 | −3.446 | 10.898 |
| AQP1 | #VALUE! | #VALUE! | #VALUE! | #VALUE! | #VALUE! | #VALUE! |
| ARID5B | −0.353 | 1.277 | 0.782 | 0.582 | 0.173 | 0.887 |
| ASPH | −0.105 | 1.075 | −0.041 | 1.029 | −0.174 | 1.128 |
| ATF4 | 0.361 | 0.779 | 0.090 | 0.940 | 0.274 | 0.827 |
| BCL6 | −0.394 | 1.314 | 0.249 | 0.841 | −0.544 | 1.458 |
| BMPER | #VALUE! | #VALUE! | #VALUE! | #VALUE! | −2.043 | 4.121 |
| CALCR | #VALUE! | #VALUE! | #VALUE! | #VALUE! | #VALUE! | #VALUE! |
| CEBPA | −1.659 | 3.158 | −0.295 | 1.227 | −1.514 | 2.856 |
| CEBPB | 1.269 | 0.415 | 0.814 | 0.569 | 1.198 | 0.436 |
| COL4A2 | #VALUE! | #VALUE! | #VALUE! | #VALUE! | #VALUE! | #VALUE! |
| CREB1 | 0.008 | 0.994 | −0.133 | 1.097 | −0.115 | 1.083 |
| CREB3 | −0.085 | 1.061 | −0.453 | 1.369 | −0.639 | 1.557 |
| CREB3L4 | −0.915 | 1.886 | −0.330 | 1.257 | −1.451 | 2.734 |
| CTGF | #VALUE! | #VALUE! | #VALUE! | #VALUE! | #VALUE! | #VALUE! |
| CYB561 | −5.631 | 49.556 | −3.598 | 12.109 | −3.798 | 13.910 |
| DDIT4 | −0.060 | 1.042 | −1.672 | 3.187 | −2.213 | 4.636 |
| DIRAS2 | #VALUE! | #VALUE! | #VALUE! | #VALUE! | #VALUE! | #VALUE! |
| DUSP1 | 1.370 | 0.387 | 0.454 | 0.730 | 0.150 | 0.901 |
| EDN1 | #VALUE! | #VALUE! | #VALUE! | #VALUE! | #VALUE! | #VALUE! |
| EHD3 | −5.639 | 49.832 | −1.645 | 3.127 | −6.231 | 75.113 |
| ERRFI1 | #VALUE! | #VALUE! | #VALUE! | #VALUE! | #VALUE! | #VALUE! |
| FKBP5 | 0.159 | 0.896 | −1.247 | 2.373 | −1.772 | 3.415 |
| FOSL2 | 2.796 | 0.144 | 2.843 | 0.139 | 2.858 | 0.138 |

TABLE 4c-continued

Ct values and fold changes from the RT2 Glucocorticoid signaling PCR array analysis for WSU cell line.

| | | | | | | |
|---|---|---|---|---|---|---|
| GDPD1 | −1.112 | 2.161 | 0.169 | 0.889 | −1.791 | 3.461 |
| GHRHR | 5.086 | 0.029 | 3.458 | 0.091 | #VALUE! | #VALUE! |
| GLUL | #VALUE! | #VALUE! | #VALUE! | #VALUE! | #VALUE! | #VALUE! |
| GOT1 | 0.708 | 0.612 | 0.262 | 0.834 | 0.804 | 0.573 |
| H6PD | −0.619 | 1.536 | 0.142 | 0.906 | −1.648 | 3.134 |
| HAS2 | #VALUE! | #VALUE! | #VALUE! | #VALUE! | #VALUE! | #VALUE! |
| HNRPLL | −0.037 | 1.026 | 1.083 | 0.472 | 2.169 | 0.222 |
| IL10 | #VALUE! | #VALUE! | #VALUE! | #VALUE! | #VALUE! | #VALUE! |
| IL1RN | −4.453 | 21.902 | 1.298 | 0.407 | −3.936 | 15.306 |
| IL6 | #VALUE! | #VALUE! | #VALUE! | #VALUE! | #VALUE! | #VALUE! |
| IL6R | #VALUE! | #VALUE! | #VALUE! | #VALUE! | #VALUE! | #VALUE! |
| KLF13 | −0.974 | 1.964 | −0.442 | 1.358 | −1.591 | 3.013 |
| KLF9 | −2.195 | 4.579 | −0.431 | 1.348 | −3.377 | 10.389 |
| LOX | −0.102 | 1.073 | 0.550 | 0.683 | −0.782 | 1.720 |
| MERTK | #VALUE! | #VALUE! | #VALUE! | #VALUE! | #VALUE! | #VALUE! |
| MT1E | #VALUE! | #VALUE! | #VALUE! | #VALUE! | #VALUE! | #VALUE! |
| MT2A | −1.453 | 2.738 | 0.106 | 0.929 | −1.090 | 2.129 |
| NFKBIA | 1.201 | 0.435 | 0.829 | 0.563 | 0.360 | 0.779 |
| NR3C1 | −0.364 | 1.287 | 0.165 | 0.892 | −0.673 | 1.594 |
| PDCD7 | 0.326 | 0.798 | 0.000 | 1.000 | 0.346 | 0.787 |
| PDGFRB | #VALUE! | #VALUE! | #VALUE! | #VALUE! | #VALUE! | #VALUE! |
| PDP1 | −0.380 | 1.301 | −0.109 | 1.078 | −0.558 | 1.472 |
| PER1 | 0.476 | 0.719 | 0.185 | 0.880 | 0.819 | 0.567 |
| PER2 | 0.151 | 0.901 | 0.072 | 0.951 | 0.389 | 0.764 |
| PIK3R1 | 0.363 | 0.778 | 0.000 | 1.000 | −0.377 | 1.299 |
| PLD1 | #VALUE! | #VALUE! | #VALUE! | #VALUE! | #VALUE! | #VALUE! |
| PLEKHF1 | 1.220 | 0.429 | 0.077 | 0.948 | 1.657 | 0.317 |
| POU2F1 | 0.202 | 0.869 | 0.439 | 0.738 | −0.225 | 1.169 |
| POU2F2 | −0.680 | 1.602 | −0.253 | 1.192 | −0.926 | 1.900 |
| RASA3 | −0.979 | 1.971 | −0.193 | 1.143 | −1.382 | 2.606 |
| RGS2 | 1.732 | 0.301 | 1.365 | 0.388 | 3.677 | 0.078 |
| RHOB | −2.725 | 6.612 | −0.616 | 1.533 | −3.055 | 8.311 |
| RHOJ | #VALUE! | #VALUE! | #VALUE! | #VALUE! | #VALUE! | #VALUE! |
| SESN1 | −3.709 | 13.077 | −2.469 | 5.537 | −8.034 | 262.105 |
| SGK1 | 2.810 | 0.143 | 2.035 | 0.244 | 3.872 | 0.068 |
| SLC10A6 | −1.168 | 2.247 | 0.888 | 0.540 | 2.313 | 0.201 |
| SLC19A2 | −0.748 | 1.679 | −0.446 | 1.362 | −1.260 | 2.395 |
| SLC22A5 | −2.496 | 5.641 | 0.831 | 0.562 | −2.136 | 4.395 |
| SNTA1 | −0.492 | 1.406 | 0.196 | 0.873 | 0.005 | 0.997 |
| SPHK1 | −0.545 | 1.459 | 0.466 | 0.724 | −0.664 | 1.584 |
| SPSB1 | −2.896 | 7.444 | 0.655 | 0.635 | −3.042 | 8.236 |
| STAT5A | −0.307 | 1.237 | 0.437 | 0.739 | −1.334 | 2.521 |
| STAT5B | −0.196 | 1.146 | 0.161 | 0.894 | −0.152 | 1.111 |
| TBL1XR1 | 0.274 | 0.827 | 0.182 | 0.881 | 0.263 | 0.833 |
| TNF | 1.150 | 0.451 | 0.762 | 0.590 | 1.258 | 0.418 |
| TNFAIP3 | 1.722 | 0.303 | 2.092 | 0.235 | 3.006 | 0.124 |
| TSC22D3 | −0.359 | 1.283 | −2.728 | 6.625 | −4.558 | 23.556 |
| USP2 | −0.978 | 1.970 | −1.457 | 2.745 | −2.729 | 6.630 |
| USP54 | 0.023 | 0.984 | 0.209 | 0.865 | 0.034 | 0.977 |
| VDR | −3.044 | 8.248 | −0.565 | 1.479 | −3.506 | 11.361 |
| VLDLR | 3.859 | 0.069 | 2.649 | 0.159 | #VALUE! | #VALUE! |
| XDH | #VALUE! | #VALUE! | #VALUE! | #VALUE! | #VALUE! | #VALUE! |
| ZFP36 | 0.939 | 0.522 | 1.104 | 0.465 | 1.360 | 0.390 |
| ZHX3 | −1.178 | 2.263 | 0.101 | 0.932 | −1.012 | 2.017 |
| ZNF281 | −0.329 | 1.256 | −0.094 | 1.067 | −0.153 | 1.112 |
| ACTB | | | | | | |
| B2M | | | | | | |
| GAPDH | | | | | | |
| HPRT1 | | | | | | |
| RPLP0 | | | | | | |
| HGDC | | | | | | |
| RTC | | | | | | |
| RTC | | | | | | |
| RTC | | | | | | |
| PPC | | | | | | |
| PPC | | | | | | |
| PPC | | | | | | |

TABLE 4d

Ct values and fold changes from the RT2 Glucocorticoid signaling PCR array analysis for SUDHL10 cell line.

| | Ct Values | | | | ΔCT (B2M) | | | |
|---|---|---|---|---|---|---|---|---|
| Gene | DMSO | Cpd44 | Pred | Combo | DMSO | Cpd44 | Pred | Combo |
| ADARB1 | 30.421 | 31.215 | 31.883 | 32.846 | 11.995 | 12.068 | 14.229 | 14.012 |
| AFF1 | 28.478 | 29.849 | 27.600 | 27.812 | 10.052 | 10.702 | 9.946 | 8.978 |
| AK2 | 20.354 | 20.974 | 19.237 | 20.672 | 1.928 | 1.827 | 1.583 | 1.838 |
| AMPD3 | 27.489 | 27.654 | 26.390 | 27.563 | 9.063 | 8.507 | 8.736 | 8.729 |
| ANGPTL4 | 30.771 | 32.107 | 29.894 | 31.412 | 12.345 | 12.960 | 12.240 | 12.578 |
| ANXA4 | 26.715 | 24.961 | 25.942 | 24.755 | 8.289 | 5.814 | 8.288 | 5.921 |
| AQP1 | Undetermined | Undetermined | Undetermined | Undetermined | #VALUE! | #VALUE! | #VALUE! | #VALUE! |
| ARID5B | 26.837 | 28.208 | 27.668 | 27.409 | 8.411 | 9.061 | 10.014 | 8.575 |
| ASPH | 22.820 | 23.837 | 22.217 | 24.322 | 4.394 | 4.690 | 4.563 | 5.488 |
| ATF4 | 18.149 | 20.607 | 18.947 | 20.429 | −0.277 | 1.460 | 1.293 | 1.595 |
| BCL6 | 21.278 | 22.639 | 21.573 | 23.181 | 2.852 | 3.492 | 3.919 | 4.347 |
| BMPER | Undetermined | Undetermined | Undetermined | Undetermined | #VALUE! | #VALUE! | #VALUE! | #VALUE! |
| CALCR | Undetermined | Undetermined | Undetermined | Undetermined | #VALUE! | #VALUE! | #VALUE! | #VALUE! |
| CEBPA | 29.205 | 28.900 | 29.217 | 28.372 | 10.779 | 9.753 | 11.563 | 9.538 |
| CEBPB | 22.884 | 26.624 | 24.539 | 25.652 | 4.458 | 7.477 | 6.885 | 6.818 |
| COL4A2 | Undetermined | Undetermined | 35.603 | 34.161 | #VALUE! | #VALUE! | 17.949 | 15.327 |
| CREB1 | 23.139 | 23.809 | 22.395 | 23.638 | 4.713 | 4.662 | 4.741 | 4.804 |
| CREB3 | 25.310 | 26.452 | 24.440 | 25.398 | 6.884 | 7.305 | 6.786 | 6.564 |
| CREB3L4 | 24.612 | 26.139 | 24.960 | 26.248 | 6.186 | 6.992 | 7.306 | 7.414 |
| CTGF | Undetermined | Undetermined | Undetermined | Undetermined | #VALUE! | #VALUE! | #VALUE! | #VALUE! |
| CYB561 | 38.682 | 37.004 | 38.074 | 38.165 | 20.256 | 17.857 | 20.420 | 19.331 |
| DDIT4 | 23.944 | 26.109 | 21.960 | 21.759 | 5.518 | 6.962 | 4.306 | 2.925 |
| DIRAS2 | Undetermined | Undetermined | Undetermined | Undetermined | #VALUE! | #VALUE! | #VALUE! | #VALUE! |
| DUSP1 | 29.480 | 31.300 | 27.989 | 28.385 | 11.054 | 12.153 | 10.335 | 9.551 |
| EDN1 | Undetermined | Undetermined | Undetermined | Undetermined | #VALUE! | #VALUE! | #VALUE! | #VALUE! |
| EHD3 | 26.932 | 26.768 | 25.888 | 25.803 | 8.506 | 7.621 | 8.234 | 6.969 |
| ERRFI1 | Undetermined | Undetermined | Undetermined | Undetermined | #VALUE! | #VALUE! | #VALUE! | #VALUE! |
| FKBP5 | 22.120 | 22.883 | 19.749 | 20.675 | 3.694 | 3.736 | 2.095 | 1.841 |
| FOSL2 | 32.273 | 32.931 | 29.990 | 30.849 | 13.847 | 13.784 | 12.336 | 12.015 |
| GDPD1 | 31.627 | 30.943 | 29.917 | 30.011 | 13.201 | 11.796 | 12.263 | 11.177 |
| GHRHR | Undetermined | Undetermined | 36.757 | Undetermined | #VALUE! | #VALUE! | 19.103 | #VALUE! |
| GLUL | 33.940 | Undetermined | Undetermined | Undetermined | 15.514 | #VALUE! | #VALUE! | #VALUE! |
| GOT1 | 23.510 | 25.306 | 23.519 | 24.803 | 5.084 | 6.159 | 5.865 | 5.969 |
| H6PD | 26.184 | 28.126 | 26.256 | 26.915 | 7.758 | 8.979 | 8.602 | 8.081 |
| HAS2 | Undetermined | Undetermined | Undetermined | Undetermined | #VALUE! | #VALUE! | #VALUE! | #VALUE! |
| HNRPLL | 22.972 | 23.764 | 22.692 | 24.016 | 4.546 | 4.617 | 5.038 | 5.182 |
| IL10 | Undetermined | 32.505 | Undetermined | 32.875 | #VALUE! | 13.358 | #VALUE! | 14.041 |
| IL1RN | Undetermined | 32.182 | Undetermined | Undetermined | #VALUE! | 13.035 | #VALUE! | #VALUE! |
| IL6 | Undetermined | Undetermined | Undetermined | Undetermined | #VALUE! | #VALUE! | #VALUE! | #VALUE! |
| IL6R | Undetermined | 33.807 | 33.801 | Undetermined | #VALUE! | 14.660 | 16.147 | #VALUE! |
| KLF13 | 25.451 | 24.536 | 22.488 | 22.832 | 7.025 | 5.389 | 4.834 | 3.998 |
| KLF9 | 32.931 | 32.525 | 30.255 | 29.691 | 14.505 | 13.378 | 12.601 | 10.857 |
| LOX | 33.500 | 35.385 | 32.223 | 32.465 | 15.074 | 16.238 | 14.569 | 13.631 |
| MERTK | Undetermined | 34.652 | Undetermined | 33.161 | #VALUE! | 15.505 | #VALUE! | 14.327 |
| MT1E | Undetermined | Undetermined | Undetermined | 34.503 | #VALUE! | #VALUE! | #VALUE! | 15.669 |
| MT2A | 34.844 | 37.225 | 35.909 | 35.849 | 16.418 | 18.078 | 18.255 | 17.015 |
| NFKBIA | 22.331 | 23.654 | 21.628 | 22.744 | 3.905 | 4.507 | 3.974 | 3.910 |
| NR3C1 | 22.516 | 23.754 | 22.000 | 22.835 | 4.090 | 4.617 | 4.346 | 4.001 |
| PDCD7 | 23.600 | 25.123 | 23.256 | 24.731 | 5.174 | 5.976 | 5.602 | 5.897 |
| PDGFRB | Undetermined | Undetermined | Undetermined | Undetermined | #VALUE! | #VALUE! | #VALUE! | #VALUE! |
| PDP1 | 25.438 | 26.175 | 25.178 | 26.259 | 7.012 | 7.028 | 7.524 | 7.425 |
| PER1 | 26.209 | 27.710 | 24.762 | 26.686 | 7.783 | 8.563 | 7.108 | 7.852 |
| PER2 | 23.618 | 24.780 | 22.642 | 24.465 | 5.192 | 5.633 | 4.988 | 5.631 |
| PIK3R1 | 23.509 | 24.661 | 22.697 | 23.585 | 5.083 | 5.514 | 5.043 | 4.751 |
| PLD1 | Undetermined | Undetermined | Undetermined | Undetermined | #VALUE! | #VALUE! | #VALUE! | #VALUE! |
| PLEKHF1 | 27.789 | 28.979 | 26.691 | 27.331 | 9.363 | 9.832 | 9.037 | 8.497 |
| POU2F1 | 25.115 | 25.842 | 24.283 | 24.827 | 6.689 | 6.695 | 6.629 | 5.993 |
| POU2F2 | 23.953 | 25.098 | 22.977 | 24.098 | 5.527 | 5.951 | 5.323 | 5.264 |
| RASA3 | 23.171 | 24.277 | 22.449 | 23.649 | 4.745 | 5.130 | 4.795 | 4.815 |
| RGS2 | 24.794 | 25.587 | 25.390 | 26.161 | 6.368 | 6.440 | 7.736 | 7.327 |
| RHOB | 28.583 | 27.829 | 27.968 | 26.383 | 10.157 | 8.682 | 10.314 | 7.549 |
| RHOJ | Undetermined | 36.530 | Undetermined | Undetermined | #VALUE! | 17.383 | #VALUE! | #VALUE! |
| SESN1 | 28.405 | 27.480 | 24.220 | 22.646 | 9.979 | 8.333 | 6.566 | 3.812 |
| SGK1 | 22.694 | 25.358 | 22.897 | 24.642 | 4.268 | 6.211 | 5.243 | 5.808 |
| SLC10A6 | 36.987 | 37.060 | 34.670 | 36.258 | 18.561 | 17.913 | 17.016 | 17.424 |
| SLC19A2 | 31.019 | 30.597 | 31.940 | 31.354 | 12.593 | 11.450 | 14.286 | 12.520 |
| SLC22A5 | 31.275 | 30.263 | 32.426 | 29.324 | 12.849 | 11.116 | 14.772 | 10.490 |
| SNTA1 | 25.751 | 27.003 | 24.913 | 26.374 | 7.325 | 7.856 | 7.259 | 7.540 |
| SPHK1 | 26.852 | 27.804 | 25.801 | 27.082 | 8.426 | 8.657 | 8.147 | 8.248 |
| SPSB1 | 25.856 | 26.133 | 24.455 | 24.642 | 7.430 | 6.986 | 6.801 | 5.808 |
| STAT5A | 24.170 | 25.275 | 23.779 | 24.550 | 5.744 | 6.128 | 6.125 | 5.716 |
| STAT5B | 23.533 | 24.281 | 23.480 | 24.231 | 5.107 | 5.134 | 5.826 | 5.397 |
| TBL1XR1 | 20.891 | 21.846 | 20.224 | 21.815 | 2.465 | 2.699 | 2.570 | 2.981 |
| TNF | 23.208 | 23.725 | 22.657 | 24.669 | 4.782 | 4.578 | 5.003 | 5.835 |

TABLE 4d-continued

Ct values and fold changes from the RT2 Glucocorticoid signaling PCR array analysis for SUDHL10 cell line.

| | | | | | | | | |
|---|---|---|---|---|---|---|---|---|
| TNFAIP3 | 26.832 | 27.677 | 27.010 | 26.749 | 8.406 | 8.530 | 9.356 | 7.915 |
| TSC22D3 | 25.441 | 28.871 | 23.160 | 22.809 | 7.015 | 9.724 | 5.506 | 3.975 |
| USP2 | 22.643 | 23.434 | 21.579 | 22.360 | 4.217 | 4.287 | 3.925 | 3.526 |
| USP54 | 27.132 | 27.789 | 26.401 | 27.379 | 8.706 | 8.642 | 8.747 | 8.545 |
| VDR | 29.507 | 29.514 | 28.490 | 28.525 | 11.081 | 10.367 | 10.836 | 9.691 |
| VLDLR | 27.937 | 32.904 | 31.762 | 32.093 | 9.511 | 13.757 | 14.108 | 13.259 |
| XDH | Undetermined | Undetermined | Undetermined | Undetermined | #VALUE! | #VALUE! | #VALUE! | #VALUE! |
| ZFP36 | 25.707 | 26.643 | 24.515 | 25.887 | 7.281 | 7.496 | 6.861 | 7.053 |
| ZHX3 | 26.753 | 26.305 | 26.008 | 26.393 | 8.327 | 7.158 | 8.354 | 7.559 |
| ZNF2B1 | 23.573 | 23.857 | 22.336 | 23.665 | 5.147 | 4.710 | 4.682 | 4.831 |
| ACTB | 14.330 | 14.828 | 13.138 | 14.548 | −4.096 | −4.319 | −4.516 | −4.286 |
| B2M | 18.426 | 19.147 | 17.654 | 18.834 | 0.000 | 0.000 | 0.000 | 0.000 |
| GAPDH | 16.544 | 17.793 | 15.669 | 16.935 | −1.882 | −1.354 | −1.985 | −1.899 |
| HPRT1 | 19.452 | 20.615 | 18.679 | 20.706 | 1.026 | 1.468 | 1.025 | 1.872 |
| RPLP0 | 15.746 | 16.821 | 15.169 | 15.785 | −2.680 | −2.326 | −2.485 | −3.049 |
| HGDC | Undetermined | Undetermined | Undetermined | Undetermined | #VALUE! | #VALUE! | #VALUE! | #VALUE! |
| RTC | 22.619 | 22.346 | 22.496 | 23.181 | 4.193 | 3.199 | 4.842 | 4.347 |
| RTC | 22.626 | 22.362 | 22.621 | 23.201 | 4.200 | 3.215 | 4.967 | 4.367 |
| RTC | 22.662 | 22.313 | 22.484 | 23.114 | 4.236 | 3.166 | 4.830 | 4.280 |
| PPC | 18.253 | 18.442 | 17.960 | 18.476 | −0.173 | −0.705 | 0.306 | −0.358 |
| PPC | 18.527 | 18.474 | 18.434 | 18.446 | 0.101 | −0.673 | 0.780 | −0.388 |
| PPC | 18.410 | 18.623 | 18.515 | 18.482 | −0.016 | −0.524 | 0.861 | −0.352 |

| | Cpd44 | | Pred | | Combo | |
|---|---|---|---|---|---|---|
| Gene | ΔΔCT | Fold Change | ΔΔCT | Fold Change | ΔΔCT | Fold Change |
| ADARB1 | 0.073 | 0.951 | 2.234 | 0.213 | 2.017 | 0.247 |
| AFF1 | 0.650 | 0.637 | −0.106 | 1.076 | −1.074 | 2.105 |
| AK2 | −0.101 | 1.073 | −0.345 | 1.270 | −0.090 | 1.064 |
| AMPD3 | −0.556 | 1.470 | −0.327 | 1.254 | −0.334 | 1.261 |
| ANGPTL4 | 0.615 | 0.653 | −0.105 | 1.075 | 0.233 | 0.851 |
| ANXA4 | −2.475 | 5.560 | −0.001 | 1.001 | −2.368 | 5.162 |
| AQP1 | #VALUE! | #VALUE! | #VALUE! | #VALUE! | #VALUE! | #VALUE! |
| ARID5B | 0.650 | 0.637 | 1.603 | 0.329 | 0.164 | 0.893 |
| ASPH | 0.296 | 0.815 | 0.169 | 0.889 | 1.094 | 0.468 |
| ATF4 | 1.737 | 0.300 | 1.570 | 0.337 | 1.872 | 0.273 |
| BCL6 | 0.640 | 0.642 | 1.067 | 0.477 | 1.495 | 0.355 |
| BMPER | #VALUE! | #VALUE! | #VALUE! | #VALUE! | #VALUE! | #VALUE! |
| CALCR | #VALUE! | #VALUE! | #VALUE! | #VALUE! | #VALUE! | #VALUE! |
| CEBPA | −1.026 | 2.036 | 0.784 | 0.581 | −1.241 | 2.364 |
| CEBPB | 3.019 | 0.123 | 2.427 | 0.186 | 2.360 | 0.195 |
| COL4A2 | #VALUE! | #VALUE! | #VALUE! | #VALUE! | #VALUE! | #VALUE! |
| CREB1 | −0.051 | 1.036 | 0.028 | 0.981 | 0.091 | 0.939 |
| CREB3 | 0.421 | 0.747 | −0.098 | 1.070 | −0.320 | 1.248 |
| CREB3L4 | 0.806 | 0.572 | 1.120 | 0.460 | 1.228 | 0.427 |
| CTGF | #VALUE! | #VALUE! | #VALUE! | #VALUE! | #VALUE! | #VALUE! |
| CYB561 | −2.399 | 5.274 | 0.164 | 0.893 | −0.925 | 1.899 |
| DDIT4 | 1.444 | 0.368 | −1.212 | 2.317 | −2.593 | 6.034 |
| DIRAS2 | #VALUE! | #VALUE! | #VALUE! | #VALUE! | #VALUE! | #VALUE! |
| DUSP1 | 1.099 | 0.467 | −0.719 | 1.646 | −1.503 | 2.834 |
| EDN1 | #VALUE! | #VALUE! | #VALUE! | #VALUE! | #VALUE! | #VALUE! |
| EHD3 | −0.885 | 1.847 | −0.272 | 1.207 | −1.537 | 2.902 |
| ERRFI1 | #VALUE! | #VALUE! | #VALUE! | #VALUE! | #VALUE! | #VALUE! |
| FKBP5 | 0.042 | 0.971 | −1.599 | 3.029 | −1.853 | 3.613 |
| FOSL2 | −0.063 | 1.045 | −1.511 | 2.850 | −1.832 | 3.560 |
| GDPD1 | −1.405 | 2.648 | −0.938 | 1.916 | −2.024 | 4.067 |
| GHRHR | #VALUE! | #VALUE! | #VALUE! | #VALUE! | #VALUE! | #VALUE! |
| GLUL | #VALUE! | #VALUE! | #VALUE! | #VALUE! | #VALUE! | #VALUE! |
| GOT1 | 1.075 | 0.475 | 0.781 | 0.582 | 0.885 | 0.541 |
| H6PD | 1.221 | 0.429 | 0.844 | 0.557 | 0.323 | 0.799 |
| HAS2 | #VALUE! | #VALUE! | #VALUE! | #VALUE! | #VALUE! | #VALUE! |
| HNRPLL | 0.071 | 0.952 | 0.492 | 0.711 | 0.636 | 0.643 |
| IL10 | #VALUE! | #VALUE! | #VALUE! | #VALUE! | #VALUE! | #VALUE! |
| IL1RN | #VALUE! | #VALUE! | #VALUE! | #VALUE! | #VALUE! | #VALUE! |
| IL6 | #VALUE! | #VALUE! | #VALUE! | #VALUE! | #VALUE! | #VALUE! |
| IL6R | #VALUE! | #VALUE! | #VALUE! | #VALUE! | #VALUE! | #VALUE! |
| KLF13 | −1.636 | 3.108 | −2.191 | 4.566 | −3.027 | 8.151 |
| KLF9 | −1.127 | 2.184 | −1.904 | 3.742 | −3.648 | 12.536 |
| LOX | 1.164 | 0.446 | −0.505 | 1.419 | −1.443 | 2.719 |
| MERTK | #VALUE! | #VALUE! | #VALUE! | #VALUE! | #VALUE! | #VALUE! |
| MT1E | #VALUE! | #VALUE! | #VALUE! | #VALUE! | #VALUE! | #VALUE! |
| MT2A | 1.660 | 0.316 | 1.837 | 0.280 | 0.597 | 0.661 |
| NFKBIA | 0.602 | 0.659 | 0.069 | 0.953 | 0.005 | 0.997 |
| NR3C1 | 0.527 | 0.694 | 0.256 | 0.837 | −0.089 | 1.064 |
| PDCD7 | 0.802 | 0.574 | 0.428 | 0.743 | 0.723 | 0.606 |
| PDGFRB | #VALUE! | #VALUE! | #VALUE! | #VALUE! | #VALUE! | #VALUE! |
| PDP1 | 0.016 | 0.989 | 0.512 | 0.701 | 0.413 | 0.751 |

TABLE 4d-continued

Ct values and fold changes from the RT2 Glucocorticoid signaling PCR array analysis for SUDHL10 cell line.

|  |  |  |  |  |  |  |
|---|---|---|---|---|---|---|
| PER1 | 0.780 | 0.582 | −0.675 | 1.597 | 0.069 | 0.953 |
| PER2 | 0.441 | 0.737 | −0.204 | 1.152 | 0.439 | 0.738 |
| PIK3R1 | 0.431 | 0.742 | −0.040 | 1.028 | −0.332 | 1.259 |
| PLD1 | #VALUE! | #VALUE! | #VALUE! | #VALUE! | #VALUE! | #VALUE! |
| PLEKHF1 | 0.469 | 0.722 | −0.326 | 1.254 | −0.866 | 1.823 |
| POU2F1 | 0.006 | 0.996 | −0.060 | 1.042 | −0.696 | 1.620 |
| POU2F2 | 0.424 | 0.745 | −0.204 | 1.152 | −0.263 | 1.200 |
| RASA3 | 0.385 | 0.766 | 0.050 | 0.966 | 0.070 | 0.953 |
| RGS2 | 0.072 | 0.951 | 1.368 | 0.387 | 0.959 | 0.514 |
| RHOB | −1.475 | 2.780 | 0.157 | 0.897 | −2.608 | 6.097 |
| RHOJ | #VALUE! | #VALUE! | #VALUE! | #VALUE! | #VALUE! | #VALUE! |
| SESN1 | −1.646 | 3.130 | −3.413 | 10.652 | −6.167 | 71.854 |
| SGK1 | 1.943 | 0.260 | 0.975 | 0.509 | 1.540 | 0.344 |
| SLC10A6 | −0.648 | 1.567 | −1.545 | 2.918 | −1.137 | 2.199 |
| SLC19A2 | −1.143 | 2.208 | 1.693 | 0.309 | −0.073 | 1.052 |
| SLC22A5 | −1.733 | 3.324 | 1.923 | 0.264 | −2.359 | 5.130 |
| SNTA1 | 0.531 | 0.692 | −0.066 | 1.047 | 0.215 | 0.862 |
| SPHK1 | 0.231 | 0.852 | −0.279 | 1.213 | −0.178 | 1.131 |
| SPSB1 | −0.444 | 1.360 | −0.629 | 1.546 | −1.622 | 3.078 |
| STAT5A | 0.384 | 0.766 | 0.381 | 0.768 | −0.028 | 1.020 |
| STAT5B | 0.027 | 0.981 | 0.719 | 0.608 | 0.290 | 0.818 |
| TBL1XR1 | 0.234 | 0.850 | 0.105 | 0.930 | 0.516 | 0.699 |
| TNF | −0.204 | 1.152 | 0.221 | 0.858 | 1.053 | 0.482 |
| TNFAIP3 | 0.124 | 0.918 | 0.950 | 0.518 | −0.491 | 1.405 |
| TSC22D3 | 2.709 | 0.153 | −1.509 | 2.846 | −3.040 | 8.225 |
| USP2 | 0.070 | 0.953 | −0.292 | 1.224 | −0.691 | 1.614 |
| USP54 | −0.064 | 1.045 | 0.041 | 0.972 | −0.161 | 1.118 |
| VDR | −0.714 | 1.640 | −0.245 | 1.185 | −1.390 | 2.621 |
| VLDLR | 4.246 | 0.053 | 4.597 | 0.041 | 3.748 | 0.074 |
| XDH | #VALUE! | #VALUE! | #VALUE! | #VALUE! | #VALUE! | #VALUE! |
| ZFP36 | 0.215 | 0.862 | −0.420 | 1.338 | −0.228 | 1.171 |
| ZHX3 | −1.169 | 2.249 | 0.027 | 0.981 | −0.768 | 1.703 |
| ZNF281 | −0.437 | 1.354 | −0.465 | 1.380 | −0.316 | 1.245 |
| ACTB |  |  |  |  |  |  |
| B2M |  |  |  |  |  |  |
| GAPDH |  |  |  |  |  |  |
| HPRT1 |  |  |  |  |  |  |
| RPLP0 |  |  |  |  |  |  |
| HGDC |  |  |  |  |  |  |
| RTC |  |  |  |  |  |  |
| RTC |  |  |  |  |  |  |
| RTC |  |  |  |  |  |  |
| PPC |  |  |  |  |  |  |
| PPC |  |  |  |  |  |  |
| PPC |  |  |  |  |  |  |

TABLE 4e

Ct values and fold changes from the RT2 Glucocorticoid signaling PCR array analysis for RI cell line.

| Gene | Ct Values | | | | ΔCT (B2M) | | | |
|---|---|---|---|---|---|---|---|---|
|  | DMSO | Cpd44 | Pred | Combo | DMSO | Cpd44 | Pred | Combo |
| ADARB1 | 27.745 | 26.650 | 28.557 | 28.623 | 8.964 | 7.292 | 9.377 | 9.377 |
| AFF1 | 28.249 | 26.820 | 27.258 | 26.977 | 9.468 | 7.462 | 8.078 | 7.731 |
| AK2 | 19.425 | 20.270 | 20.510 | 21.466 | 0.644 | 0.912 | 1.330 | 2.220 |
| AMPD3 | 27.499 | 27.191 | 27.354 | 27.238 | 8.718 | 7.833 | 8.174 | 7.992 |
| ANGPTL4 | 30.178 | 29.820 | 32.245 | 29.596 | 11.397 | 10.462 | 13.065 | 10.350 |
| ANXA4 | 24.380 | 24.395 | 24.910 | 24.771 | 5.599 | 5.037 | 5.730 | 5.525 |
| AQP1 | Undetermined | Undetermined | Undetermined | 33.328 | #VALUE! | #VALUE! | #VALUE! | 14.082 |
| ARID5B | 27.976 | 27.333 | 29.208 | 28.495 | 9.195 | 7.975 | 10.028 | 9.249 |
| ASPH | 22.413 | 23.466 | 23.583 | 24.410 | 3.632 | 4.108 | 4.403 | 5.164 |
| ATF4 | 17.689 | 18.269 | 19.452 | 20.540 | −1.092 | −1.089 | 0.272 | 1.294 |
| BCL6 | 19.449 | 20.289 | 20.785 | 20.772 | 0.668 | 0.931 | 1.605 | 1.526 |
| BMPER | Undetermined | Undetermined | Undetermined | Undetermined | #VALUE! | #VALUE! | #VALUE! | #VALUE! |
| CALCR | Undetermined | Undetermined | Undetermined | Undetermined | #VALUE! | #VALUE! | #VALUE! | #VALUE! |
| CEBPA | Undetermined | 36.511 | Undetermined | Undetermined | #VALUE! | 17.153 | #VALUE! | #VALUE! |
| CEBPB | 23.192 | 23.765 | 26.229 | 27.211 | 4.411 | 4.407 | 7.049 | 7.965 |
| COL4A2 | 31.978 | 31.782 | Undetermined | 35.212 | 13.197 | 12.424 | #VALUE! | 15.966 |
| CREB1 | 22.435 | 23.217 | 23.317 | 23.470 | 3.654 | 3.859 | 4.137 | 4.224 |
| CREB3 | 23.790 | 24.178 | 24.951 | 24.735 | 5.009 | 4.820 | 5.771 | 5.489 |
| CREB3L4 | 23.683 | 23.500 | 24.211 | 23.870 | 4.902 | 4.142 | 5.031 | 4.624 |
| CTGF | Undetermined | Undetermined | Undetermined | Undetermined | #VALUE! | #VALUE! | #VALUE! | #VALUE! |
| CYB561 | 39.352 | 38.452 | 38.088 | 37.618 | 20.571 | 19.094 | 18.908 | 18.372 |

TABLE 4e-continued

Ct values and fold changes from the RT2 Glucocorticoid signaling PCR array analysis for RI cell line.

| | | | | | | | | |
|---|---|---|---|---|---|---|---|---|
| DDIT4 | 21.641 | 22.679 | 23.471 | 22.583 | 2.860 | 3.321 | 4.291 | 3.337 |
| DIRAS2 | Undetermined | Undetermined | Undetermined | Undetermined | #VALUE! | #VALUE! | #VALUE! | #VALUE! |
| DUSP1 | 25.166 | 25.422 | 25.412 | 24.981 | 6.385 | 6.064 | 6.232 | 5.735 |
| EDN1 | 32.446 | 31.815 | 39.440 | 30.700 | 13.665 | 12.457 | 20.260 | 11.454 |
| EHD3 | 24.957 | 24.572 | 25.411 | 23.975 | 6.176 | 5.214 | 6.231 | 4.729 |
| ERRFI1 | Undetermined | 31.705 | 32.655 | 31.791 | #VALUE! | 12.347 | 13.475 | 12.545 |
| FKBP5 | 20.792 | 21.757 | 20.858 | 20.881 | 2.011 | 2.399 | 1.678 | 1.635 |
| FOSL2 | 31.458 | 30.761 | 34.157 | 36.459 | 12.677 | 11.403 | 14.977 | 17.213 |
| GDPD1 | 27.589 | 27.394 | 28.699 | 28.110 | 8.808 | 8.036 | 9.519 | 8.864 |
| GHRHR | Undetermined | 37.546 | 33.555 | 29.797 | #VALUE! | 18.188 | 14.375 | 10.551 |
| GLUL | 30.775 | 28.738 | 32.181 | 32.961 | 11.994 | 9.380 | 13.001 | 13.715 |
| GOT1 | 21.489 | 22.584 | 23.355 | 24.551 | 2.708 | 3.226 | 4.175 | 5.305 |
| H6PD | 25.108 | 25.012 | 26.442 | 24.742 | 6.327 | 5.654 | 7.262 | 5.496 |
| HAS2 | Undetermined | Undetermined | Undetermined | Undetermined | #VALUE! | #VALUE! | #VALUE! | #VALUE! |
| HNRPLL | 21.958 | 22.844 | 23.146 | 24.289 | 3.177 | 3.486 | 3.966 | 5.043 |
| IL10 | 32.353 | 31.498 | 32.669 | Undetermined | 13.572 | 12.140 | 13.489 | #VALUE! |
| IL1RN | 29.709 | 28.405 | 29.300 | 29.204 | 10.928 | 9.047 | 10.120 | 9.958 |
| IL6 | Undetermined | Undetermined | Undetermined | Undetermined | #VALUE! | #VALUE! | #VALUE! | #VALUE! |
| IL6R | 29.184 | 29.246 | 30.468 | 31.321 | 10.403 | 9.888 | 11.288 | 12.075 |
| KLF13 | 22.843 | 22.854 | 23.590 | 23.322 | 4.062 | 3.496 | 4.410 | 4.076 |
| KLF9 | 34.469 | Undetermined | Undetermined | Undetermined | 15.688 | #VALUE! | #VALUE! | #VALUE! |
| LOK | 33.918 | 33.915 | 34.185 | 33.948 | 15.137 | 14.557 | 15.005 | 14.702 |
| MERTK | 34.533 | 30.691 | Undetermined | 31.272 | 15.752 | 11.333 | #VALUE! | 12.026 |
| MT1E | Undetermined | 34.215 | Undetermined | Undetermined | #VALUE! | 14.857 | #VALUE! | #VALUE! |
| MT2A | 23.125 | 24.279 | 25.180 | 25.570 | 4.344 | 4.921 | 6.000 | 6.324 |
| NFKBIA | 22.279 | 23.710 | 23.531 | 23.442 | 3.498 | 4.352 | 4.351 | 4.196 |
| NR3C1 | 21.972 | 22.616 | 23.323 | 23.237 | 3.191 | 3.258 | 4.143 | 3.991 |
| PDCD7 | 23.823 | 24.406 | 24.616 | 24.925 | 5.042 | 5.048 | 5.436 | 5.679 |
| PDGFRB | Undetermined | Undetermined | Undetermined | Undetermined | #VALUE! | #VALUE! | #VALUE! | #VALUE! |
| PDP1 | 25.799 | 25.387 | 26.940 | 25.667 | 7.018 | 6.029 | 7.760 | 6.421 |
| PER1 | 24.531 | 25.492 | 27.160 | 26.707 | 5.750 | 6.134 | 7.980 | 7.461 |
| PER2 | 24.162 | 24.378 | 24.811 | 24.547 | 5.381 | 5.020 | 5.631 | 5.301 |
| PIK3R1 | 22.958 | 23.908 | 24.331 | 24.602 | 4.177 | 4.550 | 5.151 | 5.356 |
| PLD1 | Undetermined | Undetermined | Undetermined | Undetermined | #VALUE! | #VALUE! | #VALUE! | #VALUE! |
| PLEKHF1 | 29.893 | 30.520 | 31.367 | 34.212 | 11.112 | 11.162 | 12.187 | 14.966 |
| POU2F1 | 23.693 | 24.243 | 25.222 | 25.607 | 4.912 | 4.885 | 6.042 | 6.361 |
| POU2F2 | 21.776 | 21.769 | 22.972 | 22.359 | 2.995 | 2.411 | 3.792 | 3.113 |
| RASA3 | 25.711 | 26.279 | 27.653 | 26.571 | 6.930 | 6.921 | 8.473 | 7.325 |
| RGS2 | 25.306 | 25.721 | 26.477 | 28.212 | 6.525 | 6.363 | 7.297 | 8.966 |
| RHOB | Undetermined | Undetermined | Undetermined | 38.682 | #VALUE! | #VALUE! | #VALUE! | 19.436 |
| RHOJ | Undetermined | Undetermined | Undetermined | Undetermined | #VALUE! | #VALUE! | #VALUE! | #VALUE! |
| SESN1 | 25.545 | 24.425 | 21.882 | 20.973 | 6.764 | 5.067 | 2.702 | 1.727 |
| SGK1 | 24.884 | 26.262 | 26.131 | 26.411 | 6.103 | 6.904 | 6.951 | 7.165 |
| SLC10A6 | 35.730 | Undetermined | 34.404 | 35.950 | 16.949 | #VALUE! | 15.224 | 16.704 |
| SLC19A2 | 25.756 | 25.536 | 26.202 | 25.342 | 6.975 | 6.178 | 7.022 | 6.096 |
| SLC22A5 | 32.280 | Undetermined | Undetermined | 38.888 | 13.499 | #VALUE! | #VALUE! | 19.642 |
| SNTA1 | 24.937 | 25.554 | 26.480 | 26.133 | 6.156 | 6.196 | 7.300 | 6.887 |
| SPHK1 | 31.323 | 31.119 | 34.340 | Undetermined | 12.542 | 11.761 | 15.160 | #VALUE! |
| SPSB1 | 26.573 | 26.285 | 28.977 | 28.200 | 7.792 | 6.927 | 9.797 | 8.954 |
| STAT5A | 22.191 | 22.769 | 23.379 | 22.666 | 3.410 | 3.411 | 4.199 | 3.420 |
| STAT5B | 22.200 | 22.683 | 23.111 | 23.737 | 3.419 | 3.325 | 3.931 | 4.491 |
| TBL1XR1 | 20.394 | 21.663 | 21.587 | 21.692 | 1.613 | 2.305 | 2.407 | 2.446 |
| TNF | 24.972 | 24.712 | 24.773 | 22.812 | 6.191 | 5.354 | 5.593 | 3.566 |
| TNFAIP3 | 25.433 | 26.896 | 27.393 | 28.474 | 6.652 | 7.538 | 8.213 | 9.228 |
| TSC22D3 | 22.534 | 23.300 | 21.502 | 21.179 | 3.753 | 3.942 | 2.322 | 1.933 |
| USP2 | 20.982 | 21.420 | 20.720 | 20.616 | 2.201 | 2.062 | 1.540 | 1.370 |
| USP54 | 26.748 | 26.364 | 27.638 | 26.992 | 7.967 | 7.006 | 8.458 | 7.746 |
| VDR | 29.817 | 27.736 | 31.463 | 29.508 | 11.036 | 8.378 | 12.283 | 10.262 |
| VLDLR | 35.442 | Undetermined | 33.979 | Undetermined | 16.661 | #VALUE! | 14.799 | #VALUE! |
| XDH | Undetermined | Undetermined | Undetermined | Undetermined | #VALUE! | #VALUE! | #VALUE! | #VALUE! |
| ZFP36 | 23.833 | 24.374 | 25.160 | 24.997 | 5.052 | 5.016 | 5.980 | 5.751 |
| ZHX3 | 24.547 | 29.785 | 25.114 | 24.601 | 5.766 | 10.427 | 5.934 | 5.355 |
| ZNF281 | 23.044 | 23.667 | 23.814 | 23.669 | 4.263 | 4.309 | 4.634 | 4.423 |
| ACTB | 14.794 | 15.664 | 15.466 | 15.976 | −3.987 | −3.694 | −3.714 | −3.270 |
| B2M | 18.781 | 19.358 | 19.180 | 19.246 | 0.000 | 0.000 | 0.000 | 0.000 |
| GAPDH | 15.388 | 15.720 | 16.234 | 17.444 | −3.393 | −3.638 | −2.946 | −1.802 |
| HPRT1 | 21.297 | 22.013 | 21.626 | 22.777 | 2.516 | 2.655 | 2.446 | 3.531 |
| RPLP0 | 15.092 | 14.837 | 15.994 | 15.962 | −3.689 | −4.521 | −3.186 | −3.284 |
| HGDC | Undetermined | Undetermined | Undetermined | Undetermined | #VALUE! | #VALUE! | #VALUE! | #VALUE! |
| RTC | 20.832 | 21.659 | 20.818 | 20.383 | 2.051 | 2.301 | 1.638 | 1.137 |
| RTC | 20.752 | 21.713 | 20.681 | 20.380 | 1.971 | 2.355 | 1.501 | 1.134 |
| RTC | 20.792 | 21.629 | 20.780 | 20.481 | 2.011 | 2.271 | 1.600 | 1.235 |
| PPC | 18.493 | 18.197 | 18.424 | 18.380 | −0.288 | −1.161 | −0.756 | −0.866 |
| PPC | 18.567 | 18.303 | 18.491 | 18.255 | −0.214 | −1.055 | −0.689 | −0.991 |
| PPC | 18.444 | 18.435 | 18.381 | 18.325 | −0.337 | −0.923 | −0.799 | −0.921 |

TABLE 4e-continued

Ct values and fold changes from the RT2 Glucocorticoid signaling PCR array analysis for RI cell line.

| Gene | Cpd44 | | Pred | | Combo | |
|---|---|---|---|---|---|---|
| | ΔΔCT | Fold Change | ΔΔCT | Fold Change | ΔΔCT | Fold Change |
| ADARB1 | −1.672 | 3.187 | 0.413 | 0.751 | 0.413 | 0.751 |
| AFF1 | −2.006 | 4.017 | −1.390 | 2.621 | −1.737 | 3.333 |
| AK2 | 0.268 | 0.830 | 0.686 | 0.622 | 1.576 | 0.335 |
| AMPD3 | −0.885 | 1.847 | −0.544 | 1.458 | −0.726 | 1.654 |
| ANGPTL4 | −0.935 | 1.912 | 1.668 | 0.315 | −1.047 | 2.066 |
| ANXA4 | −0.562 | 1.476 | 0.131 | 0.913 | −0.074 | 1.053 |
| AQP1 | #VALUE! | #VALUE! | #VALUE! | #VALUE! | #VALUE! | #VALUE! |
| ARID5B | −1.220 | 2.329 | 0.833 | 0.561 | 0.054 | 0.963 |
| ASPH | 0.476 | 0.719 | 0.771 | 0.586 | 1.532 | 0.346 |
| ATF4 | 0.003 | 0.998 | 1.364 | 0.389 | 2.386 | 0.191 |
| BCL6 | 0.263 | 0.833 | 0.937 | 0.522 | 0.858 | 0.552 |
| BMPER | #VALUE! | #VALUE! | #VALUE! | #VALUE! | #VALUE! | #VALUE! |
| CALCR | #VALUE! | #VALUE! | #VALUE! | #VALUE! | #VALUE! | #VALUE! |
| CEBPA | #VALUE! | #VALUE! | #VALUE! | #VALUE! | #VALUE! | #VALUE! |
| CEBPB | −0.004 | 1.003 | 2.638 | 0.161 | 3.554 | 0.085 |
| COL4A2 | −0.773 | 1.709 | #VALUE! | #VALUE! | 2.769 | 0.147 |
| CREB1 | 0.205 | 0.868 | 0.483 | 0.715 | 0.570 | 0.674 |
| CREB3 | −0.189 | 1.140 | 0.762 | 0.590 | 0.480 | 0.717 |
| CREB3L4 | −0.760 | 1.693 | 0.129 | 0.914 | −0.278 | 1.213 |
| CTGF | #VALUE! | #VALUE! | #VALUE! | #VALUE! | #VALUE! | #VALUE! |
| CYB561 | −1.477 | 2.784 | −1.663 | 3.167 | −2.199 | 4.592 |
| DDIT4 | 0.461 | 0.726 | 1.431 | 0.371 | 0.477 | 0.718 |
| DIRAS2 | #VALUE! | #VALUE! | #VALUE! | #VALUE! | #VALUE! | #VALUE! |
| DUSP1 | −0.321 | 1.249 | −0.153 | 1.112 | −0.650 | 1.569 |
| EDN1 | −1.208 | 2.310 | 6.595 | 0.010 | −2.211 | 4.630 |
| EHD3 | −0.962 | 1.948 | 0.055 | 0.963 | −1.447 | 2.726 |
| ERRFI1 | #VALUE! | #VALUE! | #VALUE! | #VALUE! | #VALUE! | #VALUE! |
| FKBP5 | 0.388 | 0.764 | −0.333 | 1.260 | −0.376 | 1.298 |
| FOSL2 | −1.274 | 2.418 | 2.300 | 0.203 | 4.536 | 0.043 |
| GDPD1 | −0.772 | 1.708 | 0.711 | 0.611 | 0.056 | 0.962 |
| GHRHR | #VALUE! | #VALUE! | #VALUE! | #VALUE! | #VALUE! | #VALUE! |
| GLUL | −2.614 | 6.122 | 1.007 | 0.498 | 1.721 | 0.303 |
| GOT1 | 0.518 | 0.698 | 1.467 | 0.362 | 2.597 | 0.165 |
| H6PD | −0.673 | 1.594 | 0.935 | 0.523 | −0.831 | 1.779 |
| HAS2 | #VALUE! | #VALUE! | #VALUE! | #VALUE! | #VALUE! | #VALUE! |
| HNRPLL | 0.309 | 0.807 | 0.789 | 0.579 | 1.866 | 0.274 |
| IL10 | −1.432 | 2.698 | −0.083 | 1.059 | #VALUE! | #VALUE! |
| IL1RN | −1.881 | 3.683 | −0.808 | 1.751 | −0.970 | 1.959 |
| IL6 | #VALUE! | #VALUE! | #VALUE! | #VALUE! | #VALUE! | #VALUE! |
| IL6R | −0.515 | 1.429 | 0.885 | 0.541 | 1.672 | 0.314 |
| KLF13 | −0.566 | 1.480 | 0.348 | 0.786 | 0.014 | 0.990 |
| KLF9 | #VALUE! | #VALUE! | #VALUE! | #VALUE! | #VALUE! | #VALUE! |
| LOX | −0.580 | 1.495 | −0.132 | 1.096 | −0.435 | 1.352 |
| MERTK | −4.419 | 21.392 | #VALUE! | #VALUE! | −3.726 | 13.232 |
| MT1E | #VALUE! | #VALUE! | #VALUE! | #VALUE! | #VALUE! | #VALUE! |
| MT2A | 0.577 | 0.670 | 1.656 | 0.317 | 1.980 | 0.253 |
| NFKBIA | 0.854 | 0.553 | 0.853 | 0.554 | 0.698 | 0.616 |
| NR3C1 | 0.067 | 0.955 | 0.952 | 0.517 | 0.800 | 0.574 |
| PDCD7 | 0.006 | 0.996 | 0.394 | 0.761 | 0.637 | 0.643 |
| PDGFRB | #VALUE! | #VALUE! | #VALUE! | #VALUE! | #VALUE! | #VALUE! |
| PDP1 | −0.989 | 1.985 | 0.742 | 0.598 | −0.597 | 1.513 |
| PER1 | 0.384 | 0.766 | 2.230 | 0.213 | 1.711 | 0.305 |
| PER2 | −0.361 | 1.284 | 0.250 | 0.841 | −0.080 | 1.057 |
| PIK3R1 | 0.373 | 0.772 | 0.974 | 0.509 | 1.179 | 0.442 |
| PLD1 | #VALUE! | #VALUE! | #VALUE! | #VALUE! | #VALUE! | #VALUE! |
| PLEKHF1 | 0.050 | 0.966 | 1.075 | 0.475 | 3.854 | 0.069 |
| POU2F1 | −0.027 | 1.019 | 1.130 | 0.457 | 1.449 | 0.366 |
| POU2F2 | −0.584 | 1.499 | 0.797 | 0.576 | 0.118 | 0.921 |
| RASA3 | −0.009 | 1.006 | 1.543 | 0.343 | 0.395 | 0.760 |
| RGS2 | −0.162 | 1.119 | 0.772 | 0.586 | 2.441 | 0.184 |
| RHOB | #VALUE! | #VALUE! | #VALUE! | #VALUE! | #VALUE! | #VALUE! |
| RHOJ | #VALUE! | #VALUE! | #VALUE! | #VALUE! | #VALUE! | #VALUE! |
| SESN1 | −1.697 | 3.242 | −4.062 | 16.703 | −5.037 | 32.831 |
| SGK1 | 0.801 | 0.574 | 0.848 | 0.556 | 1.062 | 0.479 |
| SLC10A6 | #VALUE! | #VALUE! | −1.725 | 3.306 | −0.245 | 1.185 |
| SLC19A2 | −0.797 | 1.737 | 0.047 | 0.968 | −0.879 | 1.839 |
| SLC22A5 | #VALUE! | #VALUE! | #VALUE! | #VALUE! | 6.143 | 0.014 |
| SNTA1 | 0.040 | 0.973 | 1.144 | 0.453 | 0.731 | 0.602 |
| SPHK1 | −0.781 | 1.718 | 2.618 | 0.163 | #VALUE! | #VALUE! |
| SPSB1 | −0.865 | 1.821 | 2.005 | 0.249 | 1.162 | 0.447 |
| STAT5A | 0.001 | 0.999 | 0.789 | 0.579 | 0.010 | 0.993 |
| STAT5B | −0.094 | 1.067 | 0.512 | 0.701 | 1.072 | 0.476 |
| TBL1XR1 | 0.692 | 0.619 | 0.794 | 0.577 | 0.833 | 0.561 |
| TNF | −0.837 | 1.786 | −0.598 | 1.514 | −2.625 | 6.169 |

TABLE 4e-continued

Ct values and fold changes from the RT2 Glucocorticoid signaling PCR array analysis for RI cell line.

| | | | | | | | |
|---|---|---|---|---|---|---|---|
| | TNFAIP3 | 0.886 | 0.541 | 1.561 | 0.339 | 2.576 | 0.168 |
| | TSC22D3 | 0.189 | 0.877 | −1.431 | 2.696 | −1.820 | 3.531 |
| | USP2 | −0.139 | 1.101 | −0.661 | 1.581 | −0.831 | 1.779 |
| | USP54 | −0.961 | 1.947 | 0.491 | 0.712 | −0.221 | 1.166 |
| | VDR | −2.658 | 6.312 | 1.247 | 0.421 | −0.774 | 1.710 |
| | VLDLR | #VALUE! | #VALUE! | −1.862 | 3.635 | #VALUE! | #VALUE! |
| | XDH | #VALUE! | #VALUE! | #VALUE! | #VALUE! | #VALUE! | #VALUE! |
| | ZFP36 | −0.036 | 1.025 | 0.928 | 0.526 | 0.699 | 0.616 |
| | ZHX3 | 4.661 | 0.040 | 0.168 | 0.890 | −0.411 | 1.330 |
| | ZNF281 | 0.046 | 0.969 | 0.371 | 0.773 | 0.160 | 0.895 |
| | ACTB | | | | | | |
| | B2M | | | | | | |
| | GAPDH | | | | | | |
| | HPRT1 | | | | | | |
| | RPLP0 | | | | | | |
| | HGDC | | | | | | |
| | RTC | | | | | | |
| | RTC | | | | | | |
| | RTC | | | | | | |
| | PPC | | | | | | |
| | PPC | | | | | | |
| | PPC | | | | | | |

TABLE 4f

Ct values and fold changes from the RT2 Glucocorticoid signaling PCR array analysis for SUDHL4 cell line.

| | Ct Values | | | | ΔCT (B2M) | | | |
|---|---|---|---|---|---|---|---|---|
| Gene | DMSO | Cpd44 | Pred | Combo | DMSO | Cpd44 | Pred | Combo |
| ADARB1 | 27.696 | 28.562 | 27.634 | 28.373 | 10.107 | 8.878 | 9.591 | 8.992 |
| AFF1 | 26.492 | 25.936 | 25.874 | 25.660 | 7.394 | 7.118 | 6.965 | 7.788 |
| AK2 | 19.861 | 20.311 | 20.602 | 20.682 | 2.416 | 1.846 | 1.340 | 1.157 |
| AMPD3 | 25.234 | 25.553 | 24.780 | 25.739 | 7.473 | 6.024 | 6.582 | 6.530 |
| ANGPTL4 | 29.764 | 29.825 | 29.326 | 30.167 | 11.901 | 10.570 | 10.854 | 11.060 |
| ANXA4 | 26.847 | 28.717 | 26.973 | 28.902 | 10.636 | 8.217 | 9.746 | 8.143 |
| AQP1 | Undetermined | Undetermined | 32.982 | 32.161 | 13.895 | 14.226 | #VALUE! | #VALUE! |
| ARID5B | 25.120 | 25.129 | 24.504 | 24.555 | 6.289 | 5.748 | 6.158 | 6.416 |
| ASPH | 22.618 | 23.348 | 22.741 | 23.094 | 4.828 | 3.985 | 4.377 | 3.914 |
| ATF4 | 19.323 | 18.778 | 18.988 | 18.352 | 0.086 | 0.232 | −0.193 | 0.619 |
| BCL6 | 20.521 | 21.075 | 20.634 | 21.163 | 2.897 | 1.878 | 2.104 | 1.817 |
| BMPER | Undetermined | Undetermined | Undetermined | Undetermined | #VALUE! | #VALUE! | #VALUE! | #VALUE! |
| CALCR | Undetermined | Undetermined | Undetermined | Undetermined | #VALUE! | #VALUE! | #VALUE! | #VALUE! |
| CEBPA | 28.837 | 31.206 | 28.782 | 30.802 | 12.536 | 10.026 | 12.235 | 10.133 |
| CEBPB | 24.507 | 23.911 | 23.944 | 22.678 | 4.412 | 5.188 | 4.940 | 5.803 |
| COL4A2 | Undetermined | Undetermined | Undetermined | 33.904 | 15.638 | #VALUE! | #VALUE! | #VALUE! |
| CREB1 | 22.906 | 22.973 | 22.993 | 22.816 | 4.550 | 4.237 | 4.002 | 4.202 |
| CREB3 | 24.330 | 24.566 | 24.421 | 24.421 | 6.155 | 5.665 | 5.595 | 5.626 |
| CREB3L4 | 24.709 | 25.089 | 24.418 | 24.583 | 6.317 | 5.662 | 6.118 | 6.005 |
| CTGF | Undetermined | Undetermined | Undetermined | Undetermined | #VALUE! | #VALUE! | #VALUE! | #VALUE! |
| CYB561 | 33.993 | 36.737 | 33.006 | 36.752 | 18.486 | 14.250 | 17.766 | 15.289 |
| DDIT4 | 21.247 | 21.455 | 21.854 | 22.681 | 4.415 | 3.098 | 2.484 | 2.543 |
| DIRAS2 | Undetermined | Undetermined | 33.382 | Undetermined | #VALUE! | 14.626 | #VALUE! | #VALUE! |
| DUSP1 | 26.436 | 26.325 | 26.754 | 26.713 | 8.447 | 7.998 | 7.354 | 7.732 |
| EDN1 | 32.440 | 33.297 | 32.372 | Undetermined | #VALUE! | 13.616 | 14.326 | 13.736 |
| EHD3 | 24.298 | 25.766 | 24.878 | 26.386 | 8.120 | 6.122 | 6.795 | 5.594 |
| ERRFI1 | Undetermined | Undetermined | Undetermined | Undetermined | #VALUE! | #VALUE! | #VALUE! | #VALUE! |
| FKBP5 | 20.533 | 20.494 | 21.869 | 21.371 | 3.105 | 3.113 | 1.523 | 1.829 |
| FOSL2 | 35.083 | 31.757 | 33.362 | Undetermined | #VALUE! | 14.606 | 12.786 | 16.379 |
| GDPD1 | 27.358 | 28.134 | 26.972 | 27.838 | 9.572 | 8.216 | 9.163 | 8.654 |
| GHRHR | 36.313 | 37.623 | Undetermined | 36.734 | 18.468 | #VALUE! | 18.652 | 17.609 |
| GLUL | 35.436 | 35.795 | 34.414 | Undetermined | #VALUE! | 15.658 | 16.824 | 16.732 |
| GOT1 | 22.400 | 22.607 | 22.859 | 22.304 | 4.038 | 4.103 | 3.636 | 3.696 |
| H6PD | 25.209 | 25.743 | 24.819 | 24.878 | 6.612 | 6.063 | 6.772 | 6.505 |
| HAS2 | Undetermined | 35.628 | 31.961 | Undetermined | #VALUE! | 13.205 | 16.657 | #VALUE! |
| HNRPLL | 22.667 | 22.977 | 22.577 | 22.558 | 4.292 | 3.821 | 4.006 | 3.963 |
| IL10 | 32.210 | 33.099 | 31.119 | 32.524 | 14.258 | 12.363 | 14.128 | 13.506 |
| IL1RN | Undetermined | Undetermined | 36.259 | Undetermined | #VALUE! | 17.503 | #VALUE! | #VALUE! |
| IL6 | Undetermined | Undetermined | Undetermined | Undetermined | #VALUE! | #VALUE! | #VALUE! | #VALUE! |
| IL6R | 32.607 | 33.589 | 31.995 | 33.408 | 15.142 | 13.239 | 14.618 | 13.903 |
| KLF13 | 22.256 | 22.649 | 22.834 | 22.878 | 4.612 | 4.078 | 3.678 | 3.552 |
| KLF9 | 26.816 | 27.456 | 26.769 | 27.572 | 9.306 | 8.013 | 8.485 | 8.112 |
| LOX | 33.947 | Undetermined | Undetermined | Undetermined | #VALUE! | #VALUE! | #VALUE! | 15.243 |
| MERTK | 33.257 | Undetermined | 33.859 | 31.392 | 13.126 | 15.103 | #VALUE! | 14.553 |

TABLE 4f-continued

Ct values and fold changes from the RT2 Glucocorticoid signaling PCR array analysis for SUDHL4 cell line.

| | | | | | | | | |
|---|---|---|---|---|---|---|---|---|
| MT1E | Undetermined | Undetermined | Undetermined | Undetermined | #VALUE! | #VALUE! | #VALUE! | #VALUE! |
| MT2A | 23.416 | 24.175 | 23.522 | 23.341 | 5.075 | 4.766 | 5.204 | 4.712 |
| NFKBIA | 22.744 | 22.909 | 23.016 | 22.914 | 4.648 | 4.260 | 3.938 | 4.040 |
| NR3C1 | 22.602 | 22.803 | 22.781 | 22.525 | 4.259 | 4.025 | 3.832 | 3.898 |
| PDCD7 | 23.859 | 24.858 | 24.113 | 23.750 | 5.484 | 5.357 | 5.887 | 5.155 |
| PDGFRB | Undetermined | Undetermined | 35.205 | Undetermined | #VALUE! | 16.449 | #VALUE! | #VALUE! |
| PDP1 | 25.255 | 26.112 | 25.507 | 25.928 | 7.662 | 6.751 | 7.141 | 6.551 |
| PER1 | 24.612 | 24.926 | 24.973 | 25.007 | 6.741 | 6.217 | 5.955 | 5.908 |
| PER2 | 23.794 | 24.371 | 24.403 | 24.767 | 6.501 | 5.647 | 5.400 | 5.090 |
| PIK3R1 | 23.210 | 23.440 | 23.615 | 23.627 | 5.361 | 4.859 | 4.469 | 4.506 |
| PLD1 | Undetermined | Undetermined | Undetermined | Undetermined | #VALUE! | #VALUE! | #VALUE! | #VALUE! |
| PLEKHF1 | 27.292 | 27.868 | 27.684 | 28.448 | 10.182 | 8.928 | 8.897 | 8.588 |
| POU2F1 | 23.799 | 24.224 | 23.866 | 23.951 | 5.685 | 5.110 | 5.253 | 5.095 |
| POU2F2 | 21.502 | 21.920 | 21.841 | 21.890 | 3.624 | 3.085 | 2.949 | 2.798 |
| RASA3 | 22.754 | 23.207 | 22.984 | 23.225 | 4.959 | 4.228 | 4.236 | 4.050 |
| RGS2 | 24.883 | 25.145 | 24.670 | 24.812 | 6.546 | 5.914 | 6.174 | 6.179 |
| RHOB | 30.760 | 32.584 | 30.084 | 31.155 | 12.889 | 11.328 | 13.613 | 12.056 |
| RHOJ | Undetermined | Undetermined | 38.493 | Undetermined | #VALUE! | 19.737 | #VALUE! | #VALUE! |
| SESN1 | 22.189 | Undetermined | 25.195 | 26.963 | 8.697 | 6.439 | #VALUE! | 3.485 |
| SGK1 | 25.886 | 25.808 | 26.513 | 25.449 | 7.183 | 7.757 | 6.837 | 7.182 |
| SLC10A6 | 37.655 | 34.857 | 34.336 | 38.026 | 19.760 | 15.580 | 15.886 | 18.951 |
| SLC19A2 | 26.295 | 27.465 | 26.633 | 27.755 | 9.489 | 7.877 | 8.494 | 7.591 |
| SLC22A5 | 27.847 | 28.544 | 27.725 | 28.010 | 9.744 | 8.969 | 9.573 | 9.143 |
| SNTA1 | 24.008 | 24.797 | 24.422 | 24.779 | 6.513 | 5.666 | 5.826 | 5.304 |
| SPHK1 | 29.372 | 30.619 | 29.007 | 29.583 | 11.317 | 10.251 | 11.648 | 10.668 |
| SPSB1 | 25.736 | 26.495 | 25.588 | 25.722 | 7.456 | 6.832 | 7.524 | 7.032 |
| STAT5A | 24.652 | 25.174 | 24.761 | 24.858 | 6.592 | 6.005 | 6.203 | 5.948 |
| STAT5B | 21.986 | 22.153 | 21.908 | 21.716 | 3.450 | 3.152 | 3.182 | 3.282 |
| TBL1XR1 | 20.756 | 20.805 | 20.855 | 20.821 | 2.555 | 2.099 | 1.834 | 2.052 |
| TNF | 27.723 | 29.337 | 29.509 | 31.477 | 13.211 | 10.753 | 10.366 | 9.019 |
| TNFAIP3 | 28.965 | 28.521 | 27.807 | 26.978 | 8.712 | 9.051 | 9.550 | 10.261 |
| TSC22D3 | 21.819 | 21.432 | 23.384 | 22.896 | 4.630 | 4.628 | 2.461 | 3.115 |
| USP2 | 20.842 | 21.342 | 22.120 | 22.318 | 4.052 | 3.364 | 2.371 | 2.138 |
| USP54 | 26.333 | 26.952 | 33.990 | 27.307 | 9.041 | 15.234 | 7.981 | 7.629 |
| VDR | 27.497 | 28.330 | 26.956 | 28.621 | 10.355 | 8.200 | 9.359 | 8.793 |
| VLDLR | 30.410 | 28.792 | 27.824 | 26.896 | 8.630 | 9.068 | 9.821 | 11.706 |
| XDH | Undetermined | Undetermined | Undetermined | Undetermined | #VALUE! | #VALUE! | #VALUE! | #VALUE! |
| ZFP36 | 24.716 | 24.706 | 24.770 | 24.542 | 6.276 | 6.014 | 5.735 | 6.012 |
| ZHX3 | 24.009 | 24.719 | 24.325 | 24.882 | 6.616 | 5.569 | 5.748 | 5.305 |
| ZNF281 | 23.423 | 23.881 | 23.813 | 23.935 | 5.669 | 5.057 | 4.910 | 4.719 |
| ACTB | 13.717 | 14.247 | 14.284 | 14.272 | -3.994 | -4.472 | -4.724 | -4.987 |
| B2M | 18.704 | 18.971 | 18.756 | 18.266 | 0.000 | 0.000 | 0.000 | 0.000 |
| GAPDH | 15.435 | 15.835 | 15.790 | 15.782 | -2.484 | -2.966 | -3.136 | -3.269 |
| HPRT1 | 21.349 | 21.358 | 21.582 | 21.214 | 2.948 | 2.826 | 2.387 | 2.645 |
| RPLP0 | 15.192 | 15.469 | 15.266 | 15.194 | -3.072 | -3.490 | -3.502 | -3.512 |
| HGDC | Undetermined | Undetermined | Undetermined | Undetermined | #VALUE! | #VALUE! | #VALUE! | #VALUE! |
| RTC | 21.372 | 21.163 | 21.388 | 21.673 | 3.407 | 2.632 | 2.192 | 2.668 |
| RTC | 21.441 | 21.008 | 21.369 | 21.554 | 3.288 | 2.613 | 2.037 | 2.737 |
| RTC | 21.504 | 21.137 | 21.357 | 21.500 | 3.234 | 2.601 | 2.166 | 2.800 |
| PPC | 18.529 | 18.295 | 18.338 | 18.368 | 0.102 | -0.418 | -0.676 | -0.175 |
| PPC | 18.544 | 18.326 | 19.432 | 18.405 | 0.139 | 0.676 | -0.645 | -0.160 |
| PPC | 18.784 | 18.935 | 18.081 | 18.679 | 0.413 | -0.675 | -0.036 | 0.080 |

| | Cpd44 | | Pred | | Combo | |
|---|---|---|---|---|---|---|
| Gene | ΔΔCT | Fold Change | ΔΔCT | Fold Change | ΔΔCT | Fold Change |
| ADARB1 | -1.229 | 2.344 | -0.516 | 1.430 | -1.115 | 2.166 |
| AFF1 | -0.276 | 1.211 | -0.429 | 1.346 | 0.394 | 0.761 |
| AK2 | -0.570 | 1.485 | -1.076 | 2.108 | -1.259 | 2.393 |
| AMPD3 | -1.449 | 2.730 | -0.891 | 1.854 | -0.943 | 1.923 |
| ANGPTL4 | -1.331 | 2.516 | -1.047 | 2.066 | -0.841 | 1.791 |
| ANXA4 | -2.419 | 5.348 | -0.890 | 1.853 | -2.493 | 5.629 |
| AQP1 | 0.331 | 0.795 | #VALUE! | #VALUE! | #VALUE! | #VALUE! |
| ARID5B | -0.541 | 1.455 | -0.131 | 1.095 | 0.127 | 0.916 |
| ASPH | -0.843 | 1.794 | -0.451 | 1.367 | -0.914 | 1.884 |
| ATF4 | 0.146 | 0.904 | -0.279 | 1.213 | 0.533 | 0.691 |
| BCL6 | -1.019 | 2.027 | -0.793 | 1.733 | -1.080 | 2.114 |
| BMPER | #VALUE! | #VALUE! | #VALUE! | #VALUE! | #VALUE! | #VALUE! |
| CALCR | #VALUE! | #VALUE! | #VALUE! | #VALUE! | #VALUE! | #VALUE! |
| CEBPA | -2.510 | 5.696 | -0.301 | 1.232 | -2.403 | 5.289 |
| CEBPB | 0.776 | 0.584 | 0.528 | 0.694 | 1.391 | 0.381 |
| COL4A2 | #VALUE! | #VALUE! | #VALUE! | #VALUE! | #VALUE! | #VALUE! |
| CREB1 | -0.313 | 1.242 | -0.548 | 1.462 | -0.348 | 1.273 |
| CREB3 | -0.490 | 1.404 | -0.560 | 1.474 | -0.529 | 1.443 |
| CREB3L4 | -0.655 | 1.575 | -0.199 | 1.148 | -0.312 | 1.241 |
| CTGF | #VALUE! | #VALUE! | #VALUE! | #VALUE! | #VALUE! | #VALUE! |
| CYB561 | -4.236 | 18.844 | -0.720 | 1.647 | -3.197 | 9.170 |

TABLE 4f-continued

Ct values and fold changes from the RT2 Glucocorticoid signaling PCR array analysis for SUDHL4 cell line.

| | | | | | | |
|---|---|---|---|---|---|---|
| DDIT4 | −1.317 | 2.491 | −1.931 | 3.813 | −1.872 | 3.660 |
| DIRAS2 | #VALUE! | #VALUE! | #VALUE! | #VALUE! | #VALUE! | #VALUE! |
| DUSP1 | −0.449 | 1.365 | −1.093 | 2.133 | −0.715 | 1.641 |
| EDN1 | #VALUE! | #VALUE! | #VALUE! | #VALUE! | #VALUE! | #VALUE! |
| EHD3 | −1.998 | 3.994 | −1.325 | 2.505 | −2.526 | 5.760 |
| ERRFI1 | #VALUE! | #VALUE! | #VALUE! | #VALUE! | #VALUE! | #VALUE! |
| FKBP5 | 0.008 | 0.994 | −1.582 | 2.994 | −1.276 | 2.422 |
| FOSL2 | #VALUE! | #VALUE! | #VALUE! | #VALUE! | #VALUE! | #VALUE! |
| GDPD1 | −1.356 | 2.560 | −0.409 | 1.328 | −0.918 | 1.889 |
| GHRHR | #VALUE! | #VALUE! | 0.184 | 0.880 | −0.859 | 1.814 |
| GLUL | #VALUE! | #VALUE! | #VALUE! | #VALUE! | #VALUE! | #VALUE! |
| GOT1 | 0.065 | 0.956 | −0.402 | 1.321 | −0.342 | 1.268 |
| H6PD | −0.549 | 1.463 | 0.160 | 0.895 | −0.107 | 1.077 |
| HAS2 | #VALUE! | #VALUE! | #VALUE! | #VALUE! | #VALUE! | #VALUE! |
| HNRPLL | −0.471 | 1.386 | −0.286 | 1.219 | −0.329 | 1.256 |
| IL10 | −1.895 | 3.719 | −0.130 | 1.094 | −0.752 | 1.684 |
| IL1RN | #VALUE! | #VALUE! | #VALUE! | #VALUE! | #VALUE! | #VALUE! |
| IL6 | #VALUE! | #VALUE! | #VALUE! | #VALUE! | #VALUE! | #VALUE! |
| IL6R | −1.903 | 3.740 | −0.524 | 1.438 | −1.239 | 2.360 |
| KLF13 | −0.534 | 1.448 | −0.934 | 1.911 | −1.060 | 2.085 |
| KLF9 | −1.293 | 2.450 | −0.821 | 1.767 | −1.194 | 2.288 |
| LOX | #VALUE! | #VALUE! | #VALUE! | #VALUE! | #VALUE! | #VALUE! |
| MERTK | 1.977 | 0.254 | #VALUE! | #VALUE! | 1.427 | 0.372 |
| MT1E | #VALUE! | #VALUE! | #VALUE! | #VALUE! | #VALUE! | #VALUE! |
| MT2A | −0.309 | 1.239 | 0.129 | 0.914 | −0.363 | 1.286 |
| NFKBIA | −0.388 | 1.309 | −0.710 | 1.636 | −0.608 | 1.524 |
| NR3C1 | −0.234 | 1.176 | −0.427 | 1.344 | −0.361 | 1.284 |
| PDCD7 | −0.127 | 1.092 | 0.403 | 0.756 | −0.329 | 1.256 |
| PDGFRB | #VALUE! | #VALUE! | #VALUE! | #VALUE! | #VALUE! | #VALUE! |
| PDP1 | −0.911 | 1.880 | −0.521 | 1.435 | −1.111 | 2.160 |
| PER1 | −0.524 | 1.438 | −0.786 | 1.724 | −0.833 | 1.781 |
| PER2 | −0.854 | 1.808 | −1.101 | 2.145 | −1.411 | 2.659 |
| PIK3R1 | −0.502 | 1.416 | −0.892 | 1.856 | −0.855 | 1.809 |
| PLD1 | #VALUE! | #VALUE! | #VALUE! | #VALUE! | #VALUE! | #VALUE! |
| PLEKHF1 | −1.254 | 2.385 | −1.285 | 2.437 | −1.594 | 3.019 |
| POU2F1 | −0.575 | 1.490 | −0.432 | 1.349 | −0.590 | 1.505 |
| POU2F2 | −0.539 | 1.453 | −0.675 | 1.597 | −0.826 | 1.773 |
| RASA3 | −0.731 | 1.660 | −0.723 | 1.651 | −0.909 | 1.878 |
| RGS2 | −0.632 | 1.550 | −0.372 | 1.294 | −0.367 | 1.290 |
| RHOB | −1.561 | 2.951 | 0.724 | 0.605 | −0.833 | 1.781 |
| RHOJ | #VALUE! | #VALUE! | #VALUE! | #VALUE! | #VALUE! | #VALUE! |
| SESN1 | −2.258 | 4.783 | #VALUE! | #VALUE! | −5.212 | 37.065 |
| SGK1 | 0.574 | 0.672 | −0.346 | 1.271 | −0.001 | 1.001 |
| SLC10A6 | −4.180 | 18.126 | −3.874 | 14.662 | −0.809 | 1.752 |
| SLC19A2 | −1.612 | 3.057 | −0.995 | 1.993 | −1.898 | 3.727 |
| SLC22A5 | −0.775 | 1.711 | −0.171 | 1.126 | −0.601 | 1.517 |
| SNTA1 | −0.847 | 1.799 | −0.687 | 1.610 | −1.209 | 2.312 |
| SPHK1 | −1.066 | 2.094 | 0.331 | 0.795 | −0.649 | 1.568 |
| SPSB1 | −0.624 | 1.541 | 0.068 | 0.954 | −0.424 | 1.342 |
| STAT5A | −0.587 | 1.502 | −0.389 | 1.309 | −0.644 | 1.563 |
| STAT5B | −0.298 | 1.229 | −0.268 | 1.204 | −0.168 | 1.123 |
| TBL1XR1 | −0.456 | 1.372 | −0.721 | 1.648 | −0.503 | 1.417 |
| TNF | −2.458 | 5.495 | −2.845 | 7.185 | −4.192 | 18.278 |
| TNFAIP3 | 0.339 | 0.791 | 0.838 | 0.559 | 1.549 | 0.342 |
| TSC22D3 | −0.002 | 1.001 | −2.169 | 4.497 | −1.515 | 2.858 |
| USP2 | −0.688 | 1.611 | −1.681 | 3.207 | −1.914 | 3.769 |
| USP54 | 6.193 | 0.014 | −1.060 | 2.085 | −1.412 | 2.661 |
| VDR | −2.155 | 4.454 | −0.996 | 1.994 | −1.562 | 2.953 |
| VLDLR | 0.438 | 0.738 | 1.191 | 0.438 | 3.076 | 0.119 |
| XDH | #VALUE! | #VALUE! | #VALUE! | #VALUE! | #VALUE! | #VALUE! |
| ZFP36 | −0.262 | 1.199 | −0.541 | 1.455 | −0.264 | 1.201 |
| ZHX3 | −1.047 | 2.066 | −0.868 | 1.825 | −1.311 | 2.481 |
| ZNF281 | −0.612 | 1.528 | −0.759 | 1.692 | −0.950 | 1.932 |
| ACTB | | | | | | |
| B2M | | | | | | |
| GAPDH | | | | | | |
| HPRT1 | | | | | | |
| RPLP0 | | | | | | |
| HGDC | | | | | | |
| RTC | | | | | | |
| RTC | | | | | | |
| RTC | | | | | | |
| PPC | | | | | | |
| PPC | | | | | | |
| PPC | | | | | | |

EXAMPLE 2

Compound 44 and Everolimus Act Synergistically to Enhance Cell Cycle Arrest in G1 Phase in EZH2 Mutant WSU-DLCL2 Cells, Apoptosis in Wild Type EZH2 SU-DH-L5 Cells In FIG. 11B-11E, each point represents the mean of percentage of gated cells in early and late apoptosis (Annexin-V positive, mean +/−S.D., n=3). In FIGS. 11C and 11F, points on the progress curve represent the mean percentage of gated cells by DNA content (PI positive, mean +/−S.D., n=2). In FIG. 11A, WSU-DLCL2 cells were treated at a 400:1 constant ratio with a combination of Compound 44 and Everolimus. The combination was shown to induce very strong synergy with CI values of 0.34-0.003. In FIG. 11B) Apoptosis levels assessed in WSU-DLCL2 cells treated with Compound 44 (500 nM), Everolimus (5 nM) or in combination at the same concentrations. No increase in apoptosis on WSU-DLCL2 cells was seen. In FIG. 11C, A significant increase in G1 phase of cell cycle was observed after co-treatment compared to Compound 44 alone. In FIG. 11D, SU-DHL-5 cells were treated at a 4000:3 constant ratio in combination. The combination was shown to induce very strong synergy with CI values of 0.135-0.008. In FIG. 11E, A significant increase in Annexin positive cells was measured after co-treatment (500 nM Compound 44, 0.75 nM Everolimus), compared with Compound 44 alone (p<0.0001). In FIG. 11F, A significant increase in sub-G1 phase of cell cycle was observed after co-treatment.

EXAMPLE 3

Compound 44 and Ibrutinib Act Synergistically to Enhance Apoptosis in EZH2 Mutant WSU-DLCL2 Cells and Wild Type EZH2 SU-DH-L5 Cells In FIG. 12B-12E, each point represents the mean of percentage of gated cells in early and late apoptosis (Annexin-V positive, mean +/−S.D., n=3). In FIG. 12C and FIG. 12F, points on the progress curve represent the mean percentage of gated cells by DNA content (PI positive, mean +/−S.D., n=2). In FIG. 12A, WSU-DLCL2 cells were treated at a 4:5 constant ratio with a combination of Compound 44 and Ibrutinib. The combination of these agents demonstrates strong synergy with CI values between 0.39 and 0.14. In FIG. 12B, apoptosis levels assessed in WSU-DLCL2 cells treated with Compound 44 (500 nM), Ibrutinib (625 nM) or in combination. This combination revealed a synergistic time-dependent increase in apoptosis on WSU-DLCL2 cells. In FIG. 12C, cell cycle analysis revealed a time-dependent increase in the percentage of WSU-DLCL2 cells in G1-phase with a steep increase after combination treatment. In FIG. 12D, SU-DHL-5 cells were treated at a 1:5 constant ratio of Compound 44: Ibrutinib. The combination induced very strong synergy with CI values of 0.222-0.002. In FIG. 12E, synergistic and time-dependent increase of Annexin positive staining of SU-DHL-5 cells after cotreatment with Compound 44 (1000 nM) and ibrutinib (2500 nM) compared with Compound 44 alone (p<0.0001). In FIG. 12F, cell cycle analysis of SU-DHL-5 cells treated in combination revealed an increase in the cells in the sub-G1 population after co-treatment compared with each agent alone.

EXAMPLE 4

Compound 44 and MK-2206 Act Synergistically to Enhance Apoptosis in EZH2 Mutant WSU-DLCL2 Cells and Wild Type EZH2 (SU-DH-L5 and OCI-LY-19) Cells.

Figure 13G:
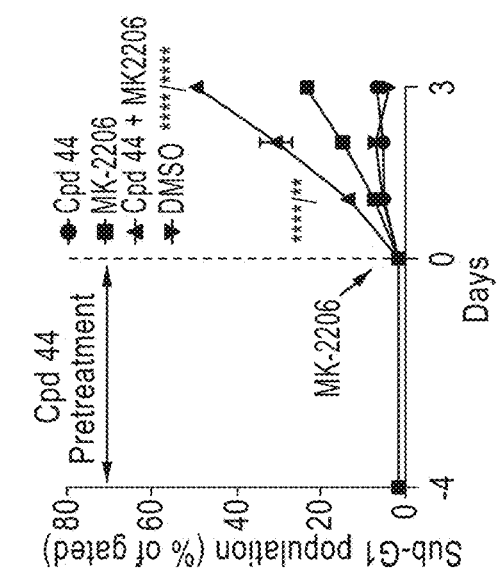
Figure 13H:
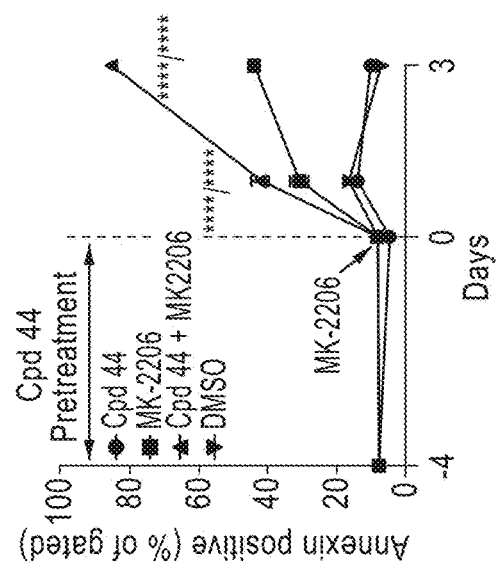
Figure 13I:
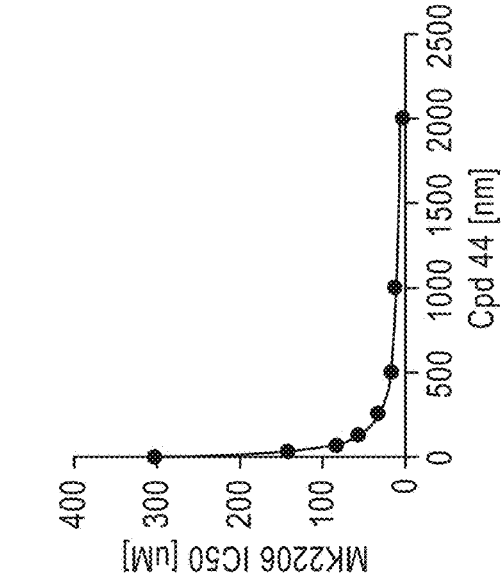

In FIG. 13A, WSU-DLCL2 cells were treated at a 4:1 constant ratio with a combination of Compound 44 and MK-2206. Fa-CI plot demonstrates very strong synergy with CI values between 0.77-0.005. In FIG. 13B, Time dependent increase in the percentage of Annexin positive WSU-DLCL2 cells when co-treated with Compound 44 (2000 nM) and MK-2206 (400 nM). In FIG. 13C, cell cycle analysis revealed an increase in the percentage of WSU-DLCL2 cells in G1-phase with a steep increase after one day of co-treatment compared with Compound 44 alone (p<0.0001). In FIG. 13D, SU-DHL-5 cells were treated at a 2:1 constant ratio for Compound 44 and MK-2206. The combination induced very strong synergy with CI values of 0.276-0.001. In FIG. 13E, apoptosis level assessment in SU-DHL-5 revealed an increase in Annexin positive cells after 24 hours of co-treatment (500 nM Compound 44, 250 nM MK-2206) compared with Compound 44 alone (p<0.0001). In FIG. 13F, cell cycle analysis of SU-DHL-5 cells treated in combination showed an increase in the percentage of cells in sub-G1 population compared with treatment of the agents individually. In FIG. 13G, strong synergy in OCI-LY19 cells was observed by treatment with a combination of Compound 44 and MK-2206 with a $1/\alpha$ value of 71.4. In FIG. 13H, Time-dependent increase in apoptosis was shown when OCI-LY19 cells were treated with the combination (1000 nM Compound 44, 2500 nM MK-2206) compared with Compound 44 alone (p<0.0001). In FIG. 13I, cell cycle analysis of OCI-LY19 cells treated with the combination revealed a time-dependent increase of cells in sub-G1 phase of the cell cycle (p<0.0001).

EXAMPLE 5

Figure 14A:
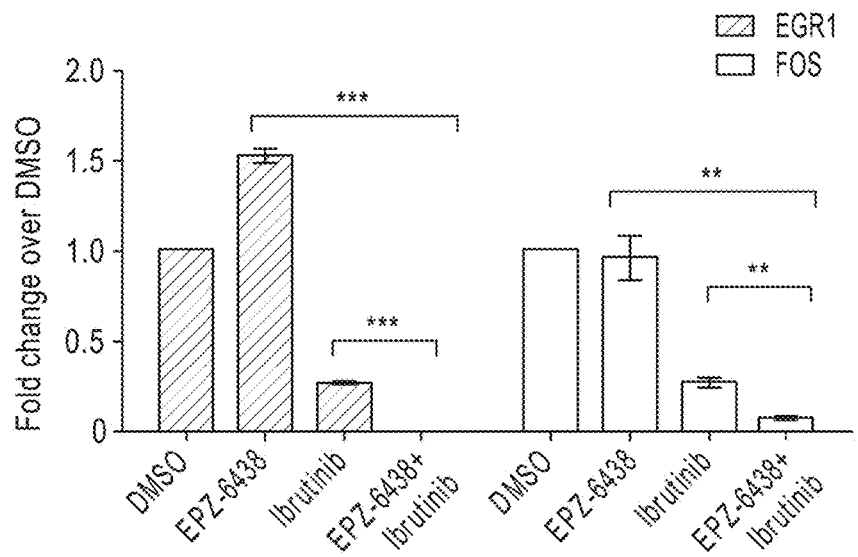
FIGS. 14A-14C are bar graphs showing change in gene expression of EGR1, FOS, TCL1, AICDA, and GJA1 when WSU-DLCL2 and SU-DHL-5 cells were treated with Compound 44, ibrutinib, MK-2206, a combination of Compound 44 and ibrutinib, or a combination of Compound 44 and MK-2206. Downregulation of EGR1 (40 fold) and FOS (4 fold) and upregulation of AICDA (3 fold), TCL1A (5 fold), and GJA1 (3 fold) was observed with a combination of Compound 44 and a second agent than was observed with treatment of single agents alone (FIGS. 14A-14C).
Figure 14B:
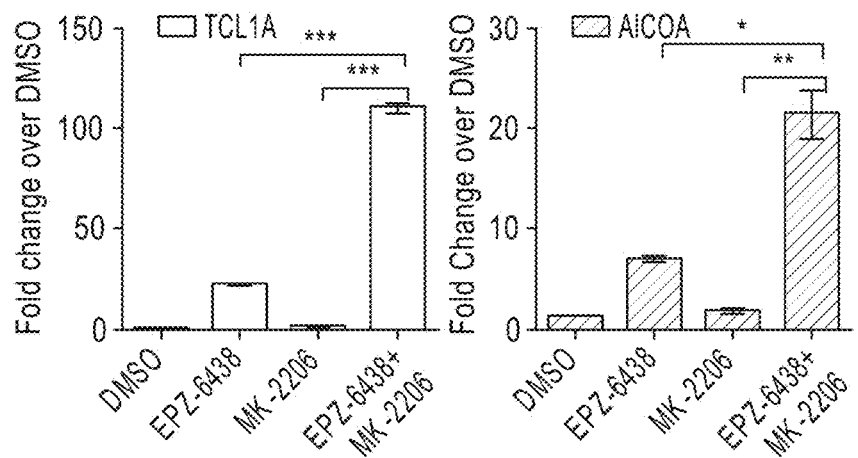
Figure 14C:
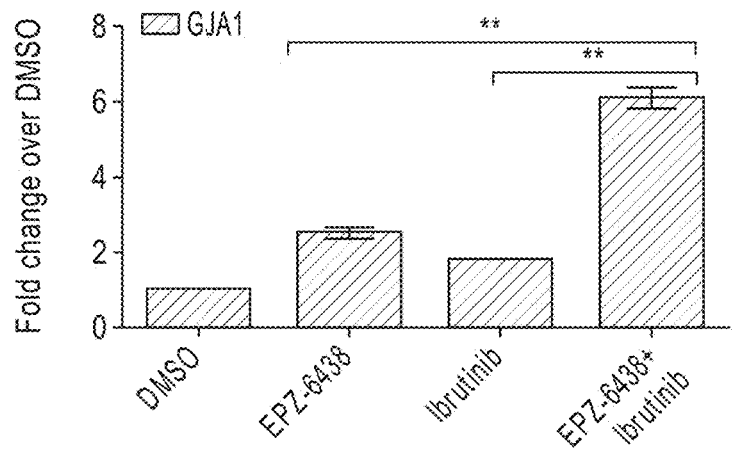

Regulation of Target Genes with Combinations of Compound 44 and BCR Pathway Inhibitors In FIG. 14A, downregulation of EGR1 (40 fold) and FOS (4 fold) with a combination of Compound 44 and Ibrutinib compared to single agents in WSU-DLCL2 cells. In FIG. 14B, upregulation of AICDA (3 fold) and TCL1A (5 fold) with a combination of Compound 44 and MK-2206 is compared to single agents in WSU-DLCL2 cells. In FIG. 14C, upregulation of GJA1 (3 fold) with a combination of Compound 44 and Ibrutinib is compared to single agents in SU-DHL-5 cells. Value for statistical analysis are a mean of duplicate or triplicate +/−SD. t test, *P<0.05, P<0.01, *P<0.001, ****P<0.0001

EXAMPLE 6

Synergistic Interactions Between EZH2 Inhibition and Modulation of the BCR Signaling Pathway, BCL2 Inhibition and GR Agonism in Germinal Center B Cell Lines.

Figure 15:
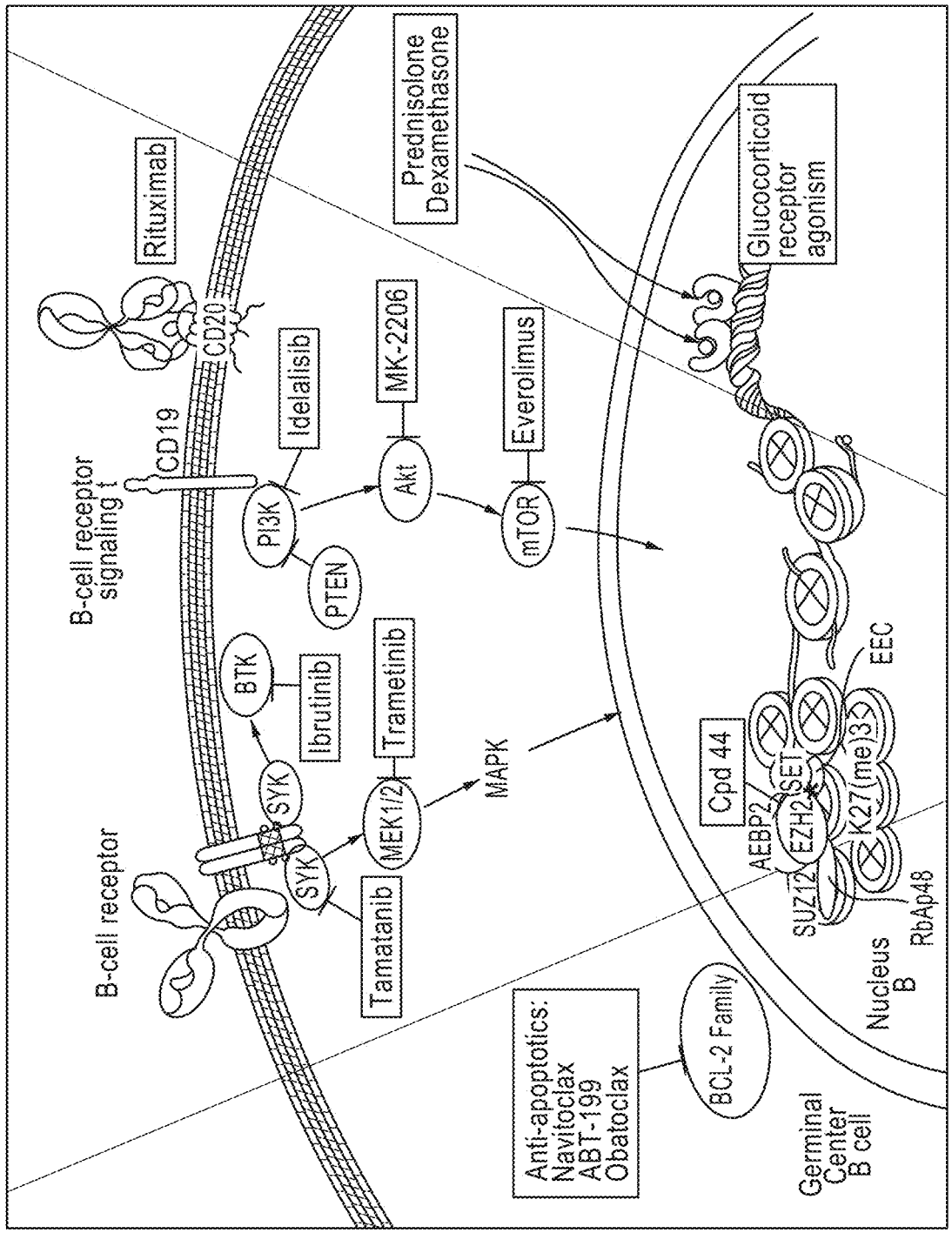
FIG. 15 is a diagram of the signaling pathways implicated in Diffuse Large B-cell Lymphoma (DLBCL) biology and the targets of various chemotherapeutic agents within the signaling pathway.

Several synergistic combinations were uncovered in this study with key players in the signaling pathways implicated in DLBCL biology (see FIG. 15). Inhibitors targeting nodes of the B-cell receptor pathway such as those of the PI3K/Akt/mTOR signaling cascade, MEK1/2 in the MAPK cascade, SYK and BTK showed very strong synergy when combined with EZP-6438 extending the impact of EZH2 inhibition from mutant EZH2 bearing GCB cell lines to those of the wild type subtype. Inhibitors of BCL-2 family of proteins, obatoclax, navitoclax and ABT-199 showed synergistic antiproliferative activity in combination with Compound 44. Glucorticoid receptor agonists, prednisolone and dexamethasone display a dramatic enhancement of EZH2 inhibition in mutant cell lines and sensitize wild type to EZH2i. Rituximab, the antibody combined with chemotherapeutics in R-CHOP targets cd-20 to elicit enhanced antiproliferative effects in vitro in mutant cell lines.

EXAMPLE 7

Compound 44 and Everolimus Act Synergistically to Decrease Populations of Cells in S and G2/M Phases of Mutant WSU-DLCL2 Cells and G1, S, and G2/M Phases in Wild Type SU-DHL-5 Cells.

WSU-DLCL2, SU-DHL-5, and OCI-LY19 (data not shown) cells were pretreated with Compound 44 (500 nM for WSU and SU-DHL-5) followed by co-treatment with a combination of Compound 44 and Everolimus (WSU: 5 nM, SU-DHL-5: 0.75 nM). In FIG. 16A, no change in sub-G1 phase of the cell cycle is seen when WSU-DLCL2 cells are treated with single agents or in combination. In FIGS. 16B and 16C, synergistic time-dependent decrease of cells in S phase and G2/M phase of the cell cycle, respectively, is seen when WSU-DLCL2 cells were treated with the combination. In FIGS. 16D, 16E, and 16F, synergistic decrease of cells in G1, S, and G2/M phases of the cell cycle, respectively, is seen 48 hours after co-treatment on SU-DHL-5 cells.

EXAMPLE 8

Compound 44 and Ibrutinib Act Synergistically to Decrease Populations of Cells in G1, S and G2/M Phases of Mutant WSU-DLCL2 Cells and Wild Type SU-DHL-5 Cells.

WSU-DLCL2, SU-DHL-5, and OCI-LY19 (data not shown) cells were pretreated with Compound 44 (WSU: 500 nM, SU-DHL-5: 1000nM) followed by co-treatment with a combination of Compound 44 and Ibrutinib (WSU: 625 nM, SU-DHL-5: 2500 nM). In FIGS. 17A, 17B, and 17C, synergistic decrease of cells in G1, S, and G2/M phases of the cell cycle, respectively, is seen 24 hours after co-treatment of WSU-DLCL2 cells compared to Compound 44 or Ibrutinib as single agents. In FIGS. 17D, 17E, and 17F, synergistic time dependent decrease of cells in G1, S, and G2/M phases of the cell cycle, respectively, is seen after co-treatment of SU-DHL-5 cells compared to Compound 44 or Ibrutinib as single agents.

EXAMPLE 9

Compound 44 and MK-2206 Act Synergistically to Decrease Populations of Cells in G1, S and G2/M Phases of Mutant WSU-DLCL2 Cells and Wild Type SU-DHL-5 and OCI-LY19 Cells.

Figure 18G:
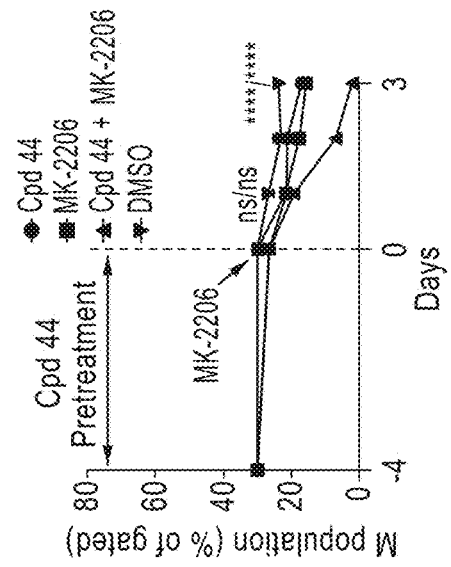
Figure 18H:
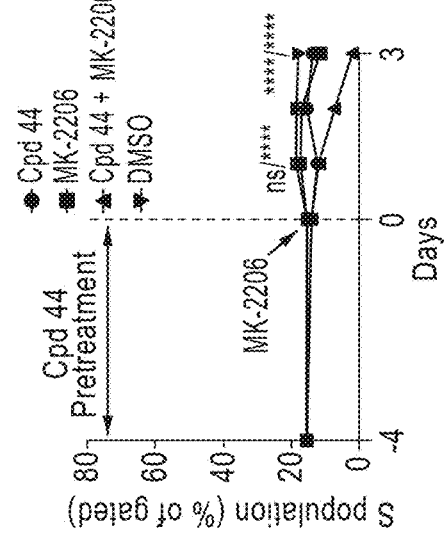
Figure 18I:
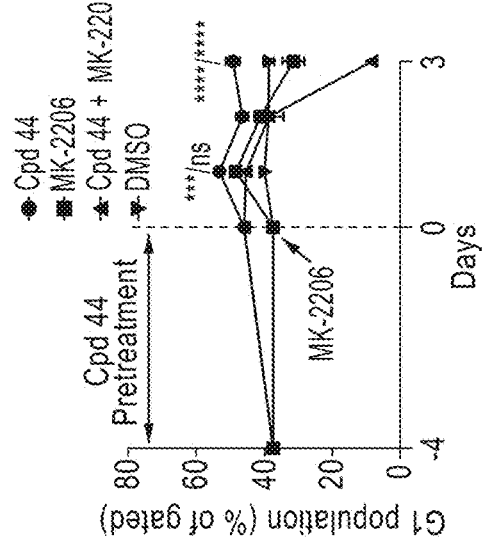

WSU-DLCL2, SU-DHL-5, and OCI-LY19 cells were pretreated with Compound 44 (2000 nM, 500 nM, and 1000 nM respectively) followed by co-treatment with a combination of Compound 44 and MK-2206 (400 nM, 250 nM, and 2500 nM respectively). In FIG. 18A, a synergistic time-dependent decrease in G1 phase of the cell cycle is seen when WSU-DLCL2 cells were treated in combination with MK-2206. In FIGS. 18B and 18C, a synergistic decrease of cells in S and G2/M phases of the cell cycle, respectively, is seen when WSU-DLCL2 cells were treated in combination. In FIGS. 18D, 18E, and 18F, synergistic decrease of cells in G1, S, and G2/M phases of the cell cycle, respectively, is seen 48 hours after co-treatment of SU-DHL-5 cells compared to single agents. In FIGS. 18G, 18H, and 18I, synergistic time-dependent decrease of cells in G1, S, and G2/M phases of the cell cycle, respectively, is seen when OCI-LY19 cells were treated in combination.

The outcomes of proliferation studies using the combination of Compound 44 with individual SOC, or other selected agents against wild type and EZH2 mutant bearing DLBCL cell lines are shown in Table 5.

TABLE 5

Proliferation study results.

| Compound | WSU-DLCL2 CR | WSU-DLCL2 CI range or 1/α | SU-DHL-10 CR | SU-DHL-10 CI range or 1/α | SU-DHL-5 CR | SU-DHL-5 CI range or 1/α | DOHH2 1/α | OCI-LY19 1/α | Toledo 1/α |
|---|---|---|---|---|---|---|---|---|---|
| Prednisolone | | 9.7 | | 4.2 | | 7.6 | 9.5 | 4.2 | No effect |
| Dexamethasone | | 17$^b$ | | 3.7 | 400:1 | 0.42-0.076 | 4.2 | 7.7 | No effect |
| ABT-199 | 4:3 | 0.27-0.002 | 3:200 | 1.2-1.4$^e$ | | No Effect | 1.9$^b$ | 4.20 | 1.9$^b$ |
| Navitoclax | 1:5 | 0.42-0.067 | 1:100 | 0.90-0.36$^a$ | | No Effect | 1.5$^b$ | 6.60 | No effect |
| Obatoclax | 40:3 | 1.10$^e$ | 1:1 | 0.91-1.36$^e$ | 320:1 | 1.26-1.61$^e$ | 1.4$^b$ | 1.50 | 1.1$^b$ |
| Ibrutinib | 4:5 | 0.39-0.14 | 1:10 | 0.78-0.062 | 1:5 | 0.22-0.002 | 0.67 | No effect | No effect |
| Idelalisib | 1:5 | 0.31-0.062 | 3:200 | 0.64-0.02 | 2:5 | 0.24-0.000025 | 0.59 | No effect | 1.1 |
| Everolimus | 400:1 | 0.34-0.003 | 100:3 | 0.65-0.14 | 4000:3 | 0.14-0.008 | 0.83 | No effect | No effect |
| Tamatinib | 1:5 | 0.24-0.025 | 3:50 | 1.1$^e$-0.061 | 1:5 | 0.57-0.19 | 0.81 | No effect | No effect |
| Trametinib | 1:5 | 0.45-0.16 | | 5.6$^b$ | 2:5 | 0.031-0.001 | 1.2$^b$ | No effect | No effect |
| MK-2206 | 4:1 | 0.77-0.005 | 3:20 | 0.56-0.04 | 2:1 | 0.28-0.001 | 0.64 | 71.40 | 1.7$^b$ |
| Rituximab | | 2.6 | | | | | | | |
| Bortezomib | 400:3 | 1.4-1.3$^e$ | 15:1 | 1.5-1$^e$ | 1600:1 | 1.00 | 0.96 | 1.67 | 0.96 |

CR = combination ratio,
CI = combination index
CI range above Fractional effect of 0.5

$^a$based on 1 experiment, other experiments are IC$_{50}$ shift values between top concentration of 6438 and drug alone, because 50% inhibition was not achieved with Compound 44
$^b$could not calculate an alpha value so IC$_{50}$ shift was reported
$^c$DOHH2 data normalized to individual 6438 concentrations instead of DMSO
d- Concentrations of Rituximab are μg/mL
$^e$These CI values were not significantly different from 1

The potency of compounds used in proliferation assays, and dose ranges used in each cell line are shown in Table 6.

TABLE 6

Compound potency and dose ranges.

| | GCB sub-type EZH2 Y646F | | | | GCB sub-type WT EZH2 | |
|---|---|---|---|---|---|---|
| | WSU-DLCL2 | | SU-DHL-10 | | SU-DHL-5 | |
| | Potency (nM) | drug range (nM) | Potency (nM) | drug range (nM) | Potency (nM) | drug range (nM) |
| Prednisolone | 90.6 | 7.8-1000 | >1000 | 7.8-1000 | 39 | 0.625-80 |
| Dexamethasone | >10000 | 0.78-100 | >100 | 0.78-100 | 3.4 | 0.078-10 |
| ABT-199 | 1942 | 23.4-3000 | 3037 | 78-10000 | >10000 | 78-10000 |
| Navitoclax | 3539 | 78-10000 | >10,000 | 78-10000 | >10000 | 78-10000 |
| Obatoclax | 59 | 1.2-50 | 19.5 | 0.78-100 | 9.8 | 0.39-50 |
| Ibrutinib | 277.7 | 39-5000 | 1146 | 187-3000 | 1327 | 312-5000 |
| Idelalisib | 2046 | 78-10000 | 8433 | 1250-10000 | 2587 | 78-10000 |
| Everolimus | 0.653 | 0.039-5 | 0.854 | 0.09-6 | 0.72 | 0.09-3 |
| Tamatinib | 3415.2 | 78-10000 | 2214 | 312.5-5000 | 3761 | 313-10000 |
| Trametinib | 8608 | 78-10000 | >10,000 | 78-10000 | >10000 | 78-10000 |
| MK-2206 | 127 | 7.8-500 | 274.6 | 7.8-500 | 162 | 7.8-1000 |
| Rituximab | >10[a] | 10-0.39[a] | | | | |
| Bortezomib | 6.5 | 0.94-7.5 | 8.6 | 5.0-20 | 4 | 0.04-5 |
| Compound 44 | 310 | 31-2000 | 73 | 3.1-200 | 3300 | 62-4000 |

| | GCB sub-type WT EZH2 | | | | | |
|---|---|---|---|---|---|---|
| | DOHH-2 | | OCI-LY19 | | Toledo | |
| | Potency | drug range (nM) | Potency | drug range (nM) | Potency | drug range (nM) |
| Prednisolone | 133 | 7.8-1000 | 47 | 0.78-100 | >1000 | 7.8-1000 |
| Dexamethasone | 5.6 | 1.56-200 | 79 | 0.078-10 | >100 | 0.78-100 |
| ABT-199 | 77 | 7.8-1000 | 53 | 1.56-200 | 190 | 4.69-600 |
| Navitoclax | 540 | 78-10000 | 131 | 15.6-2000 | 590 | 11.7-1500 |
| Obatoclax | 51 | 1.56-200 | 42 | 1.56-200 | 96 | 1.17-150 |
| Ibrutinib | 956 | 39-5000 | >10000 | 78-10000 | >10000 | 78-10000 |
| Idelalisib | 2984 | 78-10000 | >10000 | 78-10000 | 9796 | 78-10000 |
| Everolimus | 0.13 | 0.078-5 | ND | 7.8-1000 | 0.1 | 0.078-10 |
| Tamatinib | 1209 | 78-10000 | >10000 | 78-10000 | 3200 | 78-10000 |
| Trametinib | >10000 | 78-10000 | ND (*>10,000 prism) | 78-10000 | >10000 | 78-10000 |
| MK-2206 | 86 | 7.8-1000 | 304 | 78-1000 | 95 | 7.8-1000 |
| Rituximab | | | | | | |
| Bortezomib | 6.6 | 0.078-10 | 12 | 0.23-30 | 4.3 | 0.12-15 |
| Compound 44 | >10000 | 31.3-2000 | >10000 | 125-8000 | >10000 | 15.6-1000 |

[a] Concentrations of Rituximab are in μg/ml
$IC_{50}$ values listed are calculated after 3 days of dosing except for Toledo which were dosed for 5 days
Compound 44 $IC_{50}$s were calculated after 7 days for all cell lines except for Toledo which was calculated after 11 days of treatment Incorporation by Reference All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

Equivalents

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method for treating cancer in a patient in need thereof comprising administering:
   (i) a therapeutically effective amount of an EZH2 inhibitor and a therapeutically effective amount of a standard of care agent;
   (ii) a therapeutically effective amount of a combination comprising an EZH2 inhibitor and a standard of care agent; or
   (iii) a therapeutically effective amount of a composition comprising an EZH2 inhibitor and a standard of care agent;

wherein the EZH2 inhibitor is Compound 44 having the following formula:

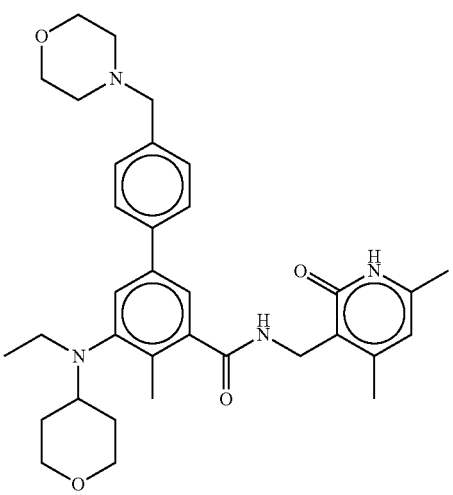

or a pharmaceutically acceptable salt thereof; and
wherein the standard of care agent is one or more compounds selected from the group consisting of navitoclax, obatoclax, ABT-199, MK-2206, idelalisib, trametinib, tamatinib, and ibrutinib.

2. The method of claim 1, wherein the cancer is a Non-Hodgkin's lymphoma.

3. The method of claim 2, wherein the Non-Hodgkin lymphoma is DLBCL (diffuse large B-cell lymphoma) or GCB (germinal center B-cell-like) lymphoma.

4. The method of claim 1, wherein (i) the cancer is an EZH2 wild type cancer, or (ii) the cancer is characterized by increased trimethylation at H3K27, or (iii) the cancer is an EZH2 inhibitor resistant or refractory cancer.

5. The method of claim 3, wherein the lymphoma is an EZH2 mutant lymphoma.

6. The method of claim 5, wherein the EZH2 mutant lymphoma has an Y646, A682 or A692 mutation.

7. The method of claim 1, wherein the standard of care agent is a PI3K/Akt/mTOR signaling cascade inhibitor.

8. The method of claim 1, wherein the EZH2 inhibitor and the standard of care agent are administered simultaneously or sequentially.

9. The method of claim 1, wherein the EZH2 inhibitor is administered prior to administration of the standard of care agent.

10. The method of claim 1, wherein the patient has upregulated expression of at least one gene selected from the group consisting of Sestrin, TNF, GILZ, and glucocorticoid target genes.

11. The method of claim 10, wherein the upregulation of the at least one gene is used to determine or adjust the therapeutically effective amount of the EZH2 inhibitor, or the upregulation of a gene is used to determine or adjust the therapeutically effective amount of the standard of care agent.

12. The method of claim 10, wherein the patient has upregulated expression of Sestrin, TNF or GILZ.

13. The method of claim 1, wherein the patient is further administered an R-CHOP component.

14. The method of claim 1, wherein the patient is further administered prednisolone or dexamethasone.

15. The method of claim 1, wherein the standard of care agent is two or more compounds selected from the group consisting of navitoclax, obatoclax, ABT-199, MK-2206, idelalisib, trametinib, tamatinib, and ibrutinib.

16. The method of claim 15, wherein the standard of care agent comprises navitoclax, obatoclax, or ABT-199.

17. The method of claim 15, wherein the standard of care agent is a PI3K/Akt/mTOR signaling cascade inhibitor.

18. The method of claim 15, wherein the standard of care agent comprises MK-2206, idelalisib, trametinib, tamatinib, or ibrutinib.

19. The method of claim 1, wherein the standard of care agent is navitoclax.

20. The method of claim 1, wherein the standard of care agent is obatoclax.

21. The method of claim 1, wherein the standard of care agent is ABT-199.

22. The method of claim 1, wherein the standard of care agent is MK-2206.

23. The method of claim 1, wherein the standard of care agent is idelalisib.

24. The method of claim 1, wherein the standard of care agent is trametinib.

25. The method of claim 1, wherein the standard of care agent is ibrutinib.

* * * * *